(12) United States Patent
Weikart et al.

(10) Patent No.: US 11,654,046 B2
(45) Date of Patent: May 23, 2023

(54) PHARMACEUTICAL PACKAGE FOR OPHTHALMIC FORMULATIONS

(71) Applicant: SIO2 MEDICAL PRODUCTS, INC., Auburn, AL (US)

(72) Inventors: Christopher Weikart, Auburn, AL (US); Murray Stephen Bennett, Bellingham, WA (US); Jean-Pierre Giraud, Auburn, AL (US)

(73) Assignee: SIO2 MEDICAL PRODUCTS, INC., Auburn, AL (US)

( * ) Notice: Subject to any disclaimer, the term of this patent is extended or adjusted under 35 U.S.C. 154(b) by 818 days.

(21) Appl. No.: 15/777,279

(22) PCT Filed: Nov. 18, 2016

(86) PCT No.: PCT/US2016/062885
§ 371 (c)(1),
(2) Date: May 18, 2018

(87) PCT Pub. No.: WO2017/087871
PCT Pub. Date: May 26, 2017

(65) Prior Publication Data
US 2018/0325728 A1 Nov. 15, 2018

Related U.S. Application Data

(60) Provisional application No. 62/257,208, filed on Nov. 18, 2015.

(51) Int. Cl.
*A61F 9/00* (2006.01)
*A61K 9/00* (2006.01)
(Continued)

(52) U.S. Cl.
CPC ........... *A61F 9/0017* (2013.01); *A61J 1/1468* (2015.05); *A61K 9/0048* (2013.01);
(Continued)

(58) Field of Classification Search
CPC .......... A61M 5/31501; A61M 5/31511; A61M 5/31515; A61M 5/31576; A61M 5/3121;
(Continued)

(56) References Cited

U.S. PATENT DOCUMENTS 4,184,593 A 1/1980 Dorr
4,294,695 A 9/1981 Bekkering et al.
(Continued)

FOREIGN PATENT DOCUMENTS

DE 102009023335 A1 12/2010
EP 0649318 4/1995
(Continued)

OTHER PUBLICATIONS

The biologies license application for Lucentis published online at https://www.accessdata.fda.gov/drugsatfda_docs/label/2014/125156s105lbl.pdf on Apr. 12, 2016 (Year: 2016).*
(Continued)

*Primary Examiner* — Lee E Sanderson
(74) *Attorney, Agent, or Firm* — McAndrews, Held & Malloy, Ltd.

(57) ABSTRACT

A liquid formulation of an ophthalmic drug in a pharmaceutical package, for example a syringe, cartridge, or vial, made in part or in whole of a thermoplastic polymer, coated on the interior with a tie coating or layer, a barrier coating or layer, a pH protective coating or layer, and optionally a lubricity coating or layer.

32 Claims, 31 Drawing Sheets

(51) Int. Cl.

| | |
|---|---|
| *C23C 16/40* | (2006.01) |
| *C23C 16/505* | (2006.01) |
| *C23C 16/04* | (2006.01) |
| *A61J 1/14* | (2006.01) |
| *A61K 39/395* | (2006.01) |
| *A61L 31/08* | (2006.01) |
| *A61L 31/14* | (2006.01) |
| *A61M 5/31* | (2006.01) |
| *A61M 5/315* | (2006.01) |
| *A61M 5/32* | (2006.01) |
| *A61M 5/50* | (2006.01) |
| *A61M 5/00* | (2006.01) |

(52) U.S. Cl.
CPC .......... *A61K 39/3955* (2013.01); *A61L 31/08* (2013.01); *A61L 31/088* (2013.01); *A61L 31/14* (2013.01); *A61M 5/3129* (2013.01); *A61M 5/31505* (2013.01); *A61M 5/3202* (2013.01); *A61M 5/5086* (2013.01); *C23C 16/045* (2013.01); *C23C 16/401* (2013.01); *C23C 16/505* (2013.01); *A61L 2400/10* (2013.01); *A61L 2420/08* (2013.01); *A61M 5/002* (2013.01); *A61M 2005/3131* (2013.01); *A61M 2205/0222* (2013.01); *A61M 2207/10* (2013.01)

(58) Field of Classification Search
CPC ...... A61M 5/31513; A61M 2005/3123; A61M 2205/0222; A61M 2205/0238; A61M 5/178; A61M 5/315; A61F 9/0008; A61F 9/0026; A61L 31/048
USPC .................................................. 604/228, 229
See application file for complete search history.

(56) References Cited

U.S. PATENT DOCUMENTS

| | | | |
|---|---|---|---|
| 4,424,057 A | 1/1984 | House | |
| 4,820,278 A | 4/1989 | Balisky | |
| 4,846,801 A | 7/1989 | Okuda et al. | |
| 4,874,381 A | 10/1989 | Vetter | |
| 4,986,820 A | 1/1991 | Fischer | |
| 5,069,670 A | 12/1991 | Vetter et al. | |
| RE34,845 E | 1/1995 | Vetter et al. | |
| 5,411,489 A * | 5/1995 | Pagay | A61M 5/31513 |
| | | | 604/218 |
| 5,607,400 A * | 3/1997 | Thibault | A61M 5/31513 |
| | | | 604/218 |
| 5,731,144 A | 3/1998 | Toothman et al. | |
| 5,731,424 A | 3/1998 | Toothman et al. | |
| 6,124,449 A | 9/2000 | Gold et al. | |
| 6,207,816 B1 | 3/2001 | Gold et al. | |
| 6,432,089 B1 * | 8/2002 | Kakimi | A61M 5/14546 |
| | | | 604/218 |
| 6,582,959 B2 | 6/2003 | Kim | |
| 6,703,020 B1 | 3/2004 | Thorpe et al. | |
| 7,985,188 B2 * | 7/2011 | Felts | B05D 1/62 |
| | | | 600/573 |
| 8,067,070 B2 | 11/2011 | Klein et al. | |
| 9,192,725 B2 | 11/2015 | Kawamura | |
| 9,340,594 B2 | 5/2016 | Furfine et al. | |
| 2003/0190317 A1 | 10/2003 | Baca et al. | |
| 2004/0231926 A1 | 11/2004 | Sakhrani et al. | |
| 2008/0262435 A1 | 10/2008 | Erickson et al. | |
| 2010/0270335 A1 | 10/2010 | Pa | |
| 2011/0137263 A1 * | 6/2011 | Ashmead | A61M 5/31513 |
| | | | 604/230 |
| 2011/0282297 A1 * | 11/2011 | Westbye | A61M 5/5086 |
| | | | 604/198 |
| 2012/0003497 A1 | 1/2012 | Handy et al. | |
| 2012/0010573 A1 * | 1/2012 | Lundquist | B29C 45/14311 |
| | | | 604/192 |
| 2014/0012227 A1 | 1/2014 | Sigg et al. | |
| 2014/0251859 A1 * | 9/2014 | Weikart | A61L 31/16 |
| | | | 206/524.9 |
| 2015/0105734 A1 * | 4/2015 | Bryant | A61M 5/31505 |
| | | | 604/218 |
| 2016/0067405 A1 | 3/2016 | Matusch | |

FOREIGN PATENT DOCUMENTS

| | | |
|---|---|---|
| EP | 0666868 | 8/1995 |
| EP | 0764450 A1 | 3/1997 |
| EP | 0882467 A2 | 12/1998 |
| EP | 0649318 B1 | 3/1999 |
| EP | 0882467 A3 | 10/1999 |
| EP | 0764450 B1 | 8/2002 |
| EP | 0882467 B1 | 10/2003 |
| EP | 2251455 A2 | 11/2010 |
| EP | 2601991 B1 | 1/2016 |
| GB | 2500092 A | 9/2013 |
| JP | 2005073930 | 3/2005 |
| JP | 2013541375 | 11/2013 |
| JP | 2014028114 | 2/2014 |
| WO | 9410202 A1 | 5/1994 |
| WO | 9426334 A1 | 11/1994 |
| WO | 9630046 A1 | 10/1996 |
| WO | 9845331 A2 | 10/1998 |
| WO | 9845332 A2 | 10/1998 |
| WO | 9075319 A1 | 12/2000 |
| WO | 2005044853 A2 | 5/2005 |
| WO | 2009099641 A2 | 8/2009 |
| WO | 2009155724 A2 | 12/2009 |
| WO | 2010060748 A1 | 6/2010 |
| WO | 2011117878 A1 | 9/2011 |
| WO | 2011135067 A1 | 11/2011 |
| WO | 2012044744 | 4/2012 |
| WO | 2014005728 A1 | 1/2014 |
| WO | WO-2014005728 A1 * | 1/2014 ............ A61M 5/315 |
| WO | 2014052792 A1 | 4/2014 |
| WO | 2014085346 A1 | 6/2014 |
| WO | 2014085348 A2 | 6/2014 |
| WO | 2014164928 | 10/2014 |
| WO | 2014164928 A1 | 10/2014 |
| WO | WO-2014164928 A1 * | 10/2014 .......... A61M 5/3129 |
| WO | 2015054075 | 4/2015 |
| WO | 2015071348 A1 | 5/2015 |
| WO | 2015173260 A1 | 11/2015 |
| WO | 2018123276 A1 | 7/2018 |

OTHER PUBLICATIONS

Bakri et al., "Intravitreal Silicone Oil Droplets After Intravitreal Drug Injections", Retina, vol. 28, pp. 996-1001 (2008).
Bell et al., "Oligonucleotide NX1838 Inhibits VEGF165 Mediated Cellular Responses in vitro", In Vitro Cell. Div. Biol.—Animal, vol. 35, pp. 533-542 (1999).
Chen et al., "Selection and Analysis of an Optimized Anti-VEGF Antibody: Crystal Structure of an Affinity-matured Fab in Complex with Antigen", J. Mol. Biol., vol. 293, pp. 865-881 (1999).
Green et al., "Inhibitory DNA Ligands to Platelet-Dervied Growth Factor B-Chain", Biochemistry, vol. 35, pp. 14413-14424 (1996).
Holash et al., "VEGF-Trap: A VEGF blocker with potent antitumor effects", PNAS, vol. 99, No. 17, pp. 11393-11398 (2002).
Johnson et al., "Ocular and Systemic Safety of Bevacizumab and Ranibizumab in Patients with Neovascular Age-Related Macular Degeneration", Curr. Opin. Ophthalmol., vol. 24, pp. 205-212 (2013).
Liu et al., "Root Cause Analysis of Tungsten-Induced Protein Aggregation in Pre-Filled Syringes", PDA J. Pharm. Sci. and Tech., vol. 64, pp. 11-19 (2010).
Popkov et al., "Human/Mouse Cross-Reactive Anti-VEGF Receptor 2 Recombinant Antibodies Selected from an Immune b9 Allotype Rabbit Antibody Library", Jounral of Immunological Methods, vol. 288, pp. 149-164 (2004).

(56) References Cited

OTHER PUBLICATIONS

Pryce Lewis et al., "HWCVD of Polymers: Commercialization and Scale-Up", Thin Solid Films, vol. 517, pp. 3551-3554 (2009).
Seidl et al., "Tungsten-Induced Denaturation and Aggregation of Epoetin Alfa During Primary Packaging as a Cause of Immunogenicity", Pharm. Res., vol. 29, pp. 1454-1467 (2012).
Wolgemuth, "Challenges with Prefilled Syringes: The Parylene Solution", www.ondrugdelivery.com, pp. 44-45 (2012).
International Search Report for PCT/US2016/062767, dated Feb. 8, 2017.

* cited by examiner

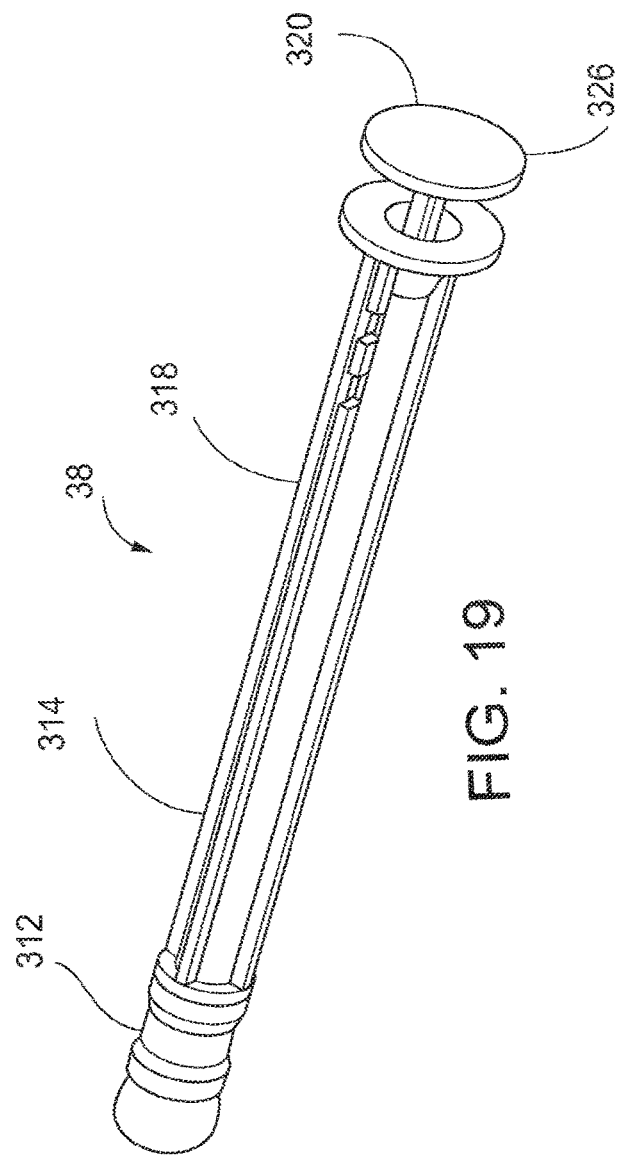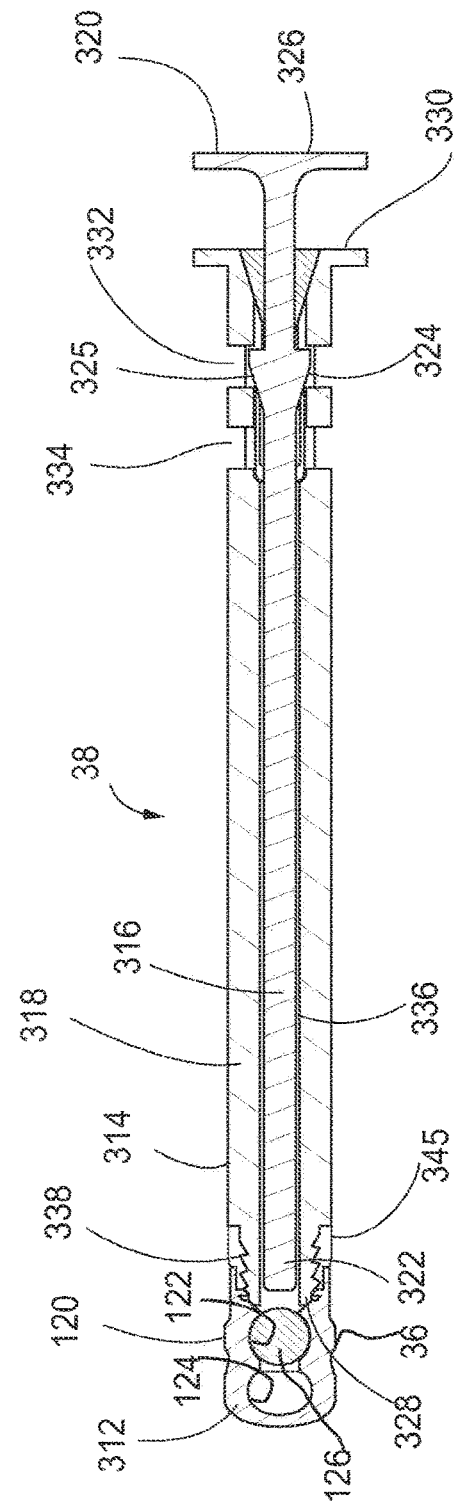
FIG. 19
FIG. 20

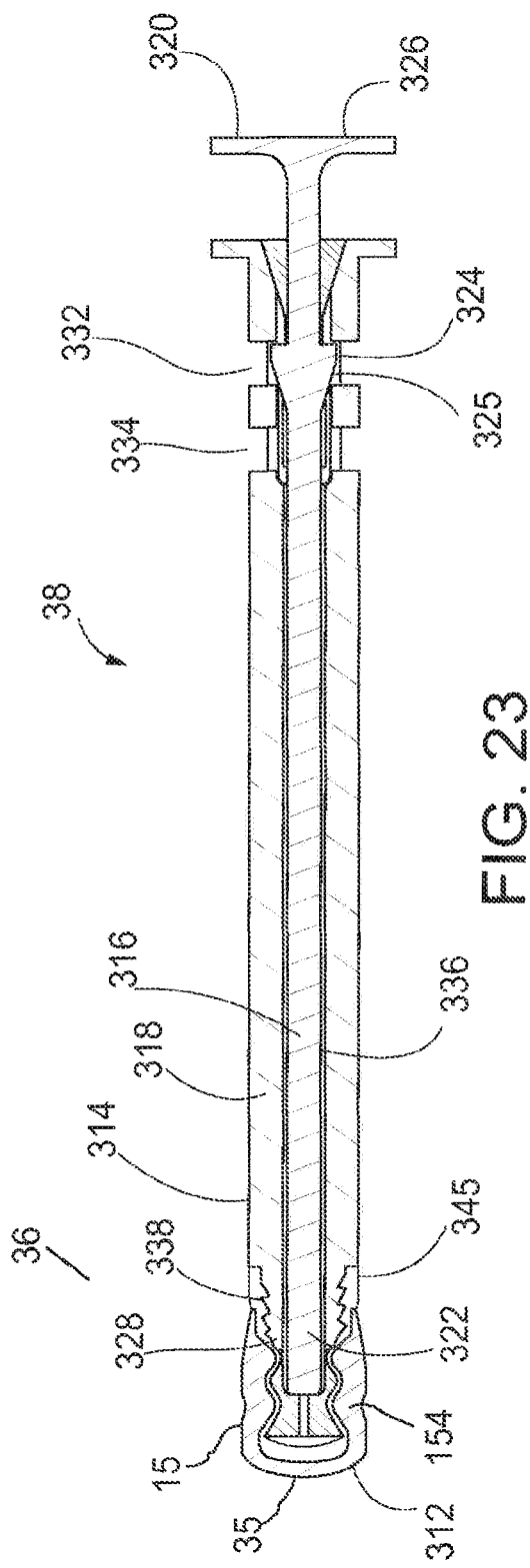
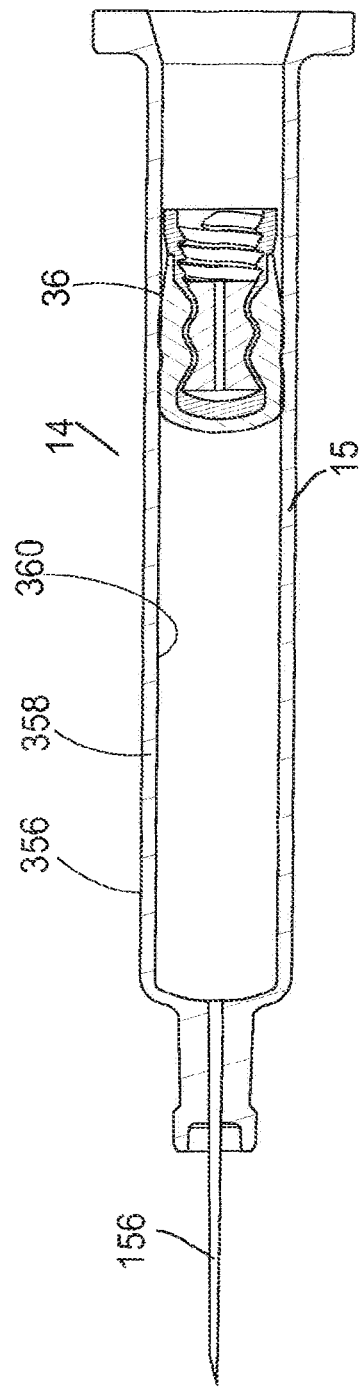

PHARMACEUTICAL PACKAGE FOR OPHTHALMIC FORMULATIONS

This application is a U.S. National Phase of International Application No. PCT/US2016/062885, filed Nov. 18, 2016, which claims priority to U.S. Provisional Patent Application No. 62/257,208 filed Nov. 18, 2015. The entire specification and all the drawings of Ser. No. 62/257,208 and each of the following patent applications is incorporated here by reference to provide continuity of disclosure: U.S. Provisional Applications 61/776,733, filed Mar. 11, 2013, and 61/800,746, filed Mar. 15, 2013; U.S. Pat. No. 7,985,188; PCT Application PCT/US14/23813, filed Mar. 11, 2014; and published PCT Publ. Appl. WO2014085348 (A2), WO2014164928 (A1), WO2014/005728 A1, and WO2015/071,348. The entire specification and all the drawings of each of these applications are incorporated here by reference to provide continuity of disclosure.

FIELD OF THE INVENTION

The present invention relates generally to liquid formulations of VEGF-antagonists in pre-filled pharmaceutical packages, for example pre-filled syringes, for intravitreal injection (injection of medication into the vitreous body of the eye). Such pharmaceutical packages are suitable for storage and intravitreal administration of liquid formulations of drugs, for example VEGF-antagonists, for example Ranibizumab, Aflibercept, or Bevacizumab.

BACKGROUND OF THE INVENTION

Ocular diseases such as age-related macular degeneration and diabetic macular oedema are caused by the uncontrolled growth of blood vessels in the eye. Hence, one option to treat these and similar diseases is to inhibit angiogenesis in the eye. Since VEGF is a key factor in the stimulation of angiogenesis, it is an attractive target for down-regulating angiogenesis. Many treatments for these and other ocular diseases require intravitreal injection of liquid pharmaceutical formulations.

The term "intravitreal injection" refers to the administration of a pharmaceutical composition in which the substance is injected directly into the eye. More specifically, the substance is injected into the vitreous humour (also called vitreous body or simply vitreous) which is the clear gel that fills the space between the lens and the retina of the eyeball of humans and other vertebrates.

WO 2014005728 A1 discloses pre-filled syringes containing a VEGF-antagonist; the syringes have low silicone oil content. The whole disclosure of this document is focused on the use of glass syringes and therefore teaches that a low amount of silicone oil has to be present within the syringe.

Currently, LUCENTIS® (Ranibizumab injection) is an approved drug in the United States and Europe for intravitreal injection, for example for treatment of diabetic macular oedema. It is available packaged in glass vials. Recently, a pre-filled Ranibizumab syringe has been approved by the European Medicines Agency (EMA). The syringe barrel consists of borosilicate glass which is spray-coated with silicon oil-in-water emulsion and subsequently heat-fixed (so-called "baked silicone") (poster presentation by Clunas et al. at the 5th World Congress on Controversies in Ophthalmology, Mar. 20-23, 2014; poster presentation of Michaud et al. at the ARVO Annual Meeting 2014).

Pre-filled syringes have many benefits compared to a vial and a separately provided syringe, such as improved convenience, affordability, accuracy, sterility, and safety. The use of pre-filled syringes results in greater dose precision, in a reduction of the potential for needle stick injuries that can occur while drawing medication from vials, in pre-measured dosage reducing dosing errors due to the need to reconstitute and/or draw medication into a syringe, and in less overfilling of the syringe helping to reduce costs by minimizing drug waste.

The traditional glass pharmaceutical packages, including pre-filled syringes, are prone to breakage or degradation during manufacture, filling operations, shipping and use, which means that glass particulates may enter the drug.

Further, glass pre-filled syringes have been treated with silicone, in processes generally known as siliconization, to enable the correct movement of the closure within the glass barrel and thereby allow effective and accurate drug delivery. Siliconization of the traditional glass pharmaceutical packages has been used to facilitate insertion of a closure into the package, or to advance a plunger through a syringe to dispense the drug. Siliconization, however, may result in introduction of silicone particles into the drug. This problem has been observed whether using the traditional coating of silicone oil or a baked-on silicone coating. Also, glass syringes such as the approved Ranibizumab pre-filled syringe have a relatively large weight compared to plastic syringes.

When administering a drug intravitreally, it is extremely important to minimize the introduction of particles into the vitreous body of the eye, which may be seen as floaters or otherwise interfere with the patient's vision. The standards limiting the amount and size of particles in formulations for intravitreal injection—for example USP789 or Ph. Eur 5.7.1—are stringent. Nonetheless, it has been shown that silicone droplets occur in the vitreous cavity after intravitreal administration of VEGF-antagonists, and it was hypothesized that the silicone is derived from the needles and syringes used for the injections (Bakri and Ekdawi (2008) Retina 28: 996-1001).

Additionally, the glue which is necessary to attach a staked-in needle to a glass syringe can lead to impurities or increased protein oxidation (presentation of Adler at the 2011 PDA Europe The Universe of Pre-Filled Syringes and Injection Devices, Basel, 7-11 Nov. 2011; presentation of Markovic at the PDA Single Use Systems Workshop, Bethesda, 22-23 Jun. 2011).

Further, during the manufacturing of glass pre-fillable syringes, usually tungsten pins are used. It has been shown that soluble tungsten found in pre-filled glass syringes leads to protein aggregation and protein oxidation (Liu et al. (2010) PDA J. Pharm. Sci. Technol. 64(1): 11-19; Seidl et al. (2012) Pharm. Res. 29: 1454-1467).

Several non-glass pre-filled syringes have been described. WO 2011/117878 A1 discloses a polycarbonate syringe. WO 2009/099641 A2 discloses cyclic olefin polymer syringes.

Pre-filled syringes for intravitreal injection typically are usually terminally sterilized using oxidizing gases such as ethylene oxide to reduce the risk of microbial infection of the eye. Syringe barrels made from plastic typically have not been suitable for terminal sterilization because the plastic is permeable by the gases used for sterilization. Gases which enter into the pre-filled syringe may chemically react with the drug contained in the syringe and may thus significantly reduce the stability of the drug.

SUMMARY OF THE INVENTION

An aspect of the invention is an ophthalmic drug in a pre-filled pharmaceutical package including a vessel having a lumen, a liquid formulation of an ophthalmic drug suitable for intravitreal injection in the lumen, and a closure, for example a plunger or stopper, seated in the lumen.

The vessel can be, for example, a syringe barrel, cartridge, or vial. The vessel has a thermoplastic wall having an interior surface enclosing at least a portion of the lumen, an exterior surface, and a coating set on at least one of the interior surface and the exterior surface of the wall. The coating set can include a tie coating or layer, a barrier coating or layer, optionally a pH protective coating or layer, and optionally a lubricity coating or layer.

The tie coating or layer can be formed on the interior surface or the exterior surface. It has the composition $SiO_xC_yH_z$ in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS). The tie coating or layer has a facing surface facing toward the wall, and an opposed surface facing away from the wall.

The barrier coating or layer has the composition $SiO_x$, in which x is from about 1.5 to about 2.9 as measured by XPS. The barrier coating or layer has a facing surface facing toward the opposed surface of the tie coating or layer and an opposed surface facing away from the tie coating or layer.

The pH protective coating or layer, if present, has the composition $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS. The pH protective coating or layer, if present, has a facing surface facing toward the opposed surface of the barrier layer and an opposed surface facing away from the barrier layer.

The closure, for example a plunger or stopper, is seated in the lumen. It has a front face facing the liquid formulation.

Another aspect of the invention is a kit comprising one or more pre-filled pharmaceutical packages as identified above, contained in a sealed outer package. The prefilled pharmaceutical package is sterile and the thermoplastic wall contains residual ethylene oxide. Optionally the sealed outer package is permeable to ethylene oxide sterilant. Optionally, the lumen is essentially free, preferably free, of ethylene oxide.

Still another aspect of the invention is a method for treating any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia, comprising administering an intravitreal injection of a liquid formulation of an ophthalmic drug contained in the pre-filled pharmaceutical package described above.

Even another aspect of the invention is use of a liquid formulation of an ophthalmic drug in the manufacture of a pre-filled pharmaceutical package described above for the treatment of any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Yet another aspect of the invention is a prefilled syringe as described above for use in a method of treating any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Some embodiments of the present invention relate to any one of the items below, in which numbers expressed using Arabic numerals optionally can be substituted for the corresponding numbers expressed here in Roman numerals, with the same meaning.

Item I is an ophthalmic drug in a pre-filled pharmaceutical package comprising:

a vessel, for example a syringe barrel, cartridge, or vial, comprising a thermoplastic wall having an interior surface enclosing at least a portion of a lumen, an exterior surface, and a coating set on at least one of the interior surface and the exterior surface of the wall, the coating set comprising:

a tie coating or layer on the interior surface or the exterior surface comprising $SiO_xC_yH_z$ in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS), the tie coating or layer having a facing surface facing toward the wall, the tie coating or layer also having an opposed surface facing away from the wall;

a barrier coating or layer of $SiO_x$, in which x is from about 1.5 to about 2.9 as measured by XPS, the barrier coating or layer having a facing surface facing toward the opposed surface of the tie coating or layer and an opposed surface facing away from the tie coating or layer;

optionally, a pH protective coating or layer of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS, the pH protective coating or layer, if present, having a facing surface facing toward the opposed surface of the barrier layer and an opposed surface facing away from the barrier layer;

in the lumen, a liquid formulation of an ophthalmic drug suitable for intravitreal injection; and a closure, for example a plunger or stopper, seated in the lumen having a front face facing the liquid formulation.

Item II is an ophthalmic drug in a pre-filled pharmaceutical package according to item I, having a nominal maximum fill volume of 0.2 ml to 10 mL, alternatively 0.2 to 1.5 mL, alternatively 0.5 ml to 1.0 ml, alternatively 0.5 ml, 1.0 ml, 3 mL, or 5 mL.

Item III is an ophthalmic drug in a pre-filled pharmaceutical package according to any one of the preceding items I or II, in which the front face of the plunger has a fluoropolymer surface, optionally a molded fluoropolymer surface or a fluoropolymer coating or layer, for example a laminated fluoropolymer film or a fluoropolymer coating.

Item IV is an ophthalmic drug in a pre-filled pharmaceutical package according to any one of the preceding items, wherein the ophthalmic drug suitable for intravitreal injection comprises a VEGF antagonist.

Item V is an ophthalmic drug in a pre-filled pharmaceutical package according to item IV, wherein the VEGF antagonist comprises an anti-VEGF antibody or an antigen-binding fragment of such antibody.

Item VI is an ophthalmic drug in a pre-filled pharmaceutical package according to item IV, wherein the VEGF antagonist comprises Ranibizumab, Aflibercept, Bevacizumab, or a combination of two or more of these, optionally Ranibizumab.

Item VII is an ophthalmic drug in a pre-filled pharmaceutical package according to any one of the preceding items, wherein the concentration of the liquid formulation of an ophthalmic drug suitable for intravitreal injection is 1 to 100 mg of the drug active agent per ml. of the liquid formulation (mg/ml), alternatively 2-75 mg/ml, alternatively 3-50 mg/ml, alternatively 5 to 30 mg/ml, and alternatively 6 or 10 mg/ml.

Item VIII is an ophthalmic drug in a pre-filled pharmaceutical package according to any one of the preceding items, in which the liquid formulation of an ophthalmic drug suitable for intravitreal injection comprises 6 mg/mL, alternatively 10 mg/mL, of Ranibizumab.

Item IX is an ophthalmic drug in a pre-filled pharmaceutical package according to any one of the preceding items, in which the ophthalmic drug suitable for intravitreal injection further comprises:
 a buffer in an amount effective to provide a pH of the liquid formulation in the range from about 5 to about 7;
 a non-ionic surfactant in the range of 0.005 to 0.02% mg./mL of complete formulation, alternatively in the range of 0.007 to 0.018% mg./mL of complete formulation, alternatively in the range of 0.008 to 0.015% mg./mL of complete formulation, alternatively in the range of 0.009 to 0.012% mg./mL of complete formulation, alternatively in the range of 0.009 to 0.011% mg./mL of complete formulation, alternatively 0.01% mg./mL of complete formulation; and
 water for injection.

Item X is an ophthalmic drug in a pre-filled pharmaceutical package according to any one of the preceding items, in which the ophthalmic drug suitable for intravitreal injection comprises 6 mg/mL, alternatively 10 mg/mL, of Ranibizumab; 100 mg/mL of α, α-trehalose dihydrate, 1.98 mg/mL L-histidine; and 0.1 mg/mL Polysorbate 20 in water for injection, qs to 1.0 mL.

Item XI is an ophthalmic drug in a pre-filled pharmaceutical package according to any one of the preceding items, having a shelf life of at least six months, alternatively at least 12 months, alternatively at least 18 months, alternatively 24 months, measured at a temperature of 5° C., alternatively 25° C.

Item XII is an ophthalmic drug in a pre-filled pharmaceutical package according to any one of the preceding items, which is free of silicone oil on the product contacting surfaces of the pre-filled pharmaceutical package.

Item XIII is an ophthalmic drug in a pre-filled pharmaceutical package according to any one of the preceding items, which is free of baked-on silicone on the product contacting surfaces of the pre-filled pharmaceutical package.

Item XIV is an ophthalmic drug in a pre-filled pharmaceutical package according to any one of the preceding items, which is a syringe comprising a barrel and a plunger, the syringe having a plunger sliding force of less than or equal to 10N for advancing the plunger in the lumen.

Item XV is an ophthalmic drug in a pre-filled pharmaceutical package according to any one of the preceding items, which is a syringe comprising a barrel and a plunger, the syringe having a breakout force of less than or equal to 10N for initiating travel of the plunger in the lumen.

Item XVI is an ophthalmic drug in a pre-filled pharmaceutical package according to any one of the preceding items, in which the ophthalmic drug suitable for intravitreal injection meets the particle count standard for particulate matter in ophthalmic solutions of USP789 as in force on Nov. 1, 2015, or Ph. Eur 5.7.1 as in force on Nov. 1, 2015, or both, at the time of filling the pre-filled syringe, alternatively after three months of storage of the pre-filled syringe at 4-8° C., alternatively after three months of storage of the pre-filled syringe at 25° C. and 60% relative humidity, alternatively after three months of storage of the pre-filled syringe at 40° C. and 75% relative humidity.

Item XVII is an ophthalmic drug in a pre-filled pharmaceutical package according to any one of the preceding items, in which the thermoplastic wall comprises a polyolefin, for example a cyclic olefin polymer, a cyclic olefin copolymer, or polypropylene; a polyester, for example polyethylene terephthalate; a polycarbonate; or any combination or copolymer of any two or more of these, optionally cyclic olefin polymer (COP) resin.

Item XVIII is an ophthalmic drug in a pre-filled pharmaceutical package according to any one of the preceding items, in which:
 the tie coating or layer comprising $SiO_xC_yH_z$ is between 5 and 200 nm (nanometers), alternatively between 5 and 100 nm, alternatively between 5 and 50 nm, alternatively about 38 nm thick as determined by transmission electron microscopy;
 the barrier coating or layer of $SiO_x$ is from 2 to 1000 nm, alternatively from 4 nm to 500 nm, alternatively between 10 and 200 nm, alternatively from 20 to 200 nm, alternatively from 30 to 100 nm, alternatively about 55 nm thick as determined by transmission electron microscopy; and
 the pH protective coating or layer of $SiO_xC_yH_z$, if present, is about from between 10 and 1000 nm, alternatively from 20 nm to 800 nm, alternatively from 50 nm to 600 nm, alternatively from 100 nm to 500 nm, alternatively from 200 nm to 400 nm, alternatively from 250 nm to 350 nm, alternatively about 270 nm, alternatively about 570 nm thick as determined by transmission electron microscopy.

Item XIX is an ophthalmic drug in a pre-filled pharmaceutical package according to any one of the preceding items, in which, for the pH protective coating or layer of $SiO_xC_yH_z$, if present, x is from about 1 to about 2 as measured by XPS, y is from about 0.6 to about 1.5 as measured by XPS, and z is from about 2 to about 5 as measured by RBS or HFS.

Item XX is an ophthalmic drug in a pre-filled pharmaceutical package according to any one of the preceding items, in which for the pH protective coating or layer of $SiO_xC_yH_z$, if present, x is about 1.1 as measured by XPS, y is about 1 as measured by XPS, and z is from about 2 to about 5 as measured by RBS or HFS.

Item XXI is an ophthalmic drug in a pre-filled pharmaceutical package according to any one of the preceding items, in which the pH protective coating or layer of $SiO_xC_yH_z$, if present, has a density between 1.25 and 1.65 g/cm$^3$, alternatively between 1.35 and 1.55 g/cm$^3$, alternatively between 1.4 and 1.5 g/cm$^3$, alternatively between 1.44 and 1.48 g/cm$^3$, as determined by X-ray reflectivity (XRR).

Item XXII is an ophthalmic drug in a pre-filled pharmaceutical package according to any one of the preceding items, in which the pH protective coating or layer of $SiO_xC_yH_z$, if present, has an RMS surface roughness value (measured by AFM) of from about 5 to about 9, alternatively from about 6 to about 8, alternatively from about 6.4 to about 7.8.

Item XXIII is an ophthalmic drug in a pre-filled pharmaceutical package according to any one of the preceding items, in which the pH protective coating or layer of $SiO_xC_yH_z$, if present, has an $R_a$ surface roughness value of the pH protective coating or layer, measured by AFM, from about 4 to about 6, alternatively from about 4.6 to about 5.8.

Item XXIV is an ophthalmic drug in a pre-filled pharmaceutical package according to any one of the preceding items, in which the pH protective coating or layer of $SiO_xC_yH_z$, if present, has an $R_{max}$ surface roughness value of the pH protective coating or layer, measured by AFM, from about 70 to about 160, alternatively from about 84 to about 142, alternatively from about 90 to about 130.

Item XXV is an ophthalmic drug in a pre-filled pharmaceutical package according to any one of the preceding items, in which the pH protective coating or layer of $SiO_xC_yH_z$, if present, has a contact angle (with distilled water) of from 90° to 110°, alternatively from 80° to 120°, alternatively from 70° to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement."

Item XXVI is an ophthalmic drug in a pre-filled pharmaceutical package according to any one of the preceding items, in which the pH protective coating or layer of $SiO_xC_yH_z$, if present, has an FTIR absorbance spectrum having a ratio from greater than 0.75 to 1.7, alternatively between 0.9 and 1.5, alternatively between 1.1 and 1.3, between the maximum amplitude of the Si—O—Si symmetrical stretch peak normally located between about 1000 and 1040 $cm^{-1}$, and the maximum amplitude of the Si—O—Si asymmetric stretch peak normally located between about 1060 and about 1100 $cm^{-1}$.

Item XXVII is an ophthalmic drug in a pre-filled pharmaceutical package according to any one of the preceding items, in which the pH protective coating or layer of $SiO_xC_yH_z$, if present, has a silicon dissolution rate by a 50 mM potassium phosphate buffer diluted in water for injection, adjusted to pH 8 with concentrated nitric acid, and containing 0.2 wt. % polysorbate-80 surfactant (measured in the absence of the liquid formulation of a VEGF antagonist, at 40° C.), less than 170 ppb/day.

Item XXVIII is an ophthalmic drug in a pre-filled pharmaceutical package according to any one of the preceding items, comprising a 0.5 or 1 mL volumetric capacity COP syringe equipped with a fluoropolymer coated plunger front face.

Item XXIX is an ophthalmic drug in a pre-filled pharmaceutical package according to any one of the preceding items, in which the vessel is a syringe barrel having a front dispensing opening and a back opening and the closure is a plunger that is axially slidable in the syringe barrel toward the front dispensing opening, the plunger comprising:
  a sleeve having a front end facing the front dispensing opening and a back end facing the back opening,
    a first cavity in the sleeve,
    a second cavity in the sleeve spaced axially from and in communication with the first cavity, and
  an insert initially located in the first cavity and configured to be displaced axially from the first cavity to the second cavity, wherein the insert is optionally partially generally spherical in shape, the insert being configured to provide a first biasing force pressing at least a portion of the sleeve adjacent to the insert radially outward against the barrel when the insert is in the first cavity, and to provide a second such biasing force that is a smaller than the first biasing force, optionally causing the sleeve to be spaced from the barrel, when the insert is in the second cavity.

Item XXX is an ophthalmic drug in a pre-filled pharmaceutical package according to any one of the preceding items, in which the vessel is a syringe barrel having a front dispensing opening and a back opening and the closure is an axially extending plunger in the syringe barrel that is axially slidable toward the front dispensing opening, the plunger comprising:
  an axially extending central core having a storage sealing section having a storage diameter and a dispensing sealing section axially spaced from the storage sealing section and having a dispensing diameter, in which the dispensing diameter is less than the storage diameter; and
  a sealing ring encircling the central core and having a first position at the storage sealing section, where the sealing ring is compressed with storage sealing force between the central core and the barrel, and a second position at the dispensing sealing section, where either the sealing ring is compressed against the barrel with a dispensing sealing force less than the storage sealing force or the sealing ring is spaced from the barrel.

Item XXXI is an ophthalmic drug in a pre-filled pharmaceutical package according to any one of the preceding items, comprising:
  as the vessel, a syringe barrel having a front dispensing opening and a back opening;
  as the closure, an axially stretchable plunger in the syringe barrel axially slidable toward the front dispensing opening, the plunger comprising: an elastomeric sleeve, optionally made from a thermoplastic elastomer, having a sidewall and a front face facing the front dispensing opening, the sidewall comprising a stretch zone that is adapted to undergo axial elongation to convert the plunger from a storage mode to a dispensing mode, wherein the elongation reduces an outer profile of at least a portion of the sidewall, thus reducing the plunger to a constricted state.

Item XXXII is an ophthalmic drug in a pre-filled pharmaceutical package according to any one of the preceding items, in which the vessel is a syringe barrel and the closure is a plunger disposed in the syringe barrel and having an area of contact with the syringe barrel, the pre-filled pharmaceutical package further comprising a coating or layer of a crosslinked silicone lubricant, optionally a plasma crosslinked silicone lubricant, disposed on one of the syringe barrel and the plunger at the area of contact between the syringe barrel and the plunger.

Item XXXIII is an ophthalmic drug in a pre-filled pharmaceutical package according to any one of the preceding items, comprising a tamper-evident needle shield.

Item XXXIV is an ophthalmic drug in a pre-filled pharmaceutical package according to any one of the preceding items, comprising a luer lock on the syringe barrel.

Item XXXV is an ophthalmic drug in a pre-filled pharmaceutical package according to item XXXIII, comprising a dispensing opening through the luer lock, the dispensing opening having a diameter of from 0.05 mm to less than 1.8 mm, alternatively from 0.1 mm to 1.5 mm, alternatively from 0.4 mm to 0.8 mm, alternatively from 0.5 mm to 0.7 mm, alternatively about 0.6 mm.

Item XXXVI is an ophthalmic drug in a pre-filled pharmaceutical package according to any one of the preceding items, comprising the coating set on the interior surface of the wall, the coating set including the pH protective coating or layer.

Item XXXVII is an ophthalmic drug in a pre-filled pharmaceutical package according to any one of the preceding items, comprising the coating set on the exterior surface of the wall.

Item XXXVIII is an ophthalmic drug in a pre-filled pharmaceutical package according to item XXXVI, the coating set excluding the pH protective coating or layer.

Item XXXIX is an ophthalmic drug in a pre-filled pharmaceutical package according to any one of the preceding items, comprising an anti-scratch coating over the coating set.

Item XL is an ophthalmic drug in a pre-filled pharmaceutical package according to any one of the preceding items, comprising the coating set on the interior surface of the thermoplastic wall and an anti-scratch coating on the exterior surface of the thermoplastic wall.

Item XLI is an ophthalmic drug in a pre-filled pharmaceutical package according to item XXXVI or XXXVII, in which the anti-scratch coating comprises:
  a PECVD-applied coating having the following atomic ratios of Si, O, and C, measured by XPS:
    Si=1,
    O=0.7 to 1, and
    C=1.1 to 1.5;
  a film applied by wet chemistry to form a solid coating or layer;
  or both.

Item XLII is an ophthalmic drug in a pre-filled pharmaceutical package according to any one of the preceding items, in which the coating set comprises an adhesive coating or layer on the exterior surface of the thermoplastic wall, a barrier coating or layer on the adhesive coating or layer, and a topcoat applied by wet chemistry on the barrier coating or layer.

Item XLIII is an ophthalmic drug in a pre-filled pharmaceutical package according to any one of the preceding items, comprising an insert-molded staked needle and a needle shield.

Item XLIV is an ophthalmic drug in a pre-filled pharmaceutical package according to any one of the preceding items, which is suitable for terminal sterilization by a sterilizing gas, optionally ethylene oxide EO gas, optionally at a pressure of 16.6 in. Hg (=42.2 cm. Hg, 56 kilopascal, 560 mbar) for 10 hours at 120° F. (49° C.), alternatively vaporized hydrogen peroxide (VHP).

Item XLV is an ophthalmic drug in a pre-filled pharmaceutical package of any one of the preceding items for use in administering a liquid formulation of an ophthalmic drug by intravitreal injection to a patient having an ocular disease, wherein the ocular disease optionally is selected from the group consisting of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Item XLVI is an ophthalmic drug in a pre-filled pharmaceutical package for the use according to item XLIV, wherein a volume of 30 to 100 µl of the liquid formulation is administered to the patient.

Item XLVII is an ophthalmic drug in a pre-filled pharmaceutical package according to any one of the preceding items, which has been terminally sterilized.

Item XLVIII is an ophthalmic drug in a pre-filled pharmaceutical package according to any one of the preceding items, which has been terminally sterilized with ethylene oxide.

Item XLIX is a kit comprising one or more pre-filled pharmaceutical packages of any one of the preceding items, contained in a sealed outer package, in which the prefilled pharmaceutical package is sterile and the thermoplastic wall contains residual ethylene oxide, optionally in which the sealed outer package is permeable to ethylene oxide sterilant, optionally in which the lumen is essentially free, preferably free, of ethylene oxide.

Item L is a kit of item XLIX, further comprising a needle, optionally contained in the sealed outer package, optionally comprising a luer needle, alternatively a staked needle.

Item LI is a kit of item L, further comprising a needle shield installed on and enclosing at least a portion of the pharmaceutical package.

Item LII is a kit of item LI, in which the needle shield is sufficiently ethylene oxide permeable to permit ethylene oxide terminal sterilization of the entire pharmaceutical package by ethylene oxide EO gas at a pressure of 16.6 in. (42.2 cm.) Hg for 10 hours at 120° F. (49° C.) when the needle shield is installed over the needle, optionally when the pharmaceutical package is enclosed in the sealed outer package.

Item LIII is a kit of any one of the preceding items XLIX-LII, further comprising a plunger rod, optionally contained in the sealed outer package.

Item LIV is a kit of any one of the preceding items XLIX-LIII, further comprising instructions for use, optionally contained in the sealed outer package.

Item LV is a method for treating any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia, comprising administering an intravitreal injection of a liquid formulation of an ophthalmic drug contained in the pre-filled pharmaceutical package of any one of the preceding items.

Item LVI is the use of a liquid formulation of an ophthalmic drug in the manufacture of an ophthalmic drug in a pre-filled pharmaceutical package, optionally a syringe, according to any one of the preceding items for the treatment of any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Item LVII is a prefilled syringe according to any one of the preceding items for use in a method of treating any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Item LVIII is an ophthalmic drug in a pre-filled pharmaceutical package according to any one of claims 19-71, in which the plunger breakout force is determined using the ISO 7886-1:1993 test.

Item LIX is a liquid formulation of a VEGF-antagonist in a pre-filled pharmaceutical package according to any one of the preceding items XV-LVII of this specification, in which the plunger breakout force is determined using the ISO 7886-1:1993 test.

Item LX is a pre-filled pharmaceutical package according to any one of claims 18-71, in which the plunger sliding force is determined using the Protocol for Lubricity Testing defined in this specification.

Item LXI is a liquid formulation of a VEGF-antagonist in a pre-filled pharmaceutical package according to any one of the preceding items XIV-LVII of this specification, in which the plunger sliding force is determined using the Protocol for Lubricity Testing defined in this specification.

Many additional and alternative aspects and embodiments of the invention are also contemplated, and are described in the specification and claims that follow.

BRIEF DESCRIPTION OF THE DRAWINGS

FIG. 19 illustrates a perspective view of an alternative plunger assembly.

FIG. 20 illustrates an axial sectional view of a plunger assembly according to an illustrated embodiment.

FIG. 23 illustrates an axial sectional view of a plunger assembly according to an illustrated embodiment.

FIG. 24 illustrates a partial sectional view of the plunger shown in FIG. 23 positioned within a barrel of a syringe.

Figure 1:
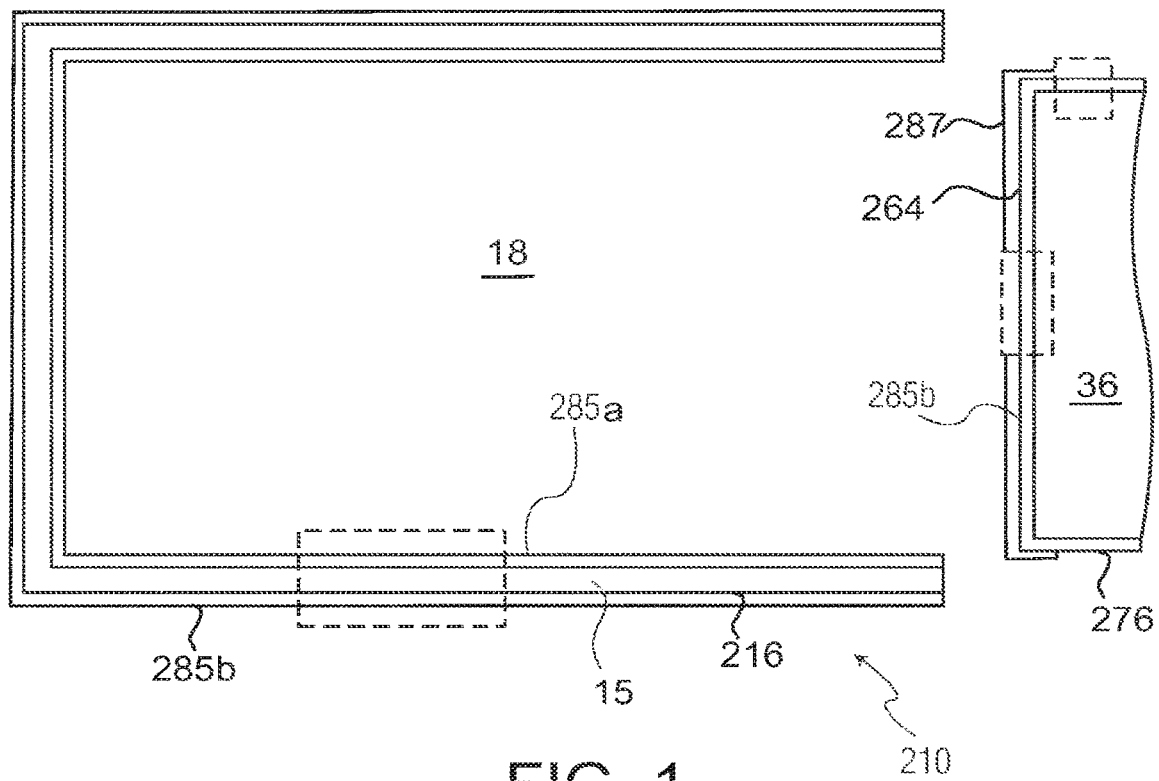
FIG. 1 is a schematic sectional view of a pharmaceutical package, with the closure removed to show detail.

The following reference characters are used in the drawing figures:

| | |
|---|---|
| 10 | Vial |
| 12 | Capped assembly or workpiece |
| 14 | Vessel (syringe barrel) |
| 15 | Wall |
| 16 | Inner or interior surface (of 15) |
| 18 | Lumen |
| 20 | Dispensing portion (e.g. needle) |
| 22 | Front end (of 14) |
| 24 | Distal opening |
| 26 | Front dispensing opening (of 14) |
| 28 | Shield |
| 30 | Barrier coating or layer |
| 32 | Back opening (of 14) |
| 33 | Anti-scratch coating |
| 34 | pH protective coating or layer |
| 35 | Front face (of 36) |
| 36 | Closure (of 210) |
| 38 | Plunger Rod |
| 40 | Formulation |
| 42 | Rib |
| 44 | Generally cylindrical interior surface |
| 46 | Barb |
| 48 | Catch |
| 50 | Vessel support |
| 60 | Apparatus for coating, for example |
| 61 | Quadro couple magnet |
| 62 | Quadro couple magnet |
| 63 | Quadro couple magnet |
| 64 | Quadro couple magnet |
| 79 | Polar axis of magnet |
| 80 | Axis |
| 81 | Recess between magnets or within coil |
| 82 | Opening |
| 92 | Vessel port |
| 94 | Vacuum duct |
| 96 | Vacuum port |
| 98 | Vacuum source |
| 100 | O-ring (of 92) |
| 102 | O-ring (of 96) |
| 104 | Gas inlet port |
| 106 | O-ring (of 100) |
| 108 | Probe (inner electrode) |
| 110 | Gas delivery port (of 108) |
| 114 | Housing (of 50) |
| 116 | Collar |
| 118 | Exterior surface |
| 120 | Sleeve (of 36) |
| 122 | First cavity (of 120) |
| 124 | Second cavity (of 120) |
| 126 | Insert |
| 130 | Central core (of 36) |
| 132 | Storage sealing section (of 36) |
| 134 | Dispensing sealing section (of 36) |
| 136 | Storage diameter (of 132) |
| 138 | Dispensing diameter (of 134) |
| 140 | Seal ring |
| 144 | PECVD gas source |
| 152 | Pressure gauge |
| 154 | Stretch zone |
| 156 | Needle |
| 158 | Kit |
| 160 | Outer electrode |
| 162 | Power supply |
| 164 | Sidewall (of 160) |
| 166 | Sidewall (of 160) |
| 168 | Closed end (of 160) |
| 170 | Sealed outer package |
| 172 | Instructions |
| 210 | Pharmaceutical package |
| 216 | Exterior surface |
| 220 | Opposed surface (of 30) |
| 222 | Facing surface (of 30) |
| 224 | Opposed surface (of 34) |
| 226 | Facing surface (of 34) |
| 264 | Inner or interior surface (of 36) |
| 276 | Side surface |
| 278 | Inner or interior surface (of 280) |
| 285b | Vessel coating set, exterior |
| 285a | Vessel coating set, interior |
| 287 | Lubricity coating or layer in 01, fluoropolymer |
| 310 | Plunger assembly |
| 312 | Convertible plunger |
| 312 | Convertible plunger |
| 314 | Plunger rod |
| 316 | Interior shaft |
| 316 | Tip |
| 318 | Exterior shaft |
| 320 | Distal end |
| 322 | Proximal end |
| 324 | Locking tab |
| 325 | Tapered surface |
| 326 | Actuator |
| 328 | First end |
| 330 | Second end |
| 332 | First recess |
| 334 | Second recess |
| 336 | Inner portion |
| 338 | Thread |
| 340 | Thread) |
| 342 | Insert |
| 344 | Sleeve |
| 345 | Connector body |
| 346 | Outer portion |
| 348 | First cavity |
| 348 | Cavity |
| 350 | Second cavity |
| 351 | Storage Sealing Section |
| 352 | Rib of Storage Sealing Section |
| 353 | Liquid Sealing Section |
| 354 | Interior area |
| 355 | Rib of Liquid Sealing Section |
| 356 | Barrel |
| 357 | Valley |
| 358 | Sidewall |
| 359 | Product containing area |
| 360 | Inner surface |
| 361 | Proximal end |
| 362 | Insert |
| 363 | Connector body |
| 364 | Sleeve |
| 365 | First section |
| 366 | Cavity |
| 367 | Second section |
| 368 | Shaft |
| 369 | Third section |

| | |
|---|---|
| 370 | Outer surface |
| 372 | Recesses |
| 374 | Protrusions |
| 376 | Inner surface |
| 377 | Recesses |
| 378 | Protrusions |
| 379 | Protrusions |
| 380 | Recesses |
| 382 | Bottom portion |
| 384 | Lower portion |
| 386 | Exterior surface |
| 388 | Film coating |
| 390 | Sidewall |
| 392 | Nose cone |
| 404 | Exhaust |
| 410 | Syringe |
| 412 | Barrel |
| 414 | Inner surface (of 412) |
| 416 | Injectable liquid |
| 418 | Needle |
| 420 | Plunger assembly |
| 422 | Plunger rod |
| 424 | Plunger |
| 426 | Threaded projection |
| 428 | Threaded bore |
| 430 | Flanged head |
| 440 | Mounting projection |
| 442 | Flange |
| 444 | Recess |
| 446 | Conical tapering section |
| 448 | Cylindrical section |
| 450 | Arrows |
| 452 | Flange |
| 454 | Elastomeric head |
| 456 | Film |
| 458 | Edge (of 456) |
| 460 | Recess |
| 502 | Plunger |
| 504 | Storage sealing ribs |
| 506 | Rib |
| 508 | Sidewall (of 502) |
| 510 | Sleeve |
| 512 | Thread |
| 514 | Hollow portion (of 510) |
| 516 | Solid portion (of 510) |
| 518 | Cap (of 502) |
| 520 | Stem (of (518) |
| 522 | Stem cover |
| 524 | Plunger rod |
| 526 | Interior shaft (of 524) |
| 528 | Exterior shaft (of 524) |
| 530 | Proximal end (of 526) |
| 532 | Thread |
| 534 | Thread (of 502) |
| 536 | Syringe barrel |
| 538 | Plunger |
| 540 | Sidewall (of 542) |
| 542 | Sleeve |
| 544 | Liquid sealing member |
| 546 | Rib |
| 548 | Rib |
| 550 | Annular gap |
| 552 | Cap |
| 556 | Plunger |
| 558 | Cap rib |
| 560 | Cap |
| 562 | Nose cone |
| 564 | Sidewall |
| 574 | Main vacuum valve |
| 576 | Vacuum line |
| 578 | Manual bypass valve |
| 580 | Bypass line |
| 582 | Vent valve |
| 584 | Main reactant gas valve |
| 586 | Main reactant feed line |
| 588 | Precursor gas |
| 590 | Organosilicon feed line (capillary) |
| 592 | Organosilicon shut-off valve |
| 594 | Oxidizing gas |
| 596 | Oxygen feed line |
| 598 | Mass flow controller |
| 600 | Oxygen shut-off valve |
| 602 | Diluent gas reservoir |
| 604 | Feed line |
| 606 | Shut-off valve |
| 614 | Headspace |
| 616 | Pressure source |
| 618 | Pressure line |
| 620 | Capillary connection |
| 724 | Plunger |
| 732 | Central core or ring carrier |
| 734 | Storage sealing section |
| 736 | Liquid sealing section |
| 738 | Storage ring |
| 740 | Lobe (of 738) |
| 744 | Annular storage platform |
| 746 | Annular gradual transition region |
| 748 | Annular dispensing platform |
| 752 | Flange |
| 754 | Head |
| 756 | Film |
| 760 | Central mating recess |
| 763 | Stem |
| 770 | Annular insertion platform |
| 772 | Prongs |
| 774 | Abutments |
| 776 | Opening |
| 780 | Connector body |
| 782 | Ridge section |
| 784 | Axial channel |
| 786 | Chamber |
| 788 | luer lock |
| 790 | Pin or needle |
| 838 | Tie coating or layer |
| 840 | Facing surface (of 838) |
| 842 | Opposed surface (of 838) |

In the context of the present invention, the following definitions and abbreviations are used:

A "pre-filled syringe" is a conventional syringe or cartridge which is supplied by the manufacturer in a filled state, i.e. a measured dose of the drug to be administered is already present in the syringe when it is purchased and ready for administration. In particular, the pharmaceutical composition containing the drug does not have to be drawn from a vial containing the composition by using an empty syringe. The term pre-filled syringe within the meaning of the present invention does not refer to syringes the content of which has been drawn from a vial in a repackaging process. A "prefilled pharmaceutical package" includes a pre-filled syringe or cartridge, but is more broadly defined to also include a vial or other type of storage vessel containing one or multiple doses of a drug which is supplied by the manufacturer in a filled state, even if the drug must be transferred to a syringe or other intermediate device for administration.

The term "at least" in the context of the present invention means "equal or more" than the number following the term. The word "comprising" does not exclude other elements or steps, and the indefinite article "a" or "an" does not exclude a plurality unless indicated otherwise. Whenever a parameter range is indicated, it is intended to disclose the parameter values given as limits of the range and all values of the parameter falling within said range.

"First" and "second" or similar references to, for example, coatings or layers, refer to the minimum number of items, such as coatings or layers, that are present, but do not necessarily represent the order or total number of coatings or layers require additional coatings or layers beyond the stated number. For example, a "first" coating or layer in the context of this specification can be either the only coating or layer or any one of plural coatings or layers, without limitation. In other words, recitation of a "first" coating or layer allows but does not require an embodiment that also has a second or further coating or layer.

For purposes of the present invention, an "organosilicon precursor" is a compound having at least one of the linkages:

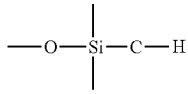

which is a tetravalent silicon atom connected to an oxygen atom and an organic carbon atom (an organic carbon atom being a carbon atom bonded to at least one hydrogen atom). A volatile organosilicon precursor, defined as such a precursor that can be supplied as a vapor in a PECVD apparatus, is an optional organosilicon precursor. Optionally, the organosilicon precursor is selected from the group consisting of a linear siloxane, a monocyclic siloxane, a polycyclic siloxane, a polysilsesquioxane, an alkyl trimethoxysilane, and a combination of any two or more of these precursors.

The feed amounts of PECVD precursors, gaseous reactant or process gases, and carrier gas are sometimes expressed in "standard volumes" in the specification and claims. The standard volume of a charge or other fixed amount of gas is the volume the fixed amount of the gas would occupy at a standard temperature and pressure (without regard to the actual temperature and pressure of delivery). Standard volumes can be measured using different units of volume, and still be within the scope of the present disclosure and claims. For example, the same fixed amount of gas could be expressed as the number of standard cubic centimeters, the number of standard cubic meters, or the number of standard cubic feet. Standard volumes can also be defined using different standard temperatures and pressures, and still be within the scope of the present disclosure and claims. For example, the standard temperature might be 0° C. and the standard pressure might be 760 Torr (as is conventional), or the standard temperature might be 20° C. and the standard pressure might be 1 Torr. But whatever standard is used in a given case, when comparing relative amounts of two or more different gases without specifying particular parameters, the same units of volume, standard temperature, and standard pressure are to be used relative to each gas, unless otherwise indicated.

The corresponding feed rates of PECVD precursors, gaseous reactant or process gases, and carrier gas are expressed in standard volumes per unit of time in the specification. For example, flow rates are expressed as standard cubic centimeters per minute, abbreviated as sccm. As with the other parameters, other units of time can be used, such as seconds or hours, but consistent parameters are to be used when comparing the flow rates of two or more gases, unless otherwise indicated.

A "vessel" in the context of the present invention can be a pharmaceutical package or other vessel. Some examples of a pharmaceutical package include, but are not limited to, a vial, a cartridge, or a syringe.

In the empirical composition $Si_wO_xC_yH_z$ or the equivalent composition $SiO_xC_yH_z$ or $SiO_xC_y$ the values of w, x, y, and z used throughout this specification should be understood as ratios or an empirical formula (for example for a coating or layer), rather than as a limit on the number or type of atoms in a molecule. For example, octamethylcyclotetrasiloxane, which has the molecular composition $Si_4O_4C_8H_{24}$, can be described by the following empirical formula, arrived at by dividing each of w, x, y, and z in the molecular formula by 4, the largest common factor: $Si_1O_1C_2H_6$. The values of w, x, y, and z are also not limited to integers. For example, (acyclic) octamethyltrisiloxane, molecular composition $Si_3O_2C_8H_{24}$, is reducible to $Si_1O_{0.67}C_{2.67}H_8$.

Also, although $SiO_xC_yH_z$ is described as equivalent to $SiO_xC_y$, it is not necessary to show the presence of hydrogen in any proportion to show the presence of $SiO_xC_y$. Unless otherwise indicated here, the value of w is normalized to 1, and the subscript w is then conventionally omitted. The coating or layer may thus in one aspect have the formula $Si_wO_xC_yH_z$, for example where w is 1, x is from about 0.5 to about 2.4, y is from about 0.6 to about 3, and z is from about 2 to about 9. The same coating or layer, with the same determination of w, x, and y, may thus in another aspect have the formula $SiO_xC_y$, for example where x is from about 0.5 to about 2.4, y is from about 0.6 to about 3, and w and z are omitted.

The atomic ratios of silicon, oxygen, and carbon can be determined by XPS. The atomic ratio of H atoms cannot be measured by XPS, which does not detect hydrogen. Optionally, the proportion of H atoms can be determined separately, for example by Rutherford backscattering (RBS) or hydrogen forward scattering (HFS), preferably the former.

The term "syringe" is broadly defined to include cartridges, injection "pens," and other types of barrels or reservoirs adapted to be assembled with one or more other components to provide a functional syringe. "Syringe" is also broadly defined to include related articles such as auto-injectors, which provide a mechanism for dispensing the contents.

A coating or layer or treatment is defined as "hydrophobic" if it lowers the wetting tension of a surface, compared to the corresponding uncoated or untreated surface. Hydrophobicity is thus a function of both the untreated substrate and the treatment.

A "lubricity layer" according to the present invention is a coating which has a lower frictional resistance than the uncoated surface. In other words, it reduces the frictional resistance of the coated surface in comparison to a reference surface that is uncoated. The present lubricity layers are primarily defined by their lower frictional resistance than the uncoated surface and the process conditions providing lower frictional resistance than the uncoated surface.

"Frictional resistance" can be static frictional resistance and/or kinetic frictional resistance.

One of the optional embodiments of the present invention is a syringe part, e.g. a syringe barrel or plunger, coated with a lubricity layer. In this contemplated embodiment, the relevant static frictional resistance in the context of the present invention is the breakout force as defined herein, and the relevant kinetic frictional resistance in the context of the present invention is the plunger sliding force as defined herein. For example, the plunger sliding force as defined and determined herein is suitable to determine the presence or absence and the lubricity characteristics of a lubricity layer or coating in the context of the present invention whenever the coating is applied to any syringe or syringe part, for example to the inner wall of a syringe barrel. The breakout force is of particular relevance for evaluation of the coating effect on a prefilled syringe, i.e. a syringe which is filled after coating and can be stored for some time, e.g. several months or even years, before the plunger is moved again (has to be "broken out").

The "plunger sliding force" (synonym to "glide force," "maintenance force," F.sub.m, also used in this description) in the context of the present invention is the force required to maintain movement of a plunger in a syringe barrel, e.g. during aspiration or dispense. It can advantageously be determined using the ISO 7886-1:1993 test known in the art. A synonym for "plunger sliding force" often used in the art is "plunger force" or "pushing force".

The "plunger breakout force" (synonym to "breakout force", "break loose force", "initiation force", F.sub.i, also used in this description) in the context of the present invention is the initial force required to move the plunger in a syringe, for example in a prefilled syringe.

Both "plunger sliding force" and "plunger breakout force" and methods for their measurement are described in more detail in subsequent parts of this description. These two forces can be expressed in N, lbs. or kg and all three units are used herein. These units correlate as follows: 1N=0.102 kg=0.2248 lbs. (pounds).

Sliding force and breakout force are sometimes used herein to describe the forces required to advance a stopper or other closure into a vessel, such as a medical sample tube or a vial, to seat the closure in a vessel to close the vessel. Its use is analogous to use in the context of a syringe and its plunger, and the measurement of these forces for a vessel and its closure are contemplated to be analogous to the measurement of these forces for a syringe, except that at least in most cases no liquid is ejected from a vessel when advancing the closure to a seated position.

"Slidably" means that the plunger, closure, or other removable part is permitted to slide in a syringe barrel or other vessel.

The term "closure" as used in this specification and claims refers to any part or subassembly of a pharmaceutical package or vessel closing the lumen, or that can be used to close the vessel lumen, and can be removed, moved, broken, deformed, pierced, or otherwise manipulated to open the package or vessel, dispense its contents, or provide access to its contents. The closure can be a separable part, such as a crimp, septum, stopper, plunger, plunger tip, cap, piston, seal, or needle shield; or an integral or joined part, such as the wall portion of an ampoule or film packet broken or parted to release contents or a web blocking the nozzle of a tube before it is pierced to release the contents through the nozzle, or a valve that is closed and can be opened. The term "closure" equally applies to a plunger tip, a plunger piston, a plunger piston and plunger tip assembly; to any of these further assembled with a plunger rod; or to any of these without a plunger rod present.

In the context of a prefilled syringe the closure is typically a stopper which is often also referred to as a plunger stopper or simply plunger. Thus, in the context of a prefilled syringe the terms "stopper", "plunger stopper" and "plunger" are used interchangably herein. The plunger stopper can be moved within the syringe barrel by a plunger rod, wherein the plunger stopper and the plunger rod may be mechanically connected. In case of a non-retractable stopper, the plunger rod is not mechanically connected to the plunger stopper. Thus, a non-retractable stopper can be pushed into the syringe barrel by pushing the plunger rod into the syringe barrel towards the outlet but it cannot be retracted by pulling the plunger rod towards the rear of the syringe barrel.

The word "comprising" does not exclude other elements or steps.

DETAILED DESCRIPTION

The present invention will now be described more fully, with reference to the accompanying drawings, in which several embodiments are shown. This invention can, however, be embodied in many different forms and should not be construed as limited to the embodiments set forth here. Rather, these embodiments are examples of the invention, which has the full scope indicated by the language of the claims. Like numbers refer to like or corresponding elements throughout. The following disclosure relates to all embodiments unless specifically limited to a certain embodiment.

VEGF-Antagonist Ocular Drugs for Intravitreal Injection

An "intraocular neovascular disease" is a disease characterized by ocular neovascularisation. Examples of intraocular neovascular diseases include, for example, proliferative retinopathies, choroidal neovascularisation (CNV), age-related macular degeneration (AMD), diabetic and other ischemia-related retinopathies, diabetic macular oedema, pathological myopia, von Hippel-Lindau disease, histoplasmosis of the eye, Central Retinal Vein Occlusion (CRVO), Branch Retinal Vein Occlusion (BRVO), corneal neovascularisation, and retinal neovascularisation. The term "age-related macular degeneration" refers to a medical condition which usually affects older adults and results in a loss of vision in the centre of the visual field (the macula) because of damage to the retina. Some or all of these conditions can be treated by intravitreal injection of a VEGF-antagonist.

The term "VEGF-antagonist" refers to a molecule which specifically interacts with VEGF and inhibits one or more of its biological activities, for example its mitogenic, angiogenic and/or vascular permeability activity. It is intended to include both anti-VEGF antibodies and antigen-binding fragments thereof and non-antibody VEGF-antagonists.

Non-antibody VEGF-antagonists include Aflibercept, Pegaptanib, and antibody mimetics. Aflibercept which is presently marketed under the name Eylea® is a recombinant human soluble VEGF receptor fusion protein in which portions of human VEGF receptors 1 and 2 extracellular domains are fused to the Fc portion of human IgG1 (Holash et al. (2002) Proc. Natl. Acad. Sci. USA 99(17): 11393-11398; WO 00/75319 A1). Pegaptanib which is presently marketed under the name Macugen® is a pegylated antivascular endothelial growth factor (VEGF) aptamer (Bell et al. (1999) In Vitro Cell Dev Biol Anim. 35(9): 533-42). Antibody mimetics which are VEGF-antagonists include binding proteins comprising an ankyrin repeat domain that binds VEGF and inhibits its binding to the receptor, such as DARPin® MP0112 (see also WO 2010/060748 and WO 2011/135067).

The term "anti-VEGF antibody" refers to an antibody or antibody fragment such as a Fab or a scFV fragment that specifically binds to VEGF and inhibits one or more of its biological activities, for example its mitogenic, angiogenic and/or vascular permeability activity. Anti-VEGF antibodies act, for example, by interfering with the binding of VEGF to a cellular receptor, by interfering with vascular endothelial cell activation after VEGF binding to a cellular receptor, or by killing cells activated by VEGF. Anti-VEGF antibodies include, for example, antibodies A4.6.1, Bevacizumab, Ranibizumab, G6, B20, 2C3, and others as described in, for example, WO 98/45331, US 2003/0190317, U.S. Pat. Nos. 6,582,959, 6,703,020, WO 98/45332, WO 96/30046, WO 94/10202, WO 2005/044853, EP 0 666 868 B1, WO 2009/155724 and Popkov et al. (2004) J. Immunol. Meth. 288: 149-64. Preferably, the anti-VEGF antibody or antigen-binding fragment thereof present in the pharmaceutical composition of the present invention is Ranibizumab or Bevacizumab. Most preferably, it is Ranibizumab or an antigen-binding fragment thereof.

"Ranibizumab" is a humanised monoclonal Fab fragment directed against VEGF-A having the light and heavy chain variable domain sequences of Y0317 as described in SEQ ID Nos. 115 and 116 of WO 98/45331 and Chen et al. (1999) J. Mol. Biol. 293: 865-81. The CAS number of Ranibizumab is 347396-82-1. Ranibizumab inhibits endothelial cell proliferation and neovascularisation and has been approved for the treatment of neovascular (wet) age-related macular degeneration (AMD), the treatment of visual impairment due to diabetic macular oedema (DME), the treatment of visual impairment due to macular oedema secondary to retinal vein occlusion (branch RVO or central RVO), or treatment of visual impairment due to choroidal neovascularisation (CNV) secondary to pathologic myopia. Ranibizumab is related to Bevacizumab and derived from the same parent mouse antibody as Bevacizumab but it is much smaller than the parent molecule and has been affinity matured to provide stronger binding to VEGF-A. Ranibizumab is produced recombinantly in *Escherichia coli*, for example as described in WO 98/45331 A2. The present commercial Ranibizumab formulation contains α, α-trehalose dihydrate, histidine hydrochloride monohydrate, histidine, polysorbate 20 and water for injection and is supplied in a concentration of 10 mg/ml. In particular, it contains 6 or 10 mg. Ranibizumab, 100 mg. α,α-trehalose dihydrate; 0.32 mg. L-histidine, 1.66 mg. L-histidine hydrochloride monohydrate, 0.1 mg Polysorbate 20 and water for injection qs to 1 mL. The pH of the present commercial Ranibizumab formulation may be adjusted to pH 5.5.

"Bevacizumab" is a full-length, humanized murine monoclonal antibody that recognizes all isoforms of VEGF and which is the parent antibody of Ranibizumab. The CAS number of Bevacizumab is 216974-75-3. Bevacizumab inhibits angiogenesis and is presently approved for the treatment of different cancer types. However, it is also used off-label in ophthalmological diseases such as age-related macular degeneration. The present commercial Bevacizumab formulation contains α, α-trehalose dihydrate, sodium phosphate, polysorbate 20 and water for injection and is supplied as a concentrate with a concentration of 25 mg/ml. In particular, it contains 25 mg/ml Bevacizumab, 240 mg α,α-trehalose dihydrate, 23.2 mg sodium phosphate (monobasic, monohydrate), 4.8 mg sodium phosphate (dibasic, anhydrous), 1.6 mg polysorbate 20, and water for Injection, USP. The antibody concentration within the pre-filled syringes of the present invention is typically 1-100 mg/ml, preferably 2-75 mg/ml, more preferably 3-50 mg/ml, even more preferably 5 to 30 mg/ml and most preferably 6 or 10 mg/ml. If Ranibizumab is contained within the pre-filled syringe of the present invention the Ranibizumab concentration is 10 mg/ml.

Aflibercept, marketed under the name Eylea®, is a recombinant fusion protein consisting of the VEGF binding portion from the extracellular domains of human VEGF receptors 1 and 2 that are fused to the Fc portion of the human IgG1 immunoglobulin. It is approved for the treatment of wet macular degeneration. The CAS number of Aflibercept is 862111-32-8. It has received a marketing authorization for the treatment of wet age-related macular degeneration, visual impairment due to diabetic macular oedema (DME) and diabetic retinopathy in patients with diabetic macular edema. The present commercial Aflibercept formulation contains sodium phosphate, sodium chloride, polysorbate 20, sucrose and water for injection and is supplied in a concentration of 40 mg/ml. In particular, it contains 40 mg/ml Aflibercept, 10 mM sodium phosphate buffer, 40 mM NaCl, 0.03% polysorbate 20, 5% sucrose; and water for injection. An alternative Aflibercept formulation may contain a histidine buffer, sodium chloride, polysorbate 20, sucrose and water for injection and is supplied in a concentration of 40 mg/ml. In particular, it contains 40 mg/ml Aflibercept, 10 mM histidine buffer, 40 mM NaCl, 0.03% polysorbate 20, 5% sucrose; and water for injection. The pH of the commercial and the alternative Aflibercept formulation may be adjusted to 6.2.

The antibody concentration within the pre-filled syringes of the present invention is typically 1-100 mg/ml, preferably 2-75 mg/ml, more preferably 3-50 mg/ml, even more preferably 5 to 30 mg/ml and most preferably 6 or 10 mg/ml. If Ranibizumab is contained within the pre-filled syringe of the present invention the Ranibizumab concentration is 10 mg/ml.

Aflibercept, marketed under the name Eylea®, is a recombinant fusion protein consisting of the VEGF binding portion from the extracellular domains of human VEGF receptors 1 and 2 that are fused to the Fc portion of the human IgG1 immunoglobulin. It is approved for the treatment of wet macular degeneration.

Ranibizumab, marketed under the name Lucentis®, is a Fab fragment of a humanized murine monoclonal antibody directed against VEGF and has been approved for the treatment of ocular diseases such as age-related macular degeneration and diabetic macular oedema.

In addition, the off-label use of the full-length antibody Bevacizumab (Avastin®), which is also directed against VEGF for the treatment of ocular diseases, is common.

Ranibizumab and Bevacizumab appear to have similar efficacy profiles in the treatment of neovascular age-related macular degeneration, although rare adverse events seem to occur more often with Bevacizumab (Johnson and Sharma (2013) Curr. Opin. Ophthalmol: 24(3):205-12).

The drug contained in the pre-filled syringe of the present invention, i.e. the VEGF-antagonist, preferably an anti-VEGF antibody, is stable at a temperature of 2 to 8° C. for at least six months, preferably for at least 9 months, more preferably for at least one year, particularly preferably for at least 18 months and most preferably for about two years. The drug contained in the pre-filled syringe of the present invention, i.e. the VEGF-antagonist, preferably an anti-VEGF antibody and more preferably Ranibizumab, is stable at room temperature, i.e. a temperature between 20° C. and 25° C., for at least three days or one week, preferably for at least two or three weeks, more preferably for about 4 weeks and most preferably for at least three months. The drug contained in the pre-filled syringe of the present invention, i.e. the VEGF-antagonist, preferably an anti-VEGF antibody or a VEGF receptor fusion protein and more preferably Ranibizumab or Aflibercept, is stable at a temperature of about 40° C., for at least four or six hours, preferably for at least 10 or 12 hours, more preferably for at least 18 or 24 hours and most preferably for one or two weeks.

The stability of the drug within the syringe can, for example, be determined by ion exchange chromatography, by which modifications of the drug such as oxidized and deamidated species can be detected or by size exclusion chromatography, by which aggregates of the drugs can be detected. A description of such an analysis is provided in the examples section.

The drug, i.e. the VEGF-antagonist, preferably the anti-VEGF antibody, is considered stable, if the sum of all impurities comprising aggregates and chemically modified species is less than 2%, preferably less than 1.5%, more preferably less than 1.2% and most preferably less than 1% compared to the amount of non-modified, non-aggregated drug.

The components of a pre-filled syringe are known to a skilled person and basically comprise a syringe barrel and a plunger.

The syringe barrel contains a defined volume of the liquid composition which can be expelled from the barrel through an outlet positioned on one end of the barrel when the plunger is pushed into and moves along the barrel. The syringe barrel typically has a substantially cylindrical shape. The outlet may comprise a projection from the outlet end through which extends a channel having a smaller diameter than the rest of the syringe barrel. The outlet may be adapted, for example by a luer lock type connection, (if no staked needle is used) for connection with a needle or other accessory such as a sealing device which is able to seal the barrel and can be removed to allow a needle to be attached to the syringe. This sealing can be achieved by the use of known sealing devices such as the OVSTM system of Vetter Pharma International GmbH. Staked needles are also available, either molded-in needles that are permanently incorporated when injection molding the syringe barrel or glued needles that are secured in a molded delivery passage of the syringe barrel.

Optionally in a pre-filled syringe the syringe outlet is firmly connected with a staked needle and does not need to be assembled prior to use. In this case, the risk of injuries with the needle during assembly of the syringe before injection is reduced. The staked needle can be attached to the pre-filled plastic syringe of the present invention without using an adhesive, since it can be molded into the syringe. In contrast, an adhesive is required to attach the needle to a glass syringe and can lead to impurities or increased protein oxidation (presentation of Adler at the 2011 PDA Europe The Universe of Pre-Filled Syringes and Injection Devices, Basel, 7-11 Nov. 2011; presentation of Markovic at the PDA Single Use Systems Workshop, Bethesda, 22-23 Jun. 2011).

For intravitreal administration, the needle size is typically 29, 291/2 or 30 gauge, although 31-, 32-, 33- and 34-gauge needles may also be used. The pre-filled syringe may be equipped with a passive needle safety guard to further avoid the danger of needle sticks after injection.

The syringe barrel is preferably tungsten-free, i.e. it does not contain any traces of tungsten, since it is not necessary to use tungsten in the syringe manufacturing process. Hence, there is no risk of tungsten-induced protein aggregation.

In one embodiment the syringe barrel comprises a mark such as a line printed on the syringe barrel which line allows the person injecting the liquid composition to align a pre-determined part of the closure (such as the tip of the front surface) or plunger with the mark. Thereby, any excess liquid composition and potential air bubbles are removed from the syringe barrel, allowing the safe administration of an exact predetermined dosage to the patient.

The plunger is pushed inside the syringe barrel, allowing the syringe to expel the liquid formulation through the outlet.

In a prefilled syringe the stopper is in contact with the liquid formulation. The stopper is typically made of an elastomeric material such as natural or synthetic rubber, which engages an inner surface of the syringe barrel to create a seal that facilitates ejecting the liquid formulation from the syringe when pressure is applied to the plunger.

In a preferred embodiment the plunger stopper is a non-retractable stopper, i.e. a stopper which is not mechanically connected to plunger rod. The term "non-retractable stopper" is intended to mean that the stopper can only be moved in the direction of the syringe outlet, but not in the opposite direction, i.e. to the rear part of the syringe. Hence, any risk for the contamination of the liquid composition within the syringe is minimized. Typically, a non-retractable stopper can be pushed by the plunger rod in the direction of the syringe outlet to expel the liquid formulation, but stays in its position when the plunger rod is retracted towards the rear end of the syringe.

The syringe has a nominal maximum fill volume, i.e. a volume which can be maximally taken up by the syringe, of 0.3 ml to 1.5 ml, preferably of 0.5 ml to 1.0 ml, most preferably 0.5 ml or 1.0 ml. For an injection volume of about 0.05 ml, a syringe having a nominal fill volume of 0.5 ml is preferred.

The volume of the liquid composition filled into the syringe is about 0.05 ml to about 1 ml, preferably about 0.1 ml to about 0.5 ml, more preferably 0.14 ml to 0.3 ml and most preferably 0.15 ml to 0.2 ml.

The skilled person knows that the syringe is usually filled with a volume which is larger than the volume actually administered to the patient to take into account any dead space within the syringe and the needle and the loss due to the preparation of the syringe for injection. Hence, the volume which is actually administered to the patient is between 0.01 ml and 1 ml, preferably between 0.02 and 0.5 ml, more preferably between 0.025 and 0.5 ml and most preferably between 0.03 ml and 0.05 ml.

Ranibizumab is typically administered in a volume of 0.05 ml with a Ranibizumab concentration of 6 or 10 mg/ml or in a volume of 0.03 ml or 0.05 ml with a Ranibizumab concentration of 10 mg/ml, yielding a delivered amount of 0.3 or 0.5 mg. For Aflibercept the administered volume is typically 0.05 ml with an Aflibercept concentration of 40 mg/ml, yielding a delivered amount of 2 mg. As discussed above, Bevacizumab is used off-label for the treatment of ocular diseases. In this case, the administered volume of Bevacizumab is 0.05 ml with a Bevacizumab concentration of 25 mg/ml, yielding a delivered amount of 1.25 mg.

Hence, in one embodiment the syringe is filled with a volume of the liquid composition of 0.15 ml to 0.2 ml and 0.03 ml to 0.05 ml of the liquid composition are administered to the patient.

The drug contained in the pre-filled syringe of the present invention, i.e. the VEGF-antagonist, preferably an anti-VEGF antibody or Aflibercept and more preferably Ranibizumab, retains its biological activity when stored at a temperature of 2 to 8° C. for at least six months, preferably for at least 9 months, more preferably for at least one year, particularly preferably for at least 18 months and most preferably for about two years. The drug contained in the pre-filled syringe of the present invention, i.e. the VEGF-antagonist, preferably an anti-VEGF antibody and more preferably Ranibizumab, retains its biological activity when stored at room temperature, i.e. a temperature between 20° C. and 25° C., for at least one hour, preferably for at least six hours, more preferably for at least twelve hours, and most preferably for about 24 hours.

The biological activity of the VEGF-antagonist, preferably an anti-VEGF antibody or Aflibercept and more preferably Ranibizumab, can be determined by incubating the antagonist which was stored under the conditions described above with human umbilical vein endothelial cells (HUVEC) and VEGF and measuring the VEGF-induced proliferation of the cells in the presence of the antagonist, i.e. by the CellTiter-Blue® Cell Viability Assay available from Promega, in comparison to cells not incubated with the antagonist. Since the VEGF-antagonist inhibits VEGF-induced signal transduction, the VEGF-induced proliferation will be reduced, if biologically active VEGF-antagonist is present in the sample.

The VEGF-antagonist, preferably the anti-VEGF antibody or Aflibercept and more preferably Ranibizumab retains its biological activity after storage in the pre-filled syringe, if the VEGF-induced proliferation is inhibited by at least 50%, preferably by at least 55% or 60%, more preferably by at least 65%, 70%, 75% or 80%, even more preferably by at least 85%, 87% or 90% and most preferably by at least 92%, 94%, 96%, 98% or 99%.

The pre-filled syringe may contain one or more pharmacologically active agents in addition to the VEGF antagonist. A pharmacologically active agent is able to exert a pharmacological effect when administered to a subject. Preferably, the additional pharmacologically active agent is a PDGF antagonist or an Ang2 antagonist. More preferably, the PDGF antagonist is an anti-PDGF antibody such as rinucumab or an aptamer such as E10030, marketed as Fovista®. Most preferably, the PDGF antagonist is E10030 which is described in Green et al. (1996) Biochemistry 35: 14413; U.S. Pat. Nos. 6,207,816; 5,731,144; 5,731,424; and 6,124,449. Also more preferably, the Ang2 antibody is an anti-Ang2 antibody and most preferably it is nesvacumab.

The liquid composition within the pre-filled syringe of the present invention has low particle content. In particular, it comprises less than 50 particles having a size of more than 10 µm after the syringe has been rotated at 40° C. for five minutes, two weeks or four weeks after three freeze-thaw cycles from +5° C. to −20° C. with 1° C. per minute, or after storage of the syringe at 5° C., 25° C. and 60% relative humidity or 40° C. and 75% relative humidity for three months. Alternatively or additionally, the liquid composition comprises less than 5 particles having a size of more than 25 µm after the syringe has been rotated at 40° C. for five minutes, two weeks or four weeks, or after three freeze-thaw cycles from +5° C. to −20° C. with 1° C. per minute, or after storage of the syringe at 5° C., 25° C./60% relative humidity or 40° C./75% relative humidity for three months. Hence, the pre-filled syringe meets the requirements of United States Pharmacopoeia <789> for ophthalmic solutions with respect to these particle sizes.

The pre-filled syringe of the present invention further has excellent gliding behaviour (breakout force and plunger sliding force). In particular, the breakout force, i.e. the force required to initiate the movement of the plunger, is less than 15N, 10N or 9N, preferably less than 8N or 7N, more preferably less than 6N and most preferably less than 5N. The breakout force does not change significantly, i.e. by more than 10%, when the syringe is stored for an extended period such as eight weeks. In contrast, in a syringe containing silicone the breakout force increases upon storage by at least twofold.

Further, the plunger sliding force, i.e. the force required to sustain the movement of the plunger along the syringe barrel to expel the liquid composition, is less than 15N, 10N, preferably less than 9N, more preferably less than 8N and most preferably less than 7N. In a particularly preferred embodiment there is no significant difference between the breakout force and the plunger sliding force.

The present invention also provides a kit comprising one or more of the pre-filled syringes of the present invention. Preferably, the kit comprises a blister pack. A "blister pack" has a cavity or pocket which is usually made from thermo-formed plastic and a backing of paperboard or a lidding seal of aluminum foil or plastic. The kit may further comprise a needle, if the pre-filled syringe does not comprise a staked-in needle. The kit may further comprise instructions for use. Preferably, the kit does not comprise an oxygen absorber which is typically used to reduce the level of oxygen within a package such as a blister pack. Oxygen absorbers usually contain a substance such as ferrous carbonate or ascorbate which substance reacts with any oxygen within a package with a high affinity, thereby reducing the oxygen content of the package.

Figure 2:
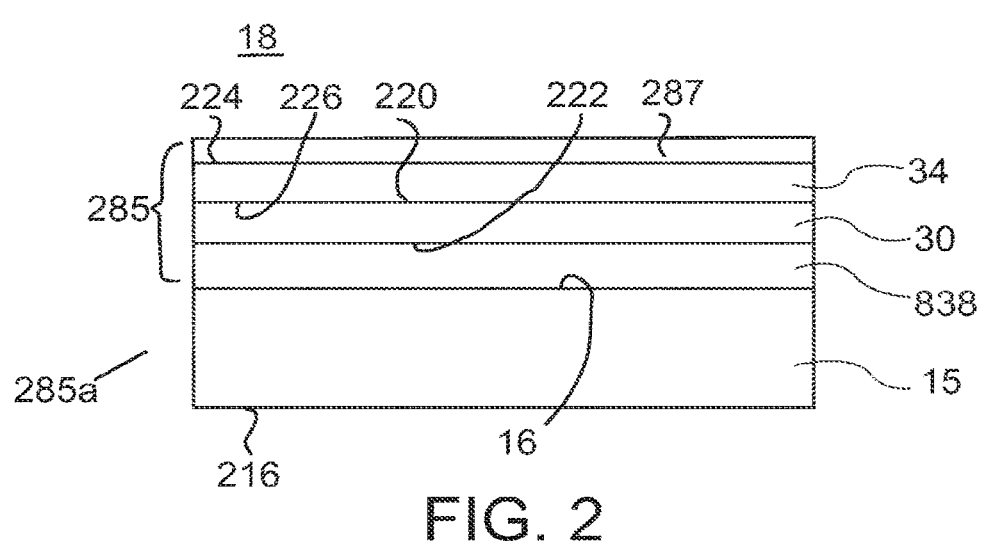
FIG. 2 is an enlarged detail view of the indicated portion of FIG. 1, showing an interior coating set.
Figure 3:
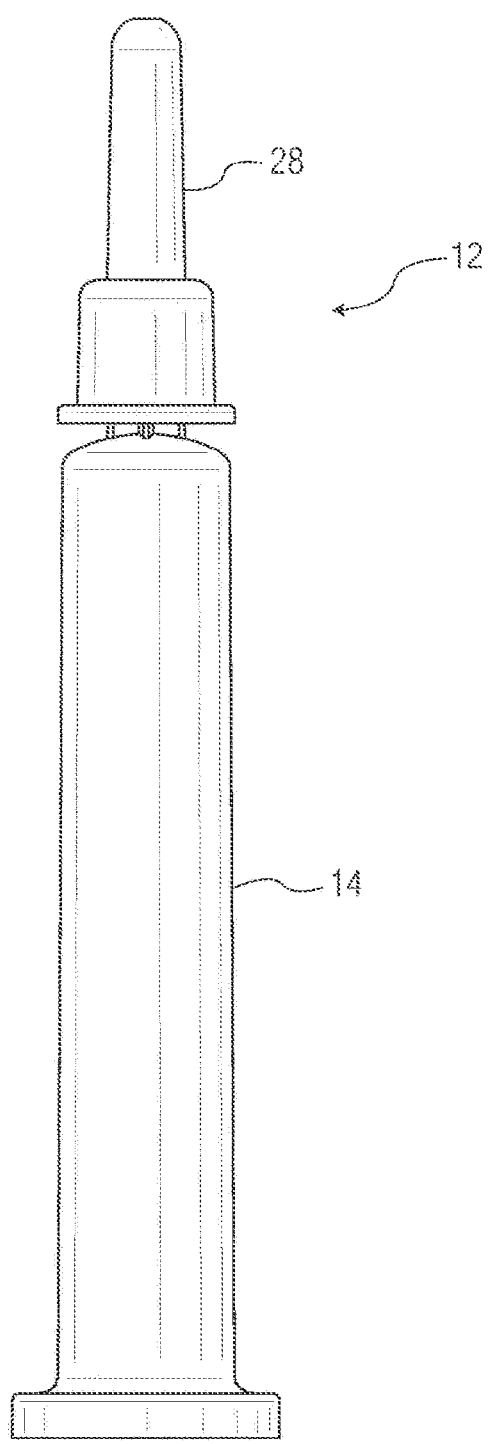
FIG. 3 is an elevation view of a capped assembly of a medical barrel, hypodermic needle, and cap, also known as a capped assembly, according to an embodiment of the disclosure.
Figure 4:
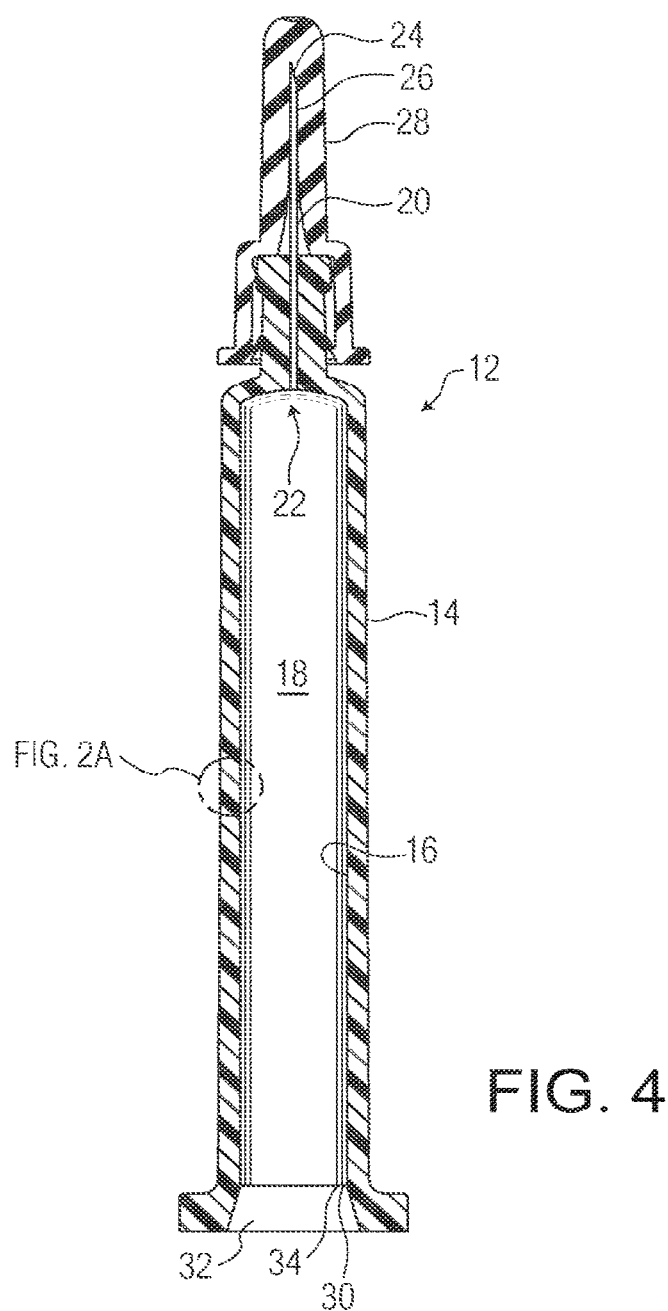
FIG. 4 is a longitudinal section of the capped assembly of FIG. 1, showing in an enlarged detail view, FIG. 4A, a trilayer PECVD set.
Figure 4A:
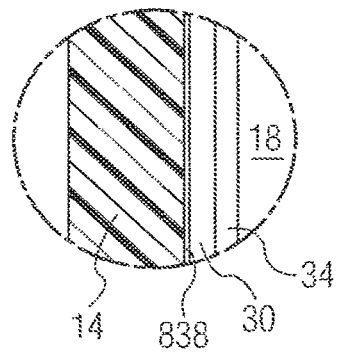

Referring to FIGS. 1 and 2, a vessel 214, here in the form of a disassembled pharmaceutical package 210 is shown. Several non-limiting examples of such pharmaceutical packages 210 or their parts are a syringe barrel, a vial, a cartridge, a bottle, a closure, a needle, a plunger, or a cap.

The pharmaceutical package 210 of FIGS. 1 and 2 has a lumen 18 defined at least in part by a wall 15. At least a portion of the wall 15 optionally comprises a thermoplastic material, optionally a cyclic olefin polymer. More generally, suitable materials for the wall 15 of the vessel 14 include a polyolefin (for example a cyclic olefin polymer, a cyclic olefin copolymer, or polypropylene), polyester, for example polyethylene terephthalate, a polycarbonate, or any combination or copolymer of any of these. A combination of any two or more of the materials in this paragraph can also be used.

The wall 15 has an interior surface 16 facing the lumen, an outer surface 216, and a vessel coating set 285 on at least a portion of the wall 15 facing the lumen 18. The interior surface 16 comprises a tie coating or layer 838, a barrier coating or layer 30, a pH protective coating or layer 34, and optionally a lubricity coating or layer 287. In this embodiment of the vessel coating set 285, the combination of the tie coating or layer 838, the barrier coating or layer 30, and the pH protective coating or layer 34 is sometimes known as a "trilayer coating" in which the barrier coating or layer 30 of $SiO_x$ optionally is protected against contents having a pH otherwise high enough to remove it by being sandwiched between the pH protective coating or layer 34 and the tie coating or layer 838, each an organic layer of $SiO_xC_y$ as defined in this specification.

FIGS. 1 and 2 show a vessel 14 having at least a single opening, and should be understood to include a vessel 14 having two or more openings, such as a syringe barrel.

Tie Coating or Layer

Referring to FIGS. 1 and 2, a tie coating or layer 838 is provided, sometimes referred to as an adhesion coating or layer. The tie coating or layer 838 optionally can be deposited by plasma enhanced chemical vapor deposition (PECVD) or other chemical vapor deposition processes on the vessel of a pharmaceutical package 210, for example a thermoplastic pharmaceutical package.

The tie coating or layer 838 optionally functions to improve adhesion of a barrier coating or layer 30 to a substrate such as the interior surface 16, in particular a thermoplastic substrate, although a tie coating or layer 838 can be used to improve adhesion to a glass substrate or to another coating or layer.

Optionally, the tie coating or layer 838 improves adhesion of the barrier coating or layer 30 to the substrate or wall 15. For example, the tie coating or layer 838 can be applied to the substrate and the barrier coating or layer 30 can be applied to the tie coating or layer 838 to improve adhesion of the barrier coating or layer 30 to the substrate. Optionally, the tie coating or layer 838 is also believed to relieve stress on the barrier coating or layer 30, making the barrier coating or layer 30 less subject to damage from thermal expansion or contraction or mechanical shock.

Optionally, the tie coating or layer 838 applied under a barrier coating or layer 30 can improve the function of a pH protective coating or layer 34 applied over the barrier coating or layer 30.

Optionally, the tie coating or layer 838 is also believed to decouple defects between the barrier coating or layer 30 and the thermoplastic substrate, here wall 15. This is believed to occur because any pinholes or other defects that may be formed when the tie coating or layer 838 is applied tend not to be continued when the barrier coating or layer 30 is applied, so the pinholes or other defects in one coating do not line up with defects in the other. Optionally, the tie coating or layer 838 has some efficacy as a barrier coating or layer 30, so even a defect providing a leakage path extending through the barrier coating or layer 30 is blocked by the tie coating or layer 838.

Optionally, the tie coating or layer 838 comprises $SiO_xC_y$, preferably can be composed of, comprise, or consist essentially of $SiO_xC_y$, wherein x is from about 0.5 to about 2.4 and y is from about 0.6 to about 3. The atomic ratios of Si, O, and C in the tie coating or layer 838 optionally can be:

Si 100: O 50-150: C 90-200 (i.e. x=0.5 to 1.5, y=0.9 to 2);
Si 100: O 70-130: C 90-200 (i.e. x=0.7 to 1.3, y=0.9 to 2)
Si 100: O 80-120: C 90-150 (i.e. x=0.8 to 1.2, y=0.9 to 1.5)
Si 100: O 90-120: C 90-140 (i.e. x=0.9 to 1.2, y=0.9 to 1.4), or
Si 100: O 92-107: C 116-133 (i.e. x=0.92 to 1.07, y=1.16 to 1.33).

The atomic ratio can be determined by XPS. Taking into account the H atoms, which are not measured by XPS, the tie coating or layer 838 may thus in one aspect have the formula $Si_wO_xC_yH_z$ (or its equivalent $SiO_xC_y$), for example where w is 1, x is from about 0.5 to about 2.4, y is from about 0.6 to about 3, and z is from about 2 to about 9. Typically, the tie coating or layer 838 would hence contain 36% to 41% carbon when normalized to 100% carbon plus oxygen plus silicon.

Optionally, the tie coating or layer 838 can be similar or identical in composition with the pH protective coating or layer 34 described elsewhere in this specification, although this is not a requirement.

Optionally, the tie coating or layer 838 is on average between 5 and 200 nm (nanometers), optionally between 5 and 100 nm, optionally between 5 and 20 nm thick. These thicknesses are not critical. Commonly but not necessarily, the tie coating or layer 838 will be relatively thin, since its function is to change the surface properties of the substrate.

The tie coating or layer 838 has an interior surface facing the lumen 18 and an outer surface facing the wall 15 interior surface 16. Optionally, the tie coating or layer 286 is at least coextensive with the barrier coating or layer. Optionally, the tie coating or layer is applied by PECVD, for example of a precursor feed comprising octamethylcyclotetrasiloxane (OMCTS), tetramethyldisiloxane (TMDSO), or hexamethyldisiloxane (HMDSO).

The thickness of the tie coating or layer 838 can be measured, for example, by transmission electron microscopy (TEM), and its composition can be measured by X-ray photoelectron spectroscopy (XPS).

Barrier Coating or Layer

Referring to FIGS. 1 and 2, a barrier coating or layer 30 optionally can be deposited by plasma enhanced chemical vapor deposition (PECVD) or other chemical vapor deposition processes on the vessel of a pharmaceutical package 210, for example a thermoplastic pharmaceutical package, to prevent oxygen, carbon dioxide, or other gases from entering the vessel, the barrier coating 288 optionally being effective to reduce the ingress of atmospheric gas into the lumen 210 compared to an uncoated pharmaceutical package 210, and/or to prevent leaching of the formulation 40 into or through the package wall, and to prevent sterilizing fluids such as hydrogen peroxide and ethylene oxide from permeating the thermoplastic wall and thus entering the lumen of the container.

The barrier coating or layer 30 optionally can be applied directly or indirectly to the thermoplastic wall 15 (for example the tie coating or layer 838 can be interposed between them) so that in the filled pharmaceutical package 210 the barrier coating or layer 30 is located between the inner or interior surface 16 of the wall 15 and the lumen 18 that is adapted to contain the formulation 40 to be stored. The barrier coating or layer 30 of $SiO_x$ is supported by the thermoplastic wall 15. The barrier coating or layer 30 as described elsewhere in this specification, or in U.S. Pat. No. 7,985,188, can be used in any embodiment.

The barrier coating or layer 30 optionally is characterized as an "$SiO_x$" coating, and contains silicon, oxygen, and optionally other elements, in which x, the ratio of oxygen to silicon atoms, is from about 1.5 to about 2.9, or 1.5 to about 2.6, or about 2. One suitable barrier composition is one where x is 2.3, for example.

Optionally, the barrier coating or layer 30 is from 2 to 1000 nm thick, optionally from 4 nm to 500 nm thick, optionally between 10 and 200 nm thick, optionally from 20 to 200 nm thick, optionally from 20 to 30 nm thick, and comprises $SiO_x$, wherein x is from 1.5 to 2.9. The barrier coating or layer 30 of $SiO_x$ has an interior surface 220 facing the lumen 18 and an outer surface 222 facing the interior surface of the tie coating or layer 838. For example, the barrier coating or layer 30 of any embodiment can be applied at a thickness of at least 2 nm, or at least 4 nm, or at least 7 nm, or at least 10 nm, or at least 20 nm, or at least 30 nm, or at least 40 nm, or at least 50 nm, or at least 100 nm, or at least 150 nm, or at least 200 nm, or at least 300 nm, or at least 400 nm, or at least 500 nm, or at least 600 nm, or at least 700 nm, or at least 800 nm, or at least 900 nm. The barrier coating or layer 30 can be up to 1000 nm, or at most 900 nm, or at most 800 nm, or at most 700 nm, or at most 600 nm, or at most 500 nm, or at most 400 nm, or at most 300 nm, or at most 200 nm, or at most 100 nm, or at most 90 nm, or at most 80 nm, or at most 70 nm, or at most 60 nm, or at most 50 nm, or at most 40 nm, or at most 30 nm, or at most 20 nm, or at most 10 nm, or at most 5 nm thick.

Ranges of from 4 nm to 500 nm thick, optionally from 7 nm to 400 nm thick, optionally from 10 nm to 300 nm thick, optionally from 20 nm to 200 nm thick, optionally from 20 to 30 nm thick, optionally from 30 nm to 100 nm thick are contemplated. Specific thickness ranges composed of any one of the minimum thicknesses expressed above, plus any equal or greater one of the maximum thicknesses expressed above, are expressly contemplated.

The thickness of the $SiO_x$ or other barrier coating or layer 30 can be measured, for example, by transmission electron microscopy (TEM), and its composition can be measured by X-ray photoelectron spectroscopy (XPS).

pH Protective Coating or Layer

Certain barrier coatings or layers 30 such as $SiO_x$ as defined here have been found to have the characteristic of being subject to being measurably diminished in barrier improvement factor in less than six months as a result of attack by certain relatively high pH contents of the coated vessel 14 as described elsewhere in this specification, particularly where the barrier coating or layer 30 directly contacts the formulation 40 or other contents. The inventors have found that a barrier coating or layer 30 of $SiO_x$ is eroded or dissolved by some fluids, for example aqueous compositions having a pH above about 5. Since coatings applied by chemical vapor deposition can be very thin—tens to hundreds of nanometers thick—a relatively slow rate of erosion can remove or reduce the effectiveness of the barrier coating or layer 30 in less time than the desired shelf life of a pharmaceutical package 214. This is particularly a problem for aqueous formulations 40, since many of them have a pH of roughly 7, or more broadly in the range of 4 to 8, alternatively from 5 to 9, similar to the pH of blood and other human or animal fluids. The higher the pH of the formulation 40, the more quickly it erodes or dissolves the SiO coating. Optionally, this problem can be addressed by protecting the barrier coating or layer 30, or other pH sensitive material, with a pH protective coating or layer 34.

The pH protective coating or layer 34 optionally provides protection of the underlying barrier coating or layer 30 against contents of the pharmaceutical package 210 having a pH from 4 to 8, including where a surfactant is present. For a pre-filled pharmaceutical package 210 that is in contact with the contents of the lumen 18 from the time it is manufactured to the time it is used, the pH protective coating or layer 34 optionally prevents or inhibits attack of the barrier coating or layer 30 sufficiently to maintain an effective oxygen barrier over the intended shelf life of the pre-filled pharmaceutical package 210. The rate of erosion, dissolution, or leaching (different names for related concepts) of the pH protective coating or layer 34, if directly contacted by a fluid, is less than the rate of erosion of the barrier coating or layer 30, if directly contacted by the fluid having a pH of from 5 to 9. The pH protective coating or layer 34 is effective to isolate a formulation 40 having a pH between 5 and 9 from the barrier coating or layer 30, at least for sufficient time to allow the barrier coating or layer 30 to act as a barrier during the shelf life of the pre-filled pharmaceutical package 210.

The inventors have further found that certain pH protective coatings or layers 34 of $SiO_xC_y$, formed from polysiloxane precursors, which pH protective coatings or layers 34 have a substantial organic component, do not erode quickly when exposed to fluids, and in fact erode or dissolve more slowly when the fluids have pHs within the range of 4 to 8 or 5 to 9. For example, at pH 8, the dissolution rate of a pH protective coating or layer 34 is quite slow. These pH protective coatings or layers 34 of $SiO_xC_y$ can therefore be used to cover a barrier coating or layer 30 of $SiO_x$, retaining the benefits of the barrier coating or layer 30 by protecting it from the formulation 40 in the pharmaceutical package 210. The pH protective coating or layer 34 is applied over at least a portion of the $SiO_x$ barrier coating or layer 30 to protect the barrier coating or layer 30 from contents stored in a pharmaceutical package 210, where the contents otherwise would be in contact with the barrier coating or layer 30 of $SiO_x$.

Effective pH protective coatings or layers 34 for avoiding erosion can be made from siloxanes as described in this disclosure. $SiO_xC_y$ coatings can be deposited from cyclic siloxane precursors, for example octamethylcyclotetrasiloxane (OMCTS), or linear siloxane precursors, for example hexamethyldisiloxane (HMDSO) or tetramethyldisiloxane (TMDSO).

The pH protective coating or layer 34 optionally is effective to keep the barrier coating or layer 30 at least substantially undissolved as a result of attack by the formulation 40 for a period of at least six months.

The pH protective coating or layer 34 optionally can prevent or reduce the precipitation of a compound or component of a formulation 40 (for example, polypeptides such as proteins, natural or synthetic DNA, and the like) in contact with the pH protective coating or layer 34, in comparison to the uncoated surface and/or to a barrier coated surface using HMDSO as precursor.

Referring to FIGS. 1 and 2, the pH protective coating or layer 34 can be composed of, comprise, or consist essentially of $Si_wO_xC_yH_z$ (or its equivalent $SiO_xC_y$), each as defined wherein x is from about 0.5 to about 2.4 and y is from about 0.6 to about 3. The atomic ratios of Si, O, and C in the pH protective coating or layer 34 optionally can be:

Si 100: O 50-150: C 90-200 (i.e. x=0.5 to 1.5, y=0.9 to 2);

Si 100: O 70-130: C 90-200 (i.e. x=0.7 to 1.3, y=0.9 to 2)

Si 100: O 80-120: C 90-150 (i.e. x=0.8 to 1.2, y=0.9 to 1.5)

Si 100: O 90-120: C 90-140 (i.e. x=0.9 to 1.2, y=0.9 to 1.4), or

Si 100: O 92-107: C 116-133 (i.e. x=0.92 to 1.07, y=1.16 to 1.33) or

Si 100: O 80-130: C 90-150.

Alternatively, the pH protective coating or layer 34 can have atomic concentrations normalized to 100% carbon, oxygen, and silicon, as determined by X-ray photoelectron spectroscopy (XPS), of less than 50% carbon and more than 25% silicon. Alternatively, the atomic concentrations are from 25 to 45% carbon, 25 to 65% silicon, and 10 to 35% oxygen. Alternatively, the atomic concentrations are from 30 to 40% carbon, 32 to 52% silicon, and 20 to 27% oxygen. Alternatively, the atomic concentrations are from 33 to 37% carbon, 37 to 47% silicon, and 22 to 26% oxygen.

Optionally, the atomic concentration of carbon in the pH protective coating or layer 34, normalized to 100% of carbon, oxygen, and silicon, as determined by X-ray photoelectron spectroscopy (XPS), can be greater than the atomic concentration of carbon in the atomic formula for the organosilicon precursor. For example, embodiments are contemplated in which the atomic concentration of carbon increases by from 1 to 80 atomic percent, alternatively from 10 to 70 atomic percent, alternatively from 20 to 60 atomic percent, alternatively from 30 to 50 atomic percent, alternatively from 35 to 45 atomic percent, alternatively from 37 to 41 atomic percent.

Optionally, the atomic ratio of carbon to oxygen in the pH protective coating or layer 34 can be increased in comparison to the organosilicon precursor, and/or the atomic ratio of oxygen to silicon can be decreased in comparison to the organosilicon precursor.

Optionally, the pH protective coating or layer 34 can have an atomic concentration of silicon, normalized to 100% of carbon, oxygen, and silicon, as determined by X-ray photoelectron spectroscopy (XPS), less than the atomic concentration of silicon in the atomic formula for the feed gas. For example, embodiments are contemplated in which the atomic concentration of silicon decreases by from 1 to 80 atomic percent, alternatively by from 10 to 70 atomic percent, alternatively by from 20 to 60 atomic percent, alternatively by from 30 to 55 atomic percent, alternatively by from 40 to 50 atomic percent, alternatively by from 42 to 46 atomic percent.

As another option, a pH protective coating or layer 34 is contemplated in any embodiment that can be characterized by a sum formula wherein the atomic ratio C:O can be increased and/or the atomic ratio Si:O can be decreased in comparison to the sum formula of the organosilicon precursor.

The atomic ratio of Si:O: C can be determined by XPS (X-ray photoelectron spectroscopy). Taking into account the H atoms, the pH protective coating or layer 34 may thus in one aspect have the formula $Si_wO_xC_yH_z$, or its equivalent $SiO_xC_y$, for example where w is 1, x is from about 0.5 to about 2.4, y is from about 0.6 to about 3, and z is from about 2 to about 9.

The thickness of the pH protective coating or layer 34 as applied optionally is between 10 and 1000 nm; alternatively from 10 nm to 900 nm; alternatively from 10 nm to 800 nm; alternatively from 10 nm to 700 nm; alternatively from 10 nm to 600 nm; alternatively from 10 nm to 500 nm; alternatively from 10 nm to 400 nm; alternatively from 10 nm to 300 nm; alternatively from 10 nm to 200 nm; alternatively from 10 nm to 100 nm; alternatively from 10 nm to 50 nm; alternatively from 20 nm to 1000 nm; alternatively from 50 nm to 1000 nm; alternatively from 50 nm to 800 nm; optionally from 50 to 500 nm; optionally from 100 to 200 nm; alternatively from 100 nm to 700 nm; alternatively from 100 nm to 200 nm; alternatively from 300 to 600 nm. The thickness does not need to be uniform throughout the vessel, and will typically vary from the preferred values in portions of a vessel.

The pH protective coating or layer 34 can have a density between 1.25 and 1.65 g/cm³, alternatively between 1.35 and 1.55 g/cm³, alternatively between 1.4 and 1.5 g/cm³, alternatively between 1.4 and 1.5 g/cm³, alternatively between 1.44 and 1.48 g/cm³, as determined by X-ray reflectivity (XRR).

The pH protective coating or layer 34 optionally can have an RMS surface roughness value (measured by AFM) of from about 5 to about 9, optionally from about 6 to about 8, optionally from about 6.4 to about 7.8. The $R_a$ surface roughness value of the pH protective coating or layer 34, measured by AFM, can be from about 4 to about 6, optionally from about 4.6 to about 5.8. The $R_{max}$ surface roughness value of the pH protective coating or layer 34, measured by AFM, can be from about 70 to about 160, optionally from about 84 to about 142, optionally from about 90 to about 130.

The interior surface of the pH protective optionally can have a contact angle (with distilled water) of from 90° to 110°, optionally from 80° to 120°, optionally from 70° to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement."

Optionally an FTIR absorbance spectrum of the pH protective coating or layer 34 of any embodiment has a ratio greater than 0.75 between the maximum amplitude of the Si—O—Si symmetrical stretch peak normally located between about 1000 and 1040 cm–1, and the maximum amplitude of the Si—O—Si asymmetric stretch peak normally located between about 1060 and about 1100 cm–1. Alternatively in any embodiment, this ratio can be at least 0.8, or at least 0.9, or at least 1.0, or at least 1.1, or at least 1.2. Alternatively in any embodiment, this ratio can be at most 1.7, or at most 1.6, or at most 1.5, or at most 1.4, or at most 1.3. Any minimum ratio stated here can be combined with any maximum ratio stated here, as an alternative embodiment of the invention of FIGS. 1-5.

Optionally, in any embodiment the pH protective coating or layer 34, in the absence of the medicament, has a non-oily appearance. This appearance has been observed in some instances to distinguish an effective pH protective coating or layer 34 from a lubricity layer, which in some instances has been observed to have an oily (i.e. shiny) appearance.

Optionally, for the pH protective coating or layer 34 in any embodiment, the silicon dissolution rate by a 50 mM potassium phosphate buffer diluted in water for injection, adjusted to pH 8 with concentrated nitric acid, and containing 0.2 wt. % polysorbate-80 surfactant, (measured in the absence of the medicament, to avoid changing the dissolution reagent), at 40° C., is less than 170 ppb/day. (Polysorbate-80 is a common ingredient of pharmaceutical formulations, and is available for example as Tween®-80 from Uniqema Americas LLC, Wilmington Del.)

Optionally, for the pH protective coating or layer 34 in any embodiment, the silicon dissolution rate upon dissolution into a test composition with a pH of 8 from the vessel, is less than 160 ppb/day, or less than 140 ppb/day, or less than 120 ppb/day, or less than 100 ppb/day, or less than 90 ppb/day, or less than 80 ppb/day. Optionally, in any embodiment the silicon dissolution rate is more than 10 ppb/day, or more than 20 ppb/day, or more than 30 ppb/day, or more than 40 ppb/day, or more than 50 ppb/day, or more than 60 ppb/day. Any minimum rate stated here can be combined with any maximum rate stated here for the pH protective coating or layer 34 in any embodiment.

Optionally in any embodiment the total silicon content of the pH protective coating or layer 34 and barrier coating, upon dissolution into a test composition with a pH of 8 from the vessel, is less than 66 ppm, or less than 60 ppm, or less than 50 ppm, or less than 40 ppm, or less than 30 ppm, or less than 20 ppm.

The pH protective coating or layer 34 has an interior surface 224 facing the lumen 18 and an outer surface 226 facing the interior surface of the barrier coating or layer 30. Optionally, the pH protective coating or layer 34 is at least coextensive with the barrier coating or layer 30. The pH protective coating or layer 34 alternatively can be less extensive than the barrier coating, as when the formulation 40 does not contact or seldom is in contact with certain parts of the barrier coating or layer 30. The pH protective coating or layer 34 alternatively can be more extensive than the barrier coating, as it can cover areas that are not provided with a barrier coating.

The pH protective coating or layer 34 optionally can be applied by plasma enhanced chemical vapor deposition (PECVD) of a precursor feed comprising an acyclic siloxane, a monocyclic siloxane, a polycyclic siloxane, a polysilsesquioxane, a silatrane, a silquasilatrane, a silproatrane, or a combination of any two or more of these precursors. Some particular, non-limiting precursors contemplated for such use include octamethylcyclotetrasiloxane (OMCTS), HMDSO, or TMDSO.

Optionally, an FTIR absorbance spectrum of the pH protective coating or layer 34 has a ratio greater than 0.75 between the maximum amplitude of the Si—O—Si symmetrical stretch peak between about 1000 and 1040 $cm^{-1}$, and the maximum amplitude of the Si—O—Si asymmetric stretch peak between about 1060 and about 1100 $cm^{-1}$.

In the presence of a fluid composition having a pH between 5 and 9, optionally with a pH of 8 in the vessel, contained in the lumen 18, the calculated shelf life of the pharmaceutical package 210 is more than six months at a storage temperature of 4° C. Optionally, the rate of erosion of the pH protective coating or layer 34, if directly contacted by a fluid composition having a pH of 8, is less than 20% optionally less than 15%, optionally less than 10%, optionally less than 7%, optionally from 5% to 20%, optionally 5% to 15%, optionally 5% to 10%, optionally 5% to 7%, of the rate of erosion of the barrier coating or layer 30, if directly contacted by the same fluid composition under the same conditions. Optionally, the fluid composition removes the pH protective coating or layer 34 at a rate of 1 nm or less of pH protective coating or layer 34 thickness per 44 hours of contact with the fluid composition.

Optionally, the silicon dissolution rate of the pH protective coating or layer 34 and barrier coating or layer 30 by a 50 mM potassium phosphate buffer diluted in water for injection, adjusted to pH 8 with concentrated nitric acid, and containing 0.2 wt. % polysorbate-80 surfactant from the vessel is less than 170 parts per billion (ppb)/day.

Optionally, the total silicon content of the pH protective coating or layer 34 and the barrier coating or layer 30, upon dissolution into 0.1 N potassium hydroxide aqueous solution at 40° C. from the vessel, is less than 66 ppm.

Optionally, the calculated shelf life of the pharmaceutical package 210 (total Si/Si dissolution rate) is more than 2 years.

Optionally, the pH protective coating or layer 34 shows an O-Parameter measured with attenuated total reflection (ATR) FTIR of less than 0.4, measured as:

$$O\text{-Parameter} = \frac{\text{Intensity at 1253 cm}^{-1}}{\text{Maximum intensity in the range 1000 to 1100 cm}^{-1}}.$$

The O-Parameter is defined in U.S. Pat. No. 8,067,070, which claims an O-parameter value of most broadly from 0.4 to 0.9. It can be measured from physical analysis of an FTIR amplitude versus wave number plot to find the numerator and denominator of the above expression, for example on the plot shown as FIG. 5 of U.S. Pat. No. 8,067,070, except annotated to show interpolation of the wave number and absorbance scales to arrive at an absorbance at 1253 cm−1 of 0.0424 and a maximum absorbance at 1000 to 1100 cm−1 of 0.08, resulting in a calculated O-parameter of 0.53. The O-Parameter can also be measured from digital wave number versus absorbance data.

U.S. Pat. No. 8,067,070 asserts that the claimed O-parameter range provides a superior passivation coating. Surprisingly, it has been found by the present inventors that 0-parameters outside the ranges claimed in U.S. Pat. No. 8,067,070 provide better results than are obtained in U.S. Pat. No. 8,067,070. Alternatively in the embodiment of FIGS. 1-5, the O-parameter has a value of from 0.1 to 0.39, or from 0.15 to 0.37, or from 0.17 to 0.35.

Optionally, the pH protective coating or layer 34 shows an N-Parameter measured with attenuated total reflection (ATR) of less than 0.7, measured as:

$$N\text{-Parameter} = \frac{\text{Intensity at 840 cm}^{-1}}{\text{Intensity at 799 cm}^{-1}}.$$

The N-Parameter is also described in U.S. Pat. No. 8,067,070, and is measured analogously to the O-Parameter except that intensities at two specific wave numbers are used—neither of these wave numbers is a range. U.S. Pat. No. 8,067,070 claims a passivation layer with an N-Parameter of 0.7 to 1.6. Again, the present inventors have made better coatings employing a pH protective coating or layer 34 having an N-Parameter lower than 0.7, as described above. Alternatively, the N-parameter has a value of at least 0.3, or from 0.4 to 0.6, or at least 0.53.

The protective coating or layer of $Si_wO_xC_y$, or its equivalent $SiO_xC_y$, also can have utility as a hydrophobic layer, independent of whether it also functions as a pH protective coating or layer 34. Suitable hydrophobic coatings or layers and their application, properties, and use are described in U.S. Pat. No. 7,985,188. Dual functional protective/hydrophobic coatings or layers having the properties of both types of coatings or layers can be provided for any embodiment of the present invention.

Lubricity Coating or Layer

Referring to the drawings, a method for preparing a lubricity coating or layer 287 on a plastic substrate such as the interior surface 16 of a pharmaceutical package 210, for example on its wall 15, is illustrated. When a vessel 14 is coated by the above coating method using PECVD, the coating method comprises several steps. A vessel 14 is provided having an open end, a closed end, and an interior surface. At least one gaseous reactant is introduced within the vessel 14. Plasma is formed within the vessel 14 under conditions effective to form a reaction product of the reactant, i.e. a coating, on the interior surface of the vessel 14.

Apparatus and general conditions suitable for carrying out this method are described in U.S. Pat. No. 7,985,188, which is incorporated here by reference in full.

The method includes providing a gas including an organosilicon precursor, optionally an oxidizing gas (for example O2), and an inert gas in the vicinity of the substrate surface. The inert gas optionally is a noble gas, for example argon, helium, krypton, xenon, neon, or a combination of two or more of these inert gases. Plasma is generated in the gas by providing plasma-forming energy adjacent to the plastic substrate. As a result, a lubricity coating or layer 287 is formed on the substrate surface such as 16 by plasma enhanced chemical vapor deposition (PECVD). Optionally, the plasma-forming energy is applied in a first phase as a first pulse at a first energy level, followed by further treatment in a second phase at a second energy level lower than the first energy level. Optionally, the second phase is applied as a second pulse.

A gaseous reactant or process gas can be employed having a standard volume ratio of, for example when a lubricity coating is prepared: from 1 to 6 standard volumes, optionally from 2 to 4 standard volumes, optionally equal to or less than 6 standard volumes, optionally equal to or less than 2.5 standard volumes, optionally equal to or less than 1.5 standard volumes, optionally equal to or less than 1.25 standard volumes of the precursor; from 1 to 100 standard volumes, optionally from 5 to 100 standard volumes, optionally from 10 to 70 standard volumes, of a carrier gas; from 0.1 to 2 standard volumes, optionally from 0.2 to 1.5 standard volumes, optionally from 0.2 to 1 standard volumes, optionally from 0.5 to 1.5 standard volumes, optionally from 0.8 to 1.2 standard volumes of an oxidizing agent.

First Phase of Plasma Forming Energy

In any embodiment, the plasma optionally can be generated with microwave energy or RF energy. The plasma optionally can be generated with electrodes powered at a radio frequency, preferably at a frequency of from 10 kHz to less than 300 MHz, more preferably of from 1 to 50 MHz, even more preferably of from 10 to 15 MHz, most preferably at 13.56 MHz.

In any embodiment, the first pulse energy can be, for example, from 21 to 100 Watts, alternatively from 25 to 75 Watts; alternatively from 40 to 60 Watts.

In any embodiment, the ratio of the electrode power to the plasma volume for the first pulse optionally can be equal to or more than 5 W/ml, preferably is from 6 W/ml to 150

W/ml, more preferably is from 7 W/ml to 100 W/ml, most preferably from 7 W/ml to 20 W/ml.

In any embodiment, the first pulse optionally can be applied for 0.1 to 5 seconds, alternatively 0.5 to 3 seconds, alternatively 0.75 to 1.5 seconds. The first phase energy level optionally can be applied in at least two pulses. The second pulse is at a lower energy level than the first pulse. As a further option, the first phase energy level optionally can be applied in at least three pulses. The third pulse optionally can be at a lower energy level than the second pulse.

Second Phase of Plasma Forming Energy

In any embodiment, the second phase energy level optionally can be from 0.1 to 25 Watts, alternatively from 1 to 10 Watts, alternatively from 2 to 5 Watts.

Relation Between First and Second Phases

In any embodiment, the plasma-forming energy optionally can be applied in the first phase as a first pulse at a first energy level, followed by further treatment in a second phase at a second energy level.

Lubricity Profile

The lubricity coating optionally provides a consistent plunger force that reduces the difference between the break loose force (Fi) and the glide force (Fm). These two forces are important performance measures for the effectiveness of a lubricity coating. For Fi and Fm, it is desired to have a low, but not too low value. With too low Fi, which means a too low level of resistance (the extreme being zero), premature/unintended flow may occur, which might e.g. lead to an unintentional premature or uncontrolled discharge of the content of a prefilled syringe.

Further advantageous Fi and Fm values can be found in the Tables of the Examples. Lower Fi and Fm values can be achieved than the ranges indicated above. Coatings having such lower values are also considered to be encompassed by the present invention.

Break-loose and glide forces are important throughout a device's shelf life especially in automated devices such as auto-injectors. Changes in break-loose and/or glide forces can lead to misfiring of auto injectors.

The vessels (e.g. syringe barrels and/or plungers) coated with a lubricity coating according to present invention have a higher lubricity, which means a lower Fi and/or Fm (determined, e.g. by measuring the Fi and/or Fm) than the uncoated vessels. They also have a higher lubricity than vessels coated with an SiOx coating as described herein at the external surface.

Another aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of carbon, normalized to 100% of carbon, oxygen, and silicon, as determined by X-ray photoelectron spectroscopy (XPS), greater than the atomic concentration of carbon in the atomic formula for the feed gas.

Optionally, the atomic concentration of carbon increases by from 1 to 80 atomic percent (as calculated and based on the XPS conditions in Example 15 of EP 2 251 455), alternatively from 10 to 70 atomic percent, alternatively from 20 to 60 atomic percent, alternatively from 30 to 50 atomic percent, alternatively from 35 to 45 atomic percent, alternatively from 37 to 41 atomic percent in relation to the atomic concentration of carbon in the organosilicon precursor when a lubricity coating is made.

An additional aspect of the invention is a lubricity layer or coating deposited by PECVD from a feed gas comprising a monocyclic siloxane, a monocyclic silazane, a polycyclic siloxane, a polycyclic silazane, or any combination of two or more of these. The coating has an atomic concentration of silicon, normalized to 100% of carbon, oxygen, and silicon, as determined by X-ray photoelectron spectroscopy (XPS), less than the atomic concentration of silicon in the atomic formula for the feed gas. See Example 15 of EP 2 251 455.

Optionally, the atomic concentration of silicon decreases by from 1 to 80 atomic percent (as calculated and based on the XPS conditions in Example 15 of EP 2251 455), alternatively from 10 to 70 atomic percent, alternatively from 20 to 60 atomic percent, alternatively from 30 to 55 atomic percent, alternatively from 40 to 50 atomic percent, alternatively from 42 to 46 atomic percent.

The lubricity coating can have a density between 1.25 and 1.65 g/cm.sup.3, alternatively between 1.35 and 1.55 g/cm.sup.3, alternatively between 1.4 and 1.5 g/cm.sup.3, alternatively between 1.4 and 1.5 g/cm.sup.3, alternatively between 1.44 and 1.48 g/cm.sup.3, as determined by X-ray reflectivity (XRR).

Other types of lubricity coatings or layers 287 are also contemplated as alternatives to the plasma-applied SiOxCyHz coatings or layers just described in the illustrated embodiments. One example is a fluorinated polymer, for example polytetrafluoroethylene (PTFE), coating, and another is a crosslinked fluorinated polymer, e.g. perfluoropolyether (PFPE), or polysiloxane coating, e.g. crosslinked silicone oil.

The fluorinated polymer coating can be applied, for example, using a fluorinated precursor, by chemically modifying the precursor while on or in the vicinity of the fluid receiving interior surface.

Optionally, the precursor comprises: dimeric tetrafluoroparaxylylene; difluorocarbene; monomeric tetrafluoroethylene; oligomeric tetrafluoroethylene having the formula $F_2C=CF(CF_2)_xF$ in which x is from 1 to 100, optionally 2 to 50, optionally 2-20, optionally 2-10; sodium chlorodifluoroacetate; chlorodifluoromethane; bromodifluoromethane; hexafluoropropylene oxide; 1H,1H,2H,2H-perfluorodecyl acrylate (FDA); a bromofluoroalkane in which the alkane moiety has from 1 to 6 carbon atoms; an iodofluoroalkane in which the alkane moiety has from 1 to 6 carbon atoms; or a combination of any two or more of these.

The fluorinated polymer is: optionally from at least 0.01 micrometer to at most 100 micrometers thick; optionally from at least 0.05 micrometers to at most 90 micrometers thick; optionally from at least 0.1 micrometers to at most 80 micrometers thick; optionally from at least 0.1 micrometers to at most 70 micrometers thick; optionally from at least 0.1 micrometers to at most 60 micrometers thick; optionally from at least 0.1 micrometers to at most 50 micrometers thick; optionally from at least 0.1 micrometers to at most 40 micrometers thick; optionally from at least 0.1 micrometers to at most 30 micrometers thick; optionally from at least 0.1 micrometers to at most 20 micrometers thick; optionally from at least 0.1 micrometers to at most 15 micrometers thick; optionally from at least 0.1 micrometers to at most 12 micrometers thick; optionally from at least 0.1 micrometers to at most 10 micrometers thick; optionally from at least 0.1 micrometers to at most 8 micrometers thick; optionally from at least 0.1 micrometers to at most 6 micrometers thick; optionally from at least 0.1 micrometers to at most 4 micrometers thick; optionally from at least 0.1 micrometers to at most 2 micrometers thick; optionally from at least 0.1 micrometers to at most 1 micrometers thick; optionally from at least 0.1 micrometers to at most 0.9 micrometers thick; optionally from at least 0.1 micrometers to at most 0.8 micrometers thick; optionally from at least 0.1 micrometers to at most 0.7 micrometers thick; optionally from at least 0.1 micrometers to at most 0.6 micrometers thick; optionally from at least 0.1 micrometers to at most 0.5 micrometers thick; optionally from at least 0.5 micrometers to at most 5 micrometers thick; optionally from at least 0.5 micrometers to at most 4 micrometers thick; optionally from at least 0.5 micrometers to at most 3 micrometers thick; optionally from at least 0.5 micrometers to at most 2 micrometers thick; optionally from at least 0.5 micrometers to at most 1 micrometer thick; optionally about 10 micrometers thick; optionally about 2 micrometers thick.

The fluorinated polymer optionally can be applied by vapor deposition, for example chemical vapor deposition. Optionally, the fluorinated polymer can be applied by chemical vapor deposition of dimeric tetrafluoroparaxylylene. An example of a suitable fluorinated polymer is polytetrafluoroparaxylylene. Optionally, the fluorinated polymer consists essentially of polytetrafluoroparaxylylene.

Optionally in any embodiment, the fluorinated polymer coating or layer comprises polytetrafluoroethylene. Optionally in any embodiment, the fluorinated polymer coating or layer consists essentially of polytetrafluoroethylene.

For example, in any embodiment, the fluorinated polymer coating or layer can be applied by chemically modifying a precursor, while on or in the vicinity of the fluid receiving interior surface, to produce the fluorinated polymer coating or layer on the fluid receiving interior surface. Optionally in any embodiment, the fluorinated polymer coating or layer is applied by chemical vapor deposition. For one example, in any embodiment, the fluorinated polymer coating or layer can be applied by heated wire chemical vapor deposition (HWCVD). For another example, in any embodiment, the fluorinated polymer coating or layer can be applied by plasma enhanced chemical vapor deposition (PECVD). Mixed processes or other processes for applying a suitable coating are also contemplated, in any embodiment.

Another example of a suitable HWCVD process for applying the fluorinated polymer coating is the process described in Hilton G. Pryce Lewis, Neeta P. Bansal, Aleksandr J. White, Erik S. Handy, HWCVD of Polymers: Commercialization and Scale-up, THIN SOLID FILMS 517 (2009) 3551-3554; and US Publ. Appl. 2012/0003497 A1, published Jan. 5, 2012, which are incorporated here by reference in their entirety for their description of fluorinated polymer coatings and their application.

Optionally in any embodiment, the precursor comprises Parylene N or poly(paraxylylene); Parylene C or poly(2-chloroparaxylylene); Parylene D or poly(2,5-dichloroparaxylylene); Parylene HT® or poly(tetrafluoropara-xylylene), or their dimers, or a combination of two or more of these. Parylenes can be applied to a substrate as described by Specialty Coating Systems, Inc., discussed for example in Lonny Wolgemuth, Challenges With Prefilled Syringes: The Parylene Solution, www.ongrugdelivery.com, pp. 44-45 (Frederick Furness Publishing, 2012). The documents mentioned in this paragraph are incorporated by reference here.

The crosslinked perfluoropolyether (PFPE) or polysiloxane coating 287 can be applied, for example, by applying a liquid perfluoropolyether (PFPE) or polysiloxane to a surface, then treating it by exposing it to an energy source. An optional additional step comprises exposing the surface to an energy source, specifically an ionizing gas plasma at about atmospheric pressure, prior to the application of the lubricant. As a result of these methods, the lubricant resists migrating from the surface, thereby reducing the break-out force and sliding frictional force and reducing the introduction of the lubricant into the contents of a prefilled syringe thus lubricated.

The lubricant can be applied to the surface of the object by any of the numerous methods know in the art. By way of example, suitable application methods include spraying, atomizing, spin casting, painting, dipping, wiping, tumbling, and ultrasonics. The method used to apply the lubricant is not limited. The lubricant may be a fluorochemical compound or a polysiloxane-based compound.

The energy source can be an ionizing gas plasma. The gas may be a noble gas including, for example, helium, neon, argon, and krypton. Alternatively, the gas may be an oxidative gas including, for example, air, oxygen, carbon dioxide, carbon monoxide, and water vapor. In yet another alternative, the gas may be a non-oxidative gas including, for example, nitrogen and hydrogen. Mixtures of any of these gases may also be used.

The exact parameters under which the ionizing gas plasma are generated are not critical These parameters are selected based on factors including, for example, the gas in which the plasma is to be generated, the electrode geometry, frequency of the power source, and the dimensions of the surface to be treated. The treatment time may range from about 0.001 second to about 10 minutes, in addition ranging from about 0.001 second to about 5 minutes, and further in addition ranging from about 0.01 second to about 1 minute. The frequency may range from about 60 hertz to about 2.6 gigahertz, in addition ranging from about 1 kilohertz to about 100 kilohertz, and further in addition ranging from about 3 kilohertz to about 10 kilohertz. The power setting may be less than or equal to, for example, about 10 kilowatt.

The lubricant-coated surface also or instead can be exposed to ionizing radiation which provides the energy necessary to treat the lubricant. The ionizing radiation source can be gamma radiation or electron-beam radiation. Typically, commercial gamma irradiation processing systems use cobalt-60 as the gamma radiation source, although cesium-137 or other gamma radiation source may also be used. Commercial electron-beam radiation systems generate electrons from an electricity source using an electron gun assembly, accelerate the electrons, then focus the electrons into a beam. This beam of electrons is then directed at the material to be treated. The lubricant-coated surface may be exposed to an ionizing radiation dosage ranging from about 0.1 megarad to about 20 megarads, in addition ranging from about 0.5 megarad to about 15 megarads, and further in addition ranging from about 1 megarad to about 10 megarads.

The above and further details regarding the above process and the resulting lubricity coating or layer 287 are disclosed in U.S. Publ. Appl. 20040231926 A1, Sakhrani, et al., which is incorporated here by reference.

Lubricity coatings or layers or hydrophobic coatings or layers can be applied as described in U.S. Pat. No. 7,985, 188.

Graded Composite Layer

Another expedient contemplated here, for a barrier coating or layer 30 and an adjacent pH protective coating or layer 34, is a graded composite of any two or more adjacent PECVD layers, for example the barrier coating or layer 30 and a pH protective coating or layer 34 and/or a lubricity coating or layer 287, as shown in FIG. 1. A graded composite can be separate layers of a pH protective coating or layer 34 and/or barrier coating or layer 30 with a transition or interface of intermediate composition between them, or separate layers of a protective and/or hydrophobic layer and SiO$_x$ with an intermediate distinct pH protective coating or layer 34 of intermediate composition between them, or a single coating or layer that changes continuously or in steps from a barrier coating or layer 30 and/or hydrophobic coating or layer to a pH protective coating or layer 34 or a lubricity coating or layer 287, going in a normal direction to the coating set 285.

The grade in the graded composite can go in either direction. For example, the barrier coating or layer 30 can be applied directly to the substrate, such as an interior surface 16, or to a tie coating or layer 838, and graduate to a pH protective coating or layer 34 further from the interior surface 16. It optionally can further graduate to another type of coating or layer, such as a hydrophobic coating or layer or a lubricity coating or layer 287. A graduated tie coating or layer 838 is particularly contemplated if a layer of one composition is better for adhering to the substrate, in which case the better-adhering composition can, for example, be applied directly to the substrate. It is contemplated that the more distant portions of the graded tie coating or layer can be less compatible with the substrate than the adjacent portions of the graded tie coating or layer, since at any point the tie coating or layer is changing gradually in properties, so adjacent portions at nearly the same depth of the tie coating or layer have nearly identical composition, and more widely physically separated portions at substantially different depths can have more diverse properties. It is also contemplated that a tie coating or layer portion that forms a better barrier against transfer of material to or from the substrate can be directly against the substrate, to prevent the more remote tie coating or layer portion that forms a poorer barrier from being contaminated with the material intended to be barred or impeded by the barrier.

The applied coatings or layers, instead of being graded, optionally can have sharp transitions between one layer and the next, without a substantial gradient of composition. Such a coating or layer can be made, for example, by providing the gases to produce a layer as a steady state flow in a non-plasma state, then energizing the system with a brief plasma discharge to form a coating or layer on the substrate. If a subsequent coating or layer is to be applied, the gases for the previous coating or layer are cleared out and the gases for the next coating or layer are applied in a steady-state fashion before energizing the plasma and again forming a distinct layer on the surface of the substrate or its outermost previous coating or layer, with little if any gradual transition at the interface.

An embodiment can be carried out under conditions effective to form a hydrophobic pH protective coating or layer 34 on the substrate. Optionally, the hydrophobic characteristics of the pH protective coating or layer 34 can be set by setting the ratio of the O$_2$ to the organosilicon precursor in the gaseous reactant, and/or by setting the electric power used for generating the plasma. Optionally, the pH protective coating or layer 34 can have a lower wetting tension than the uncoated surface, optionally a wetting tension of from 20 to 72 dyne/cm, optionally from 30 to 60 dynes/cm, optionally from 30 to 40 dynes/cm, optionally 34 dyne/cm. Optionally, the pH protective coating or layer 34 can be more hydrophobic than the uncoated surface.

PECVD Apparatus for Forming PECVD Coatings or Layers

PECVD apparatus, a system and precursor materials suitable for applying any of the PECVD coatings or layers described in this specification, specifically including the tie coating or layer 838, the barrier coating or layer 30, or the pH protective coating or layer 34 are described in PCT Publ. Appl. WO2014085348A2 or U.S. Pat. No. 7,985,188, which are incorporated by reference.

Figure 6:
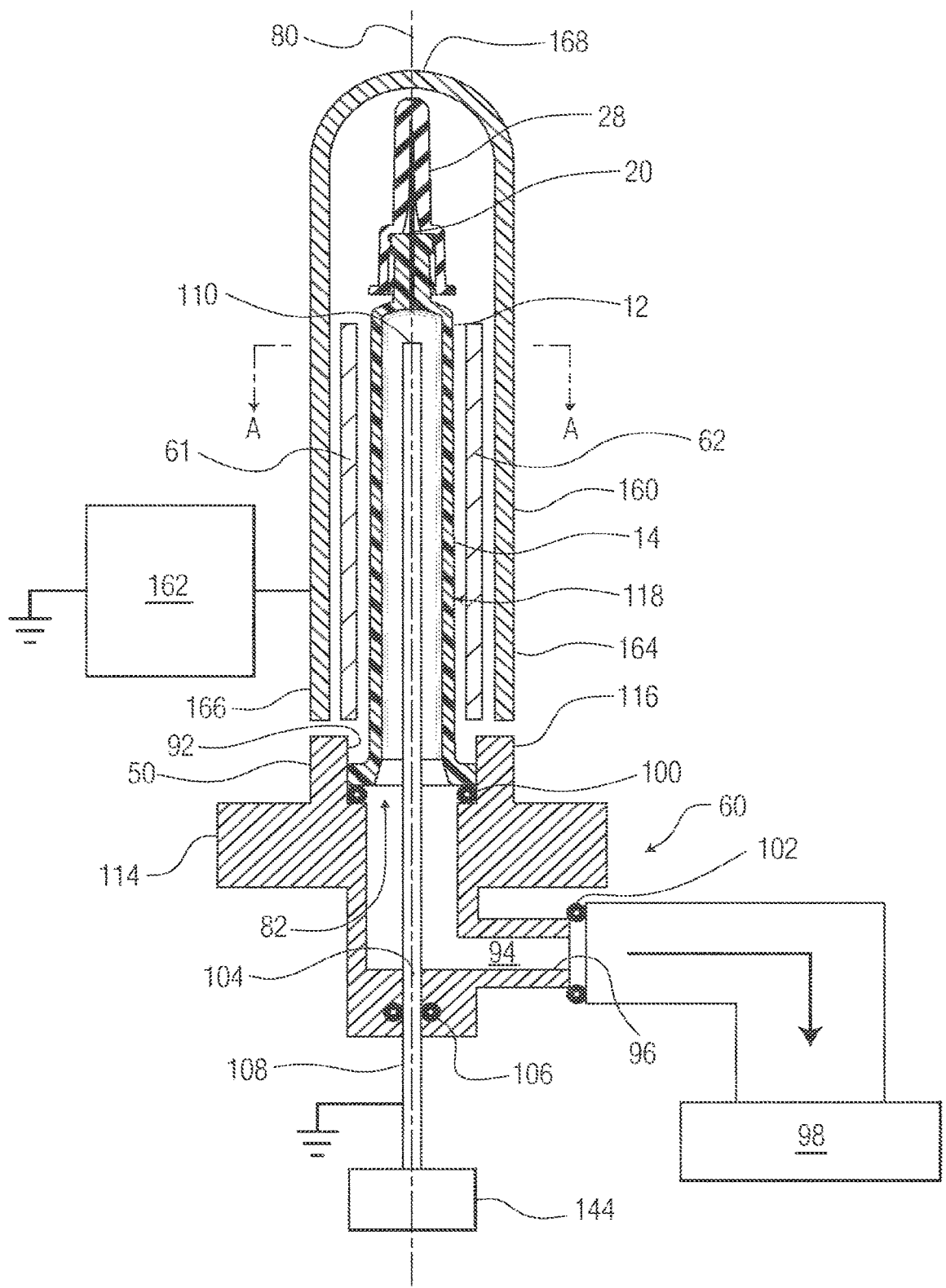
FIG. 6 is a schematic longitudinal section of the capped assembly of FIGS. 3 and 4 seated on a chemical vapor deposition coating station.
Figure 7:
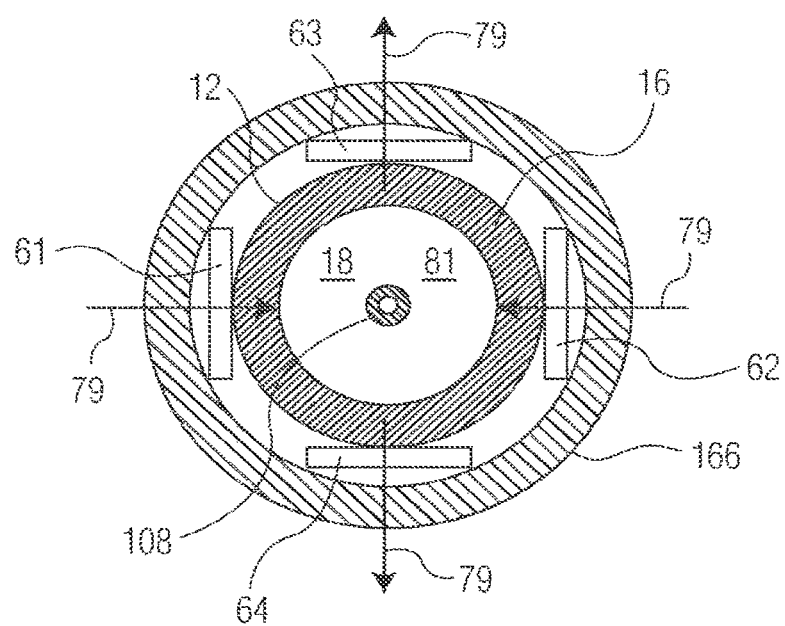
FIG. 7 is a section taken along section lines A-A of FIG. 6, showing a rotatable quadrupole magnet array.
Figure 8:
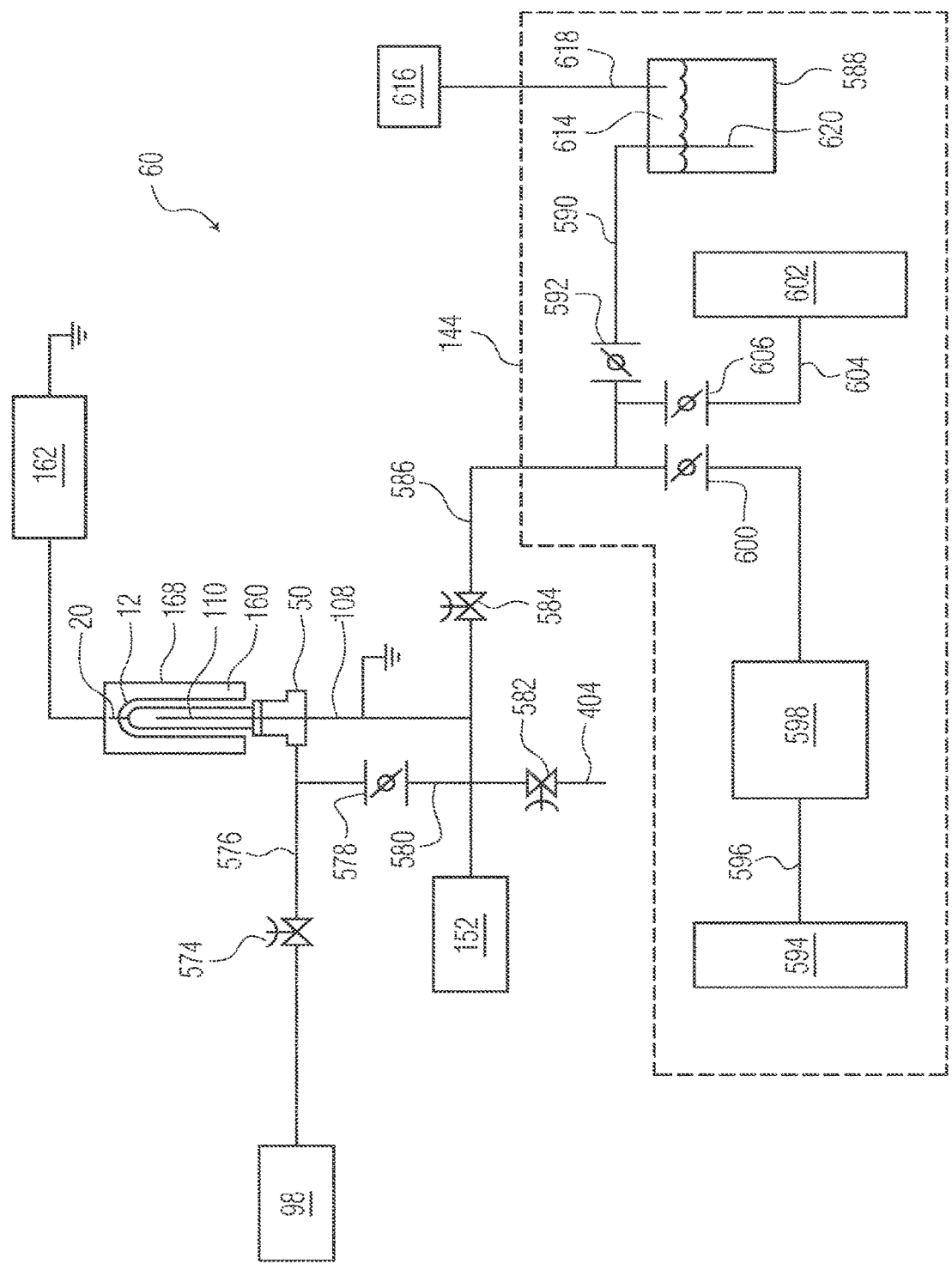
FIG. 8 is a schematic view showing more details of the chemical vapor deposition coating station shown in FIGS. 6-8.

An overview of these conditions is provided in FIGS. 6-8 which show a vessel processing system adapted for making such a vessel. A PECVD apparatus or coating station 60 suitable for the present purpose includes a vessel support 50, an inner electrode defined by the probe 108, an outer electrode 160, which optionally is generally cylindrical, and a power supply 162. The inner electrode 108 is located at least partially within the lumen of the vessel 14 during PECVD processing, and the outer electrode 160 is located outside the lumen of the vessel 14 during PECVD processing. The pre-capped assembly 12 seated on the vessel support 50 has a vessel 14 that defines a plasma reaction chamber, which optionally can be a vacuum chamber. Optionally, a source of vacuum 98, a reactant gas source 144, a gas feed (probe 108) or a combination of two or more of these can be supplied.

In any embodiment of the invention, the PECVD apparatus is contemplated for applying a PECVD set of one or more coatings on a vessel 14, particularly on its wall having a generally cylindrical inner surface defining a lumen, the generally cylindrical inner surface having a diameter in the range from 4 to 15 mm, for example, although these limits are not critical.

The PECVD apparatus can be used for atmospheric-pressure PECVD, in which case the plasma reaction chamber defined by the pre-capped assembly 12 does not need to function as a vacuum chamber.

Referring to FIGS. 6-8, the vessel support 50 comprises a gas inlet port 104 for conveying a gas into the pre-capped assembly 12 seated on the opening 82. The gas inlet port 104 can have a sliding seal provided for example by at least one O-ring 106, or two O-rings in series, or three O-rings in series, which can seat against a cylindrical probe 108 when the probe 108 is inserted through the gas inlet port 104. The probe 108 can be a gas inlet conduit that extends to a gas delivery port at its distal end 110. The distal end 110 of the illustrated embodiment can be inserted at an appropriate depth in the pre-capped assembly 12 for providing one or more PECVD reactants and other precursor feed or process gases. The inner electrode defined by the probe 108 has an outer surface including an end or distal portion 110 extending into the lumen and coaxial with and (optionally) radially spaced from 1 0.2 to 6.9 mm. from the generally cylindrical inner surface. The inner electrode 108 has an internal passage or gas delivery port 110 for supplying feed materials, having at least one outlet for introducing a gaseous PECVD precursor into the lumen, optionally one or more perforations or the port 110, for example. Electromagnetic energy can be applied to the outer electrode 160 under conditions effective to form a plasma enhanced chemical vapor deposition (PECVD) gas barrier coating having the desired mean thickness on the generally cylindrical inner surface.

FIG. 8 shows additional optional details of the coating station 60 that are usable, for example, with all the illustrated embodiments. The coating station 60 can also have a main vacuum valve 574 in its vacuum line 576 leading to the pressure sensor 152. A manual bypass valve 578 can be provided in the bypass line 580. A vent valve 582 controls flow at the vent 404.

Flow out of the PECVD gas or precursor source 144 can be controlled by a main reactant gas valve 584 regulating flow through the main reactant feed line 586. One component of the gas source 144 can be the organosilicon liquid reservoir 588, containing the precursor. The contents of the reservoir 588 can be drawn through the organosilicon capillary line 590, which optionally can be provided at a suitable length to provide the desired flow rate. Flow of organosilicon vapor can be controlled by the organosilicon shut-off valve 592. Pressure can be applied to the headspace 614 of the liquid reservoir 588, for example a pressure in the range of 0-15 psi (0 to 78 cm. Hg), from a pressure source 616 such as pressurized air connected to the headspace 614 by a pressure line 618 to establish repeatable organosilicon liquid delivery that is not dependent on atmospheric pressure (and the fluctuations therein). The reservoir 588 can be sealed and the capillary connection 620 can be at the bottom of the reservoir 588 to ensure that only neat organosilicon liquid (not the pressurized gas from the headspace 614) flows through the capillary tube 590. The organosilicon liquid optionally can be heated above ambient temperature, if necessary or desirable to cause the organosilicon liquid to evaporate, forming an organosilicon vapor. To accomplish this heating, the apparatus can advantageously include heated delivery lines from the exit of the precursor reservoir to as close as possible to the gas inlet into the syringe. Preheating can be useful, for example, when feeding OMCTS.

Oxidant gas can be provided from the oxidant gas tank 594 via an oxidant gas feed line 596 controlled by a mass flow controller 598 and provided with an oxidant shut-off valve 600.

Optionally in any embodiment, other precursor, oxidant, and/or diluent gas reservoirs such as 602 can be provided to supply additional materials if needed for a particular deposition process. Each such reservoir such as 602 can have an appropriate feed line 604 and shut-off valve 606.

Referring especially to FIG. 6, the processing station 60 can include an outer electrode 160 fed by a radio frequency power supply 162 for providing an electric field for generating plasma within the pre-capped assembly 12 during processing. In this embodiment, the probe 108 can be electrically conductive and can be grounded, thus providing a counter-electrode within the pre-capped assembly 12. Alternatively, in any embodiment the outer electrode 160 can be grounded and the probe 108 can be directly connected to the power supply 162.

In the embodiment of FIGS. 6-8, the outer electrode 160 can either be generally cylindrical as illustrated in FIGS. 6 and 7 or a generally U-shaped elongated channel. Each illustrated embodiment can have one or more sidewalls, such as 164 and 166, and optionally a top end 168, disposed about the pre-capped assembly 12 in close proximity.

Optionally in any embodiment, the outer electrode (160) can be made of foraminous material, for example a metal wire mesh material. Alternatively, the outer electrode (160) can be made of continuous material (meaning not perforated, woven, knitted or felted, for example), such as a metal cylinder.

Optionally in any embodiment, the inner electrode (108) extends axially into the lumen (18).

Optionally in any embodiment, the plasma modification of the surface (16) of the workpiece (12) comprises chemical vapor deposition, optionally plasma enhanced chemical vapor deposition (PECVD).

As was previously indicated, the inner electrode (108) optionally can do double duty as a material supply tube (104) for providing gaseous material to the lumen (18). The material supply tube (104) optionally, in any embodiment, has a wall disposed within the lumen (18).

Optionally in any embodiment, the wall has perforations to pass gaseous material to the lumen (18).

Optionally, further steps can be carried out by the system. For example, the coated vessels can be conveyed to a fluid filler which places formulation 40 from a fluid supply into the lumens of the coated vessels.

For another example the filled vessels can be conveyed to a closure installer, which takes closures, for example plungers or closures, from a closure supply and seats them in the lumens of the coated vessels.

Reaction conditions for forming the $SiO_x$ barrier coating or layer 30 are described in U.S. Pat. No. 7,985,188, which is incorporated by reference.

The tie coating or layer (also referred to as an adhesion coating or layer) can be produced, for example, using as the precursor tetramethyldisiloxane (TMDSO) or hexamethyldisiloxane (HMDSO) at a flow rate of 0.5 to 10 sccm, preferably 1 to 5 sccm; oxygen flow of 0.25 to 5 sccm, preferably 0.5 to 2.5 sccm; and argon flow of 1 to 120 sccm, preferably in the upper part of this range for a 1 mL syringe and the lower part of this range for a 5 ml. vial. The overall pressure in the vessel during PECVD can be from 0.01 to 10 Torr, preferably from 0.1 to 1.5 Torr. The power level applied can be from 5 to 100 Watts, preferably in the upper part of this range for a 1 mL syringe and the lower part of this range for a 5 ml. vial. The deposition time (i.e. "on" time for RF power) is from 0.1 to 10 seconds, preferably 1 to 3 seconds. The power cycle optionally can be ramped or steadily increased from 0 Watts to full power over a short time period, such as 2 seconds, when the power is turned on, which may improve the plasma uniformity. The ramp up of power over a period of time is optional, however.

The pH protective coating or layer 34 coating or layer described in this specification can be applied in many different ways. For one example, the low-pressure PECVD process described in U.S. Pat. No. 7,985,188 can be used. For another example, instead of using low-pressure PECVD, atmospheric PECVD can be employed to deposit the pH protective coating or layer 34. For another example, the coating can be simply evaporated and allowed to deposit on the $SiO_x$ layer to be protected. For another example, the coating can be sputtered on the $SiO_x$ layer to be protected. For still another example, the pH protective coating or layer 34 can be applied from a liquid medium used to rinse or wash the $SiO_x$ layer.

Pharmaceutical Package

The pharmaceutical package 210 illustrated most broadly by FIGS. 1, 2, and 15-17 is contemplated in any embodiment.

FIGS. 1-5, 10, and 19-32 illustrate several exemplary pharmaceutical packages or other vessels 210 including a wall 15 enclosing a lumen 18, a formulation 40 in the lumen 18, and a vessel coating set 285. The formulation 40 is contained in the lumen 18. Optionally for any of the embodiments, the formulation 40 is an aqueous fluid having a pH between 5 and 6, optionally between 6 and 7, optionally between 7 and 8, optionally between 8 and 9, optionally between 6.5 and 7.5, optionally between 7.5 and 8.5, optionally between 8.5 and 9. Optionally, the pH protective coating or layer 34 is effective to isolate a formulation 40 from the barrier coating 288. Optionally, the rate of erosion of the pH protective coating or layer 34, if directly contacted by an aqueous formulation 40 having a pH between 5 and 9, is less than the rate of erosion of the barrier coating 288, if directly contacted by an aqueous formulation 40 having a pH between 5 and 9. Optionally for any of the embodiments of FIGS. 1-5, the pharmaceutical package 210 can have a shelf life, after the pharmaceutical package 210 is assembled, of at least one year, alternatively at least two years.

Optionally for any of the embodiments, the shelf life is measured at 3° C., alternatively at 4° C. or higher, alternatively at 20° C. or higher, alternatively at 23° C., alternatively at 40° C.

Figure 9:
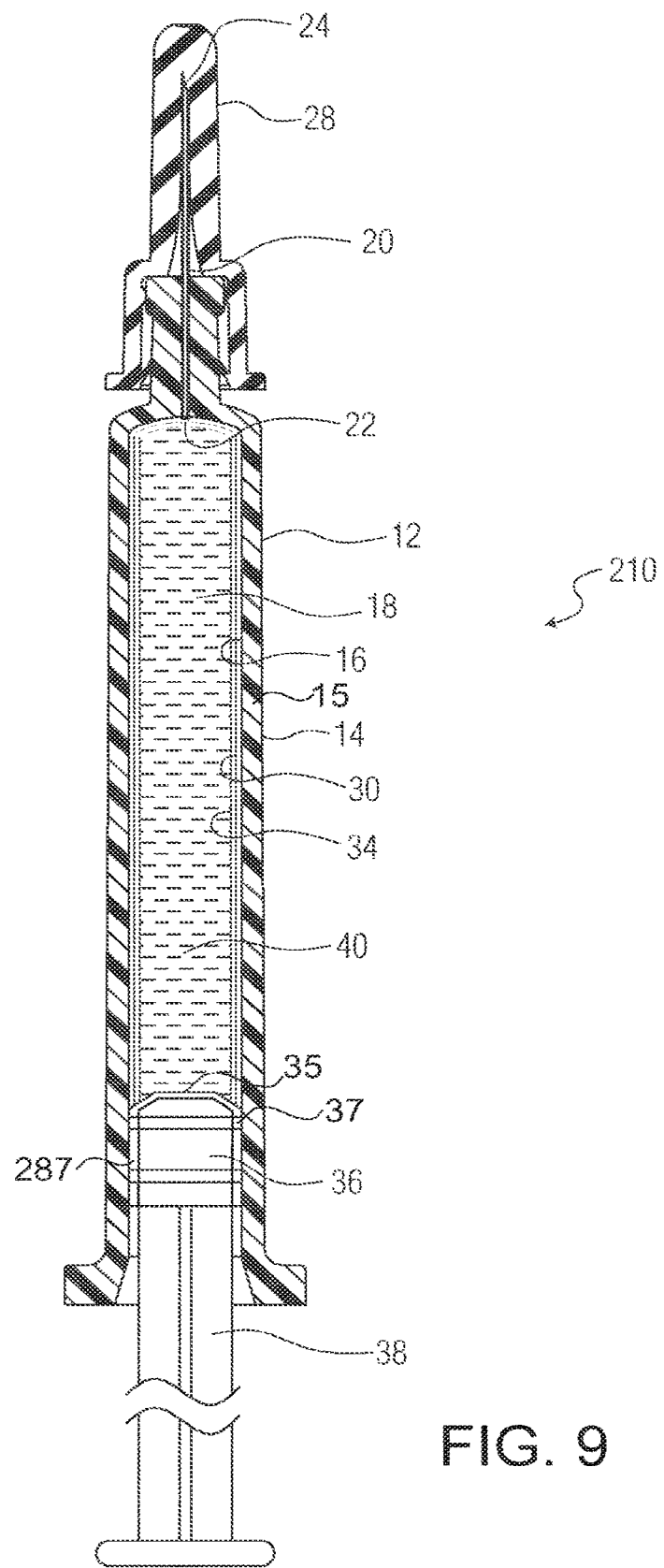
FIG. 9 is a view similar to FIG. 4 of the capped assembly of FIGS. 1-5, filled with a formulation 40 and fitted with a plunger tip, piston, stopper, or seal to define a pre-filled pharmaceutical package 210 embodied as a pre-filled syringe. In the option shown, a plunger tip, piston, stopper, or seal and plunger rod are installed.
Figure 10:
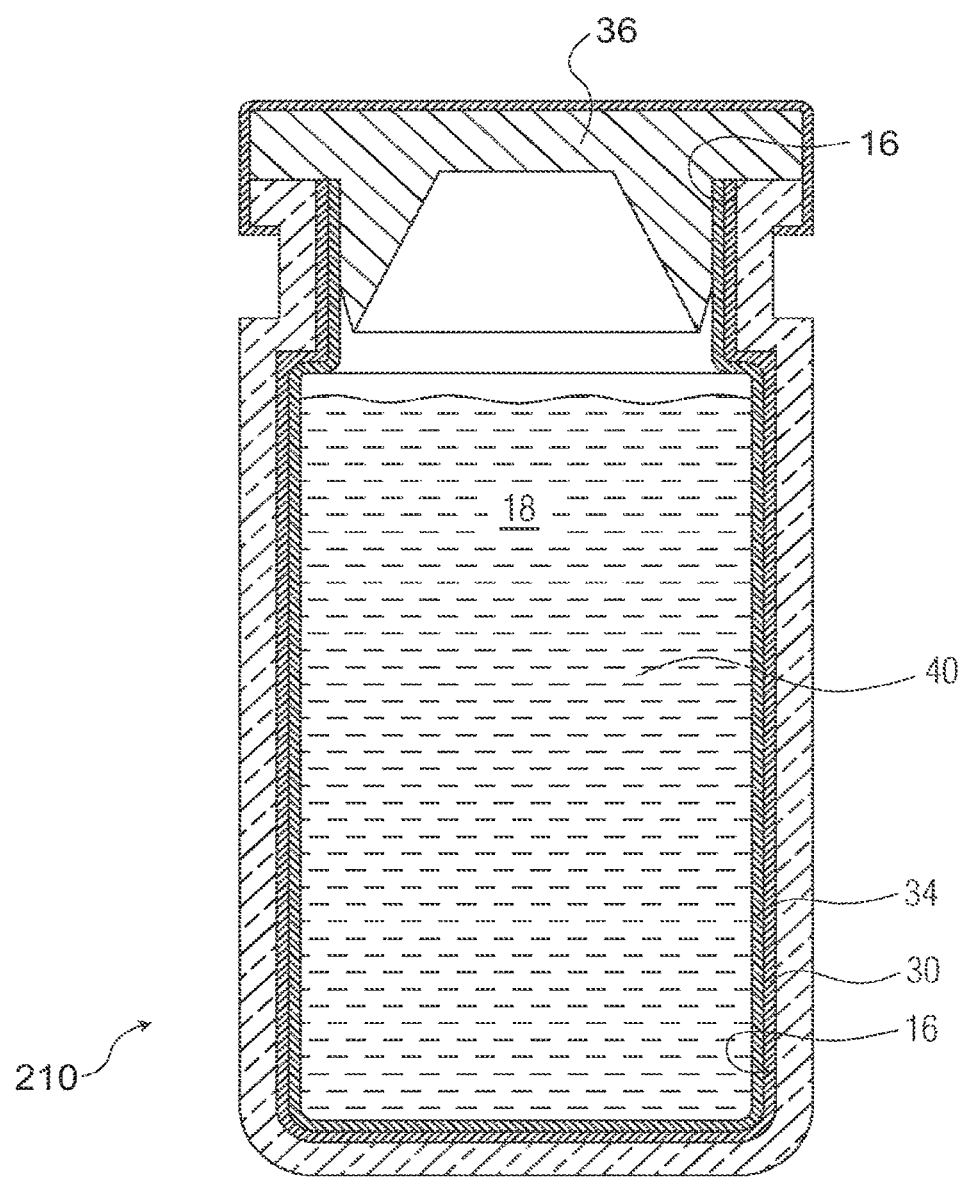
FIG. 10 is a longitudinal section of a pharmaceutical package 210 embodied as a vial fitted with a closure (septum and crimp) and having the same barrier coating or layer, passivation layer or pH protective coating, and other common features.

Referring to FIG. 9, the pharmaceutical package 210 embodied as a syringe optionally comprises a closure 36 embodied as a plunger inserted in the barrel 14 and a plunger rod 38. The plunger 36 optionally is provided with a lubricity coating or layer 287, at least on its surface in contact with the barrel interior surface 16. The lubricity coating or layer 287 on the plunger is in the right position to prevent "sticktion" during storage and to continue to lower the friction between the plunger tip and barrel when the plunger is advanced, and if applied by CVD is contemplated to be less subject to displacement by the force exerted by the plunger tip on the barrel than traditional silicon oil coatings or layers and more uniformly applied as a uniform coating rather than as isolated droplets of liquid.

An ophthalmic drug formulation in a pre-filled pharmaceutical package 210 is provided. The pre-filled pharmaceutical package 210 includes a vessel 14 having a lumen 18, a liquid formulation 40 of an ophthalmic drug suitable for intravitreal injection in the lumen 18, and a closure 36, for example a closure or a plunger, seated in the lumen 18.

The vessel 14 can be, for example, a syringe barrel, cartridge, or vial. The vessel 14 has a thermoplastic wall 15 having an interior surface 16 enclosing at least a portion of the lumen 18, an exterior surface 216, and a coating set 285 on at least one of the interior surface 16 and the exterior surface 216 of the wall 15. The coating set 285 can include a tie coating or layer 838, a barrier coating or layer 30, and optionally a pH protective coating or layer 34.

The tie coating or layer 838 can be formed on the interior surface 16 or the exterior surface 216. It has the composition SiOxCyHz in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS). The tie coating or layer 838 has a facing surface 840 facing toward the wall 15, and an opposed surface 842 facing away from the wall 15.

The barrier coating or layer 30 has the composition SiOx, in which x is from about 1.5 to about 2.9 as measured by XPS. The barrier coating or layer 30 has a facing surface 222 facing toward the opposed surface 842 of the tie coating or layer 838 and an opposed surface 216 facing away from the tie coating or layer 838.

The pH protective coating or layer 34, if present, has the composition SiOxCyHz, in which x is from about 0.5 to about 2.4 as measured by XPS, y is from about 0.6 to about 3 as measured by XPS, and z is from about 2 to about 9 as measured by at least one of RBS or HFS. The pH protective coating or layer 34, if present, has a facing surface 226 facing toward the opposed surface 216 of the barrier coating or layer 30 and an opposed surface 224 facing away from the barrier coating or layer 30.

The closure 36, for example a plunger or stopper, is seated in the lumen 18. It has a front face 35 facing the liquid formulation 40.

Optionally in any embodiment, a pre-filled pharmaceutical package 210 having a nominal maximum fill volume of 0.2 ml to 10 mL, alternatively 0.2 to 1.5 mL, alternatively 0.5 ml to 1.0 ml, alternatively 0.5 ml, 1.0 ml, 3 mL, or 5 mL is provided.

Optionally in any embodiment, the front face 35 of the closure 36 has a fluoropolymer surface, optionally a molded fluoropolymer surface or a fluoropolymer coating or layer, for example a laminated fluoropolymer film or a fluoropolymer coating.

Optionally in any embodiment, the ophthalmic drug suitable for intravitreal injection comprises a VEGF antagonist.

Optionally in any embodiment, the VEGF antagonist comprises an anti-VEGF antibody or an antigen-binding fragment of such antibody.

Optionally in any embodiment, the VEGF antagonist comprises Ranibizumab, Aflibercept, Bevacizumab, or a combination of two or more of these, optionally Ranibizumab.

Optionally in any embodiment, the concentration of the liquid formulation 40 of an ophthalmic drug suitable for intravitreal injection is 1 to 100 mg of the drug active agent per ml. of the liquid formulation 40 (mg/ml), alternatively 2-75 mg/ml, alternatively 3-50 mg/ml, alternatively 5 to 30 mg/ml, and alternatively 6 or 10 mg/ml.

Optionally in any embodiment, the liquid formulation 40 of an ophthalmic drug suitable for intravitreal injection comprises 6 mg/mL, alternatively 10 mg/mL, of Ranibizumab.

Optionally in any embodiment, the ophthalmic drug suitable for intravitreal injection further comprises: a buffer in an amount effective to provide a pH of the liquid formulation 40 in the range from about 5 to about 7; a non-ionic surfactant in the range of 0.005 to 0.02% mg./mL of complete formulation, alternatively in the range of 0.007 to 0.018% mg./mL of complete formulation, alternatively in the range of 0.008 to 0.015% mg./mL of complete formulation, alternatively in the range of 0.009 to 0.012% mg./mL of complete formulation, alternatively in the range of 0.009 to 0.011% mg./mL of complete formulation, alternatively 0.01% mg./mL of complete formulation; and water for injection.

Optionally in any embodiment, the ophthalmic drug suitable for intravitreal injection comprises 6 mg/mL, alternatively 10 mg/mL, of Ranibizumab; 100 mg/mL of α, α-trehalose dihydrate, 1.98 mg/mL L-histidine; and 0.1 mg/mL Polysorbate 20 in water for injection.

Optionally in any embodiment, having a shelf life of at least six months, alternatively at least 12 months, alternatively at least 18 months, alternatively 24 months, measured at a temperature of 5° C., alternatively 25° C.

Optionally in any embodiment, free of silicone oil on the product contacting surfaces of the pre-filled pharmaceutical package 210.

Optionally in any embodiment, free of baked-on silicone on the product contacting surfaces of the pre-filled pharmaceutical package 210.

Optionally in any embodiment, a syringe as the pharmaceutical package 210 comprising a barrel as the vessel 14 and a plunger as the closure 36, the syringe having a plunger sliding force of less than or equal to 10N for advancing the plunger in the lumen 18.

Optionally in any embodiment, a syringe as the pharmaceutical package 210 comprising a barrel as the vessel 14 and a plunger as the closure 36, the syringe having a breakout force of less than or equal to 10N for initiating travel of the plunger in the lumen 18.

Optionally in any embodiment, the ophthalmic drug suitable for intravitreal injection meets the particle count standard for particulate matter in ophthalmic solutions of USP789 as in force on Nov. 1, 2015, or Ph. Eur 5.7.1 as in force on Nov. 1, 2015, or both, at the time of filling the pre-filled syringe, alternatively after three months of storage of the pre-filled syringe at 4-8° C., alternatively after three months of storage of the pre-filled syringe at 25° C. and 60% relative humidity, alternatively after three months of storage of the pre-filled syringe at 40° C. and 75% relative humidity.

Optionally in any embodiment, the thermoplastic wall 15 comprises a polyolefin, for example a cyclic olefin polymer, a cyclic olefin copolymer, or polypropylene; a polyester, for example polyethylene terephthalate; a polycarbonate; or any combination or copolymer of any two or more of these, optionally cyclic olefin polymer (COP) resin.

Optionally in any embodiment, the tie coating or layer 838 comprising SiOxCyHz is between 5 and 200 nm (nanometers), alternatively between 5 and 100 nm, alternatively between 5 and 50 nm, alternatively about 38 nm thick as determined by transmission electron microscopy.

Optionally in any embodiment, the barrier coating or layer 30 of SiOx is from 2 to 1000 nm, alternatively from 4 nm to 500 nm, alternatively between 10 and 200 nm, alternatively from 20 to 200 nm, alternatively from 30 to 100 nm, alternatively about 55 nm thick as determined by transmission electron microscopy Optionally in any embodiment, the pH protective coating or layer 34 of SiOxCyHz, if present, is about from between 10 and 1000 nm, alternatively from 20 nm to 800 nm, alternatively from 50 nm to 600 nm, alternatively from 100 nm to 500 nm, alternatively from 200 nm to 400 nm, alternatively from 250 nm to 350 nm, alternatively about 270 nm, alternatively about 570 nm thick as determined by transmission electron microscopy.

Optionally in any embodiment, for the pH protective coating or layer 34 of SiOxCyHz, if present, x is from about 1 to about 2 as measured by XPS, y is from about 0.6 to about 1.5 as measured by XPS, and z is from about 2 to about 5 as measured by RBS or HFS.

Optionally in any embodiment, for the pH protective coating or layer 34 of SiOxCyHz, if present, x is about 1.1 as measured by XPS, y is about 1 as measured by XPS, and z is from about 2 to about 5 as measured by RBS or HFS.

Optionally in any embodiment, the pH protective coating or layer 34 of SiOxCyHz, if present, has a density between 1.25 and 1.65 g/cm3, alternatively between 1.35 and 1.55 g/cm3, alternatively between 1.4 and 1.5 g/cm3, alternatively between 1.44 and 1.48 g/cm3, as determined by X-ray reflectivity (XRR).

Optionally in any embodiment, the pH protective coating or layer 34 of SiOxCyHz, if present, has an RMS surface roughness value (measured by AFM) of from about 5 to about 9, alternatively from about 6 to about 8, alternatively from about 6.4 to about 7.8.

Optionally in any embodiment, the pH protective coating or layer 34 of SiOxCyHz, if present, has an Ra surface roughness value of the pH protective coating or layer 34, measured by AFM, from about 4 to about 6, alternatively from about 4.6 to about 5.8.

Optionally in any embodiment, the pH protective coating or layer 34 of SiOxCyHz, if present, has an Rmax surface roughness value of the pH protective coating or layer 34, measured by AFM, from about 70 to about 160, alternatively from about 84 to about 142, alternatively from about 90 to about 130.

Optionally in any embodiment, the pH protective coating or layer 34 of SiOxCyHz, if present, has a contact angle (with distilled water) of from 90° to 110°, alternatively from 80° to 120°, alternatively from 70° to 130°, as measured by Goniometer Angle measurement of a water droplet on the pH protective surface, per ASTM D7334-08 "Standard Practice for Surface Wettability of Coatings, Substrates and Pigments by Advancing Contact Angle Measurement."

Optionally in any embodiment, the pH protective coating or layer 34 of SiOxCyHz, if present, has an FTIR absorbance spectrum having a ratio from greater than 0.75 to 1.7, alternatively between 0.9 and 1.5, alternatively between 1.1 and 1.3, between the maximum amplitude of the Si—O—Si symmetrical stretch peak normally located between about 1000 and 1040 cm−1, and the maximum amplitude of the Si—O—Si asymmetric stretch peak normally located between about 1060 and about 1100 cm−1.

Optionally in any embodiment, the pH protective coating or layer 34 of SiOxCyHz, if present, has a silicon dissolution rate by a 50 mM potassium phosphate buffer diluted in water for injection, adjusted to pH 8 with concentrated nitric acid, and containing 0.2 wt. % polysorbate-80 surfactant (measured in the absence of the liquid formulation 40 of a VEGF antagonist, at 40° C.), less than 170 ppb/day.

Optionally in any embodiment, pre-filled pharmaceutical package 210 according to any one of the preceding claims, comprises a 0.5 or 1 mL volumetric capacity COP syringe equipped with a fluoropolymer coated closure front face 35.

Optionally in any embodiment, the vessel 14 is a syringe barrel having a front dispensing opening 26 and a back opening 32 and the closure 36 is a plunger that is axially slidable in the vessel 14 toward the front dispensing opening 26

Optionally in any embodiment, the plunger comprises a sleeve 120, a first cavity 122, and a second cavity 124. The sleeve 120 has a front end facing the front dispensing opening 26 and a back end facing the back opening 32, a first cavity 122 in the sleeve 120, a second cavity 124 in the sleeve 120 spaced axially from and in communication with the first cavity 122, and an insert 126 initially located in the first cavity 122 and configured to be displaced axially from the first cavity 122 to the second cavity 124, wherein the insert 126 is optionally partially generally spherical in shape, the insert 126 being configured to provide a first biasing force pressing at least a portion of the sleeve 120 adjacent to the insert 126 radially outward against the barrel when the insert 126 is in the first cavity 122, and to provide a second such biasing force that is a smaller than the first biasing force, optionally causing the sleeve 120 to be spaced from the barrel, when the insert 126 is in the second cavity 124.

FIGS. 19-22 illustrate a closure 36 embodied as a two-position plunger assembly 310 according to an embodiment of the present invention. Optionally in any embodiment, the closure can be an axially stretchable plunger 36 in the vessel 14 axially slidable toward the front dispensing opening 26, the closure 36 comprising: an elastomeric sleeve 120, optionally made from a thermoplastic elastomer, having a sidewall 15 and a front face 35 facing the front dispensing opening 26, the sidewall 15 comprising a stretch zone 154 that is adapted to undergo axial elongation to convert the closure 36 from a storage mode to a dispensing mode, wherein the elongation reduces an outer profile of at least a portion of the sidewall 15, thus reducing the closure 36 to a constricted state in the dispensing mode.

The plunger assembly 310 may have a variety of different shapes and sizes. For example, according to an illustrated embodiment, the plunger assembly 310 may be approximately 79 millimeters long. The plunger assembly 310 includes a convertible plunger 312 and a plunger rod 314. The plunger rod 314 may include an interior shaft 316 and an exterior shaft 318. The interior shaft 316 includes a distal end 320, a proximal end 322, and a locking tab 324. According to certain embodiments, the distal end 320 of the interior shaft 316 may be configured to form an actuator 326 that, during use of the plunger assembly 310, is to be pressed upon by a user, such as, for example, by the thumb of the user. The exterior shaft 318 may include a first end 328, a second end 330, a first recess 332, a second recess 334, and an inner portion 336. According to certain embodiments, the first end 328 may be configured for a threaded engagement with the convertible plunger 312. For example, as shown, the first end 328 may include an external thread 338 that is configured to mate with an internal thread 340 of the convertible plunger 312.

At least a portion of the interior shaft 316 is configured for slideable displacement along the inner portion 336 of the exterior shaft 318. Additionally, the locking tab 324 may protrude from at least a portion of the interior shaft 316. In the illustrated embodiment, the locking tab 324 has a tapered surface 325 that may assist in controlling the direction and timing of the displacement of the interior shaft 316 along the inner portion 336 of the exterior shaft 318. For example, at least FIG. 20 illustrates the interior shaft 316 in a first position relative to the exterior shaft 318, with the locking tab 324 protruding into at least a portion of the first recess 332 of the exterior shaft 318. The orientation of the tapered surface 325 of the locking tab 332 allows, when sufficient force is exerted upon the actuator 326, for the locking tab 332 to be at least temporarily compressed or deformed in size so that the locking tab 324 may at least temporarily enter into the inner portion 326 as the locking tab 325 is moved from the first recess 332 to the second recess 334. However, in the absence of sufficient force, the locking tab 332 may remain in the first recess 332, thereby maintaining the interior shaft 316 in the first position.

The distance that the locking tab 324 is to travel from the first recess 332 to the second recess 334, and thus the distance the interior shaft 316 is displaced relative to the exterior shaft 318 when moving from the first position to the second position may vary for different plunger assemblies. For example, according to certain embodiments, the interior shaft 316 may be displaced approximately 3 to 5 millimeters. Additionally, as shown in FIGS. 20 and 23, according to certain embodiments, the proximal end 322 of the interior shaft 316 may or may not be housed in the interior portion 336 of the exterior shaft 318 when the interior shaft 316 is in the first position.

Further, the orientation and size of the tapered surface 325 of the locking tab 324 may provide the locking tab 324 with sufficient width to prevent the locking tab 324 from being pulled into the inner portion 336 in the general direction of the second end 330 of the exterior shaft 318. Accordingly, when the locking tab 324 is in the second recess 334, and thus the interior shaft 316 is in the second position, the orientation and size of the tapered surface 325 of the locking tab 324 may provide the locking tab 324 with sufficient width to resist the locking tab 324 from being pulled back into the first recess 332.

Figure 21:
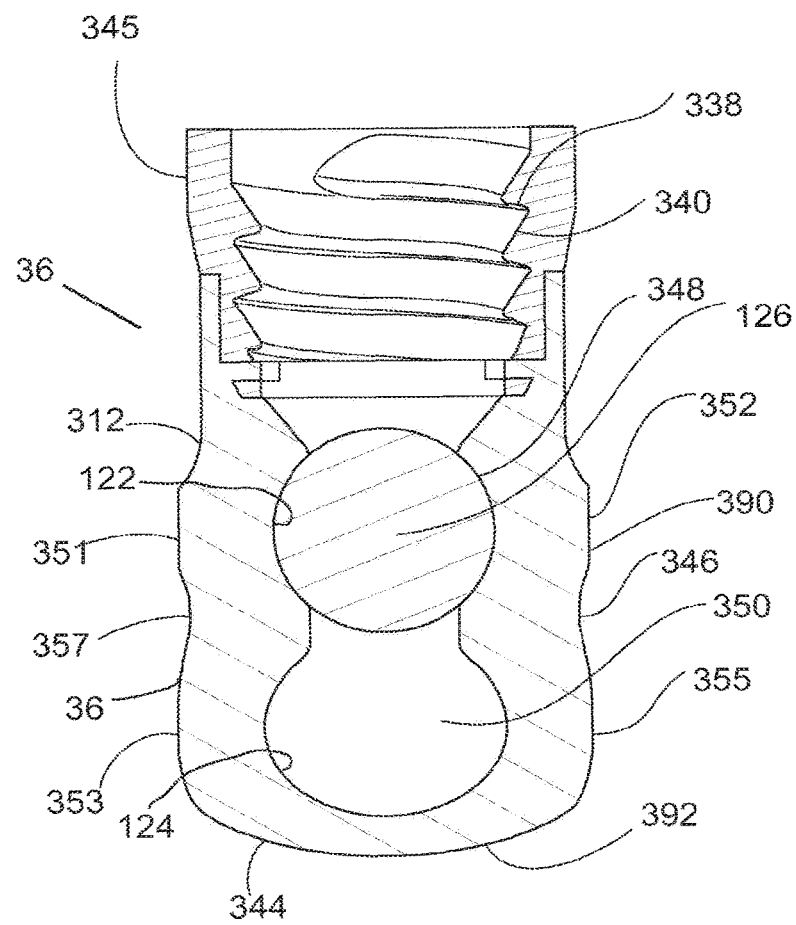
FIG. 21 illustrates an isolated partial sectional view of the plunger shown in FIG. 20, with the connector body transparent to reveal internal structure.
Figure 22:
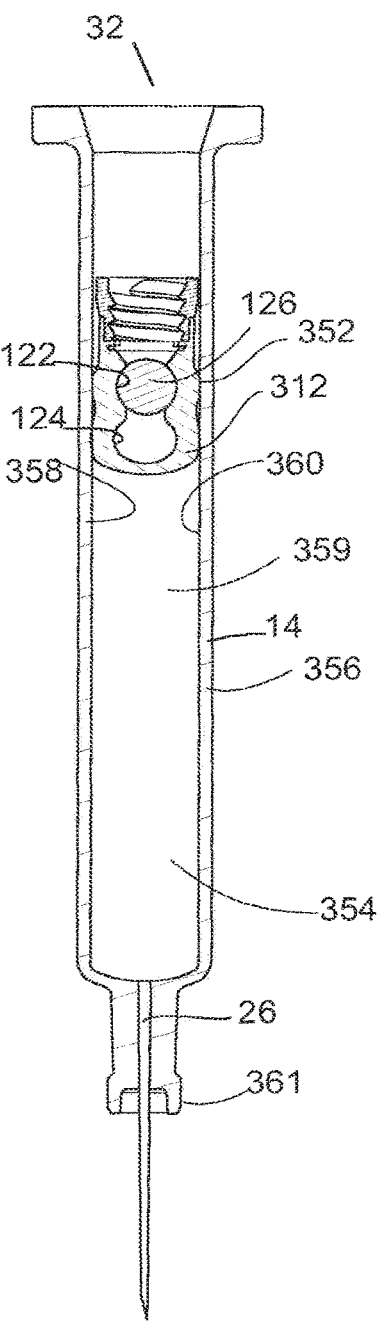
FIG. 22 illustrates a partial sectional view of the plunger of FIG. 21 positioned within a barrel of a syringe.

As shown in at least FIGS. 20-22, the convertible plunger 312 is configured to be received in an interior area 354 of a barrel 356 (e.g., of a syringe). The interior area 354 may be generally defined by a sidewall 358 of the barrel 356, the sidewall 358 having an inner surface 360. Additionally, the interior area 354 may include a product containing area 359 between the convertible plunger 312 and the proximal end 361 of the barrel 356.

According to certain embodiments, as best shown in FIG. 21, the convertible plunger 312 includes an insert 126, a sleeve 120, and a connector body 345. The connector body 345 may be operably connected to the sleeve 120, such as, for example, through the use of over molding, a plastic weld, an adhesive, and/or a mechanical fastener, such as a screw, bolt, pin, or clamp, among other connections. As previously discussed, the connector body 345 may be configured to be connected to the exterior shaft 318, such as, for example, by the threaded engagement of the internal thread 340 of the connector body 345 and the external thread 338 of the exterior shaft 318. Additionally, according to certain embodiments, the connector body 345 may be molded from a relatively stiff and/or rigid material, such as, for example, polyethylene or polypropylene, among other materials.

The sleeve 120 may be configured to provide a first cavity 122 and a second cavity 124. Additionally, the first and second cavities 348, 350 are in communication with each other and are configured to receive the movable insertion of the insert 126. The terms "first cavity" and "second cavity" may refer to physically distinct compartments (e.g., having an interruption, transition region, membrane or geometrical change between them, such as shown in FIG. 21) or alternatively a single compartment that is adapted to facilitate retaining an insert in a first position within the compartment (i.e., "first cavity") and then a second position within the same compartment (i.e., "second cavity"), with no interruption, transition region, membrane or geometrical change between the first cavity and second cavity.

The outer portion 346 of the sleeve 120 comprises a nose cone 392 (generally facing the syringe contents), and a sidewall 390 (generally facing the sidewall 358 of the barrel 356). The term "nose cone" 392 refers to the syringe contents-facing surface of the convertible plunger 312, and may be of any suitable geometry (e.g., rounded, cone-shaped, flat, etc.). The sidewall 390 of the sleeve 120 includes a storage sealing section 351 comprising at least one rib 352 that is preferably generally adjacent to and/or aligned with at least a portion of the first cavity 122. For example, as shown by at least FIG. 21, a single rib 352 of the storage sealing section 351 is generally adjacent to and/or aligned with the first cavity 122. However, the number of ribs 352 of the storage sealing section 351 aligned with and/or adjacent to the first cavity 122 may vary. Further, according to certain embodiments, a rib 352 of the storage sealing section 351 may not be positioned adjacent to and/or aligned with the second cavity 124. The sleeve 120 may be constructed from a thermoset rubber (e.g., butyl rubber) having good gas barrier properties, or a thermoplastic elastomer, among other materials. The purpose of the storage sealing section 351 is to provide CCI and optionally a barrier to one or more gases (e.g., oxygen) when the convertible plunger 312 is in a "storage mode," e.g., to seal the contents of a pre-filled syringe when in storage, prior to use. The gas barrier should effectively prevent ingress of gas(es) that may degrade the product contained within the syringe during the product's desired shelf life. The gas barrier should also effectively prevent egress of gas(es) that preferably remain within the product containing area 359 of the syringe. The particular gas(es) for which the storage sealing section 351 optionally provides a barrier when the plunger is in storage mode may vary depending on the product contained within the syringe. Optionally (in any embodiment), the gas barrier is an oxygen barrier. When the convertible plunger 312 is converted from storage mode to dispensing mode, the seal initially provided by the storage sealing section 351 is either reduced or removed entirely (i.e., such that the storage sealing section 351 no longer physically contacts the sidewall 358 of the barrel 356).

The insert 126 may also be constructed from a variety of different products, including products that allow the insert to have a lower, similar, or higher rigidity than/to the sleeve 120. Preferably, in any embodiment, the insert has a higher rigidity than the sleeve. Additionally, the insert 126 may have a variety of shapes and be generally configured to occupy at least one of the first and second cavities 348, 350. According to the embodiment illustrated in FIGS. 20-22, the insert 126 has a generally spherical shape. Alternative insert embodiments and shapes are disclosed below.

The sleeve 120, and particularly the rib 352 of the storage sealing section 351, and the insert 126 are configured to provide a force that compresses the rib 352 against the sidewall 358 of a barrel 356, as shown in FIG. 22. Such compression of the rib 352 of the storage sealing section against the sidewall 358 provides a seal, such as a compression seal in a "storage mode", between the convertible plunger 312 and the sidewall 358 that protects the sterility and/or integrity of injection product contained in the barrel 356. A typical compression may be, e.g., less than 10% of the overall width or diameter of the rib 352 and/or sleeve 120 when the convertible plunger 312 is compressed to form a seal in the barrel 356, optionally less than 9%, optionally less than 8%, optionally less than 7%, optionally less than 6%, optionally less than 5%, optionally less than 4%, optionally less than 3%, optionally less than 2%, optionally from 3% to 7%, optionally, from 3% to 6%, optionally from 4% to 6%, optionally from 4.5% to 5.5%, optionally from 4.5% to 5.5%, optionally about 4.8%. The compression is dependent on not only the geometric tolerances of the plunger and syringe barrel but also the material properties of the plunger (e.g., durometer of the rubber). Optionally, additional ribs 352 of the storage sealing section 351 may be included, which may increase the integrity of the seal and/or form separate seals between the plunger 312 and the sidewall 358 of the barrel 356.

According to certain embodiments, the sleeve 120 and insert 126 are sized such that, when the plunger 312 is in the barrel 356 and the insert 126 is in the first cavity 122, the insert 126 prevents or minimizes a reduction in the size of the first cavity 122. Such minimizing or prevention of a reduction in size of the first cavity 122 may minimize the extent the size of the rib 352 of the storage sealing section 351, which is generally adjacent and/or aligned to/with the first cavity 122, may be reduced by engagement of the rib 352 with the sidewall 358 of the barrel 356. According to such embodiment, the rib 352 may be sized such that, with the support of the insert 344 in the first cavity 122, the rib 352 is large enough to be compressed between the sleeve 120 and the sidewall 358 to form the compression seal for storage mode of the plunger 312. Further, according to certain embodiments, the insert 126 may be configured to limit the compression of the rib 352 and/or sleeve 120 such that the rib 352 and/or sleeve 120 is compressed less than 20% of the overall width of the sleeve 120 when the plunger 312 is being used to form a seal during storage mode in the barrel 356. Optionally, the rib 352 and/or sleeve 120 are compressed less than 10% of the overall width or diameter of the rib 352 and/or sleeve 120 when the plunger 312 is compressed to form a seal in the barrel 356, optionally less than 9%, optionally less than 8%, optionally less than 7%, optionally less than 6%, optionally less than 5%, optionally less than 4%, optionally less than 3%, optionally less than 2%, optionally from 3% to 7%, optionally, from 3% to 6%, optionally from 4% to 6%, optionally from 4.5% to 5.5%, optionally from 4.5% to 5.5%, optionally about 4.8%.

Alternatively, according to other embodiments, the insert 126 may be sized to expand the size of the first cavity 122 and rib 352 of the storage sealing section 351 so as to provide sufficient support to push or force the rib 352 against the sidewall 358 to form the compression seal during storage mode of the plunger 312.

The plunger 312 may be positioned in the barrel 356 before or after the plunger 312 is connected to the exterior shaft 318. When injection product in the syringe barrel, such as in the product containing area 359 of the barrel 356, is to be dispensed from the barrel 356, a user may depress the actuator 26 to displace the interior shaft 316 from the first position to the second position, as previously discussed. In the embodiment shown in FIGS. 19-22, as the interior shaft 316 is displaced to the second position, the proximal end 322 of the interior shaft 316 may exit the first end 28 of the exterior shaft 318 and enter into the plunger 312. As the locking tab 324 is moved to the second recess 334, the interior shaft 316 may push the insert 126 from the first cavity 122 to the second cavity 124.

With the insert 126 in the second cavity 124, the support and/or force that the insert 126 had been providing/exerting upon the rib 352 of the storage sealing section 351 is reduced and/or removed. Thus, under such circumstances, the force previously exerted by the rib 352 against the sidewall 358 of the barrel 356 is also at least reduced, or preferably removed (i.e., with no contact between the rib 352 of the sealing section 351 and the sidewall 358 of the barrel 356 when the plunger 312 is in a "dispensing mode."). Additionally, according to certain embodiments, a rib 352 may not be generally adjacent to and/or aligned with the second cavity 124 of the sleeve 120 so that the presence of the insert 126 in the second cavity 124 is not supporting or pushing a different rib 352 against the sidewall 358. Thus, with the force that had been exerted by the rib 352 against the sidewall 358 being removed or reduced by the displacement of the insert 126 to the second cavity 124, the force needed to displace the plunger 312 along the barrel 356 is less than the force would have been had the insert 126 remained in the first cavity 122. Thus, the force that had been exerted against the sidewall 358 by the plunger 312 is adjusted, and more specifically reduced, when the plunger 312 is to be displaced for dispensing of the injection product. Moreover, the extent of the force reduction is such that the injection product may be pushed completely forward out of the syringe against the back pressure caused by the viscosity of the injection product and/or the needle gauge. With the insert 126 in the second cavity 124 and the interior shaft 316 in the second position, the plunger assembly 310 may be displaced to reduce the size of the product containing area, and thereby dispense the injection product from the barrel 356.

Additionally, according to certain embodiments, the plunger 312 may optionally be configured such that when the first cavity 122 is not occupied by the insert 126, the rib 352 nonetheless maintains contact with the sidewall 358 of the barrel 356. Moreover, under such conditions, the rib 352 may be configured to provide a wiper surface to assist in the removal of injection product from the barrel 356 as the plunger assembly 310 is displaced during administration/dispensing of the injection product.

Optionally, the outer portion 346 of the sleeve 120 may include a liquid sealing section 353, preferably on the sidewall 390 of the sleeve 120, optionally adjacent to, distal to or otherwise near to the nose cone 392. The liquid sealing section 353 comprises at least one rib 355 of the liquid sealing section 353. The purpose of the liquid sealing section 353 is to provide a liquid tight seal both when the plunger 312 is in a storage mode as explained above, and when the plunger is transitioned into a "dispensing mode," i.e., when the storage sealing section 351 reduces or ceases compressive force against the barrel wall 358 so as to facilitate advancement of the plunger to dispense the contents of the syringe. Optionally, the liquid sealing section 353 may also provide CCI. Preferably, there is a valley 357 separating the storage sealing section 351 from the liquid sealing section 353.

Optionally in any embodiment, the vessel 14 is a syringe barrel having a front dispensing opening 26 and a back opening 32 and the closure 36 is an axially extending plunger in the vessel 14 that is axially slidable toward the front dispensing opening 26, the closure 36 comprising: an axially extending central core 130 having a storage sealing section 132 having a storage diameter 136 and a dispensing sealing section 134 axially spaced from the storage sealing section 132 and having a dispensing diameter 138, in which the dispensing diameter 138 is less than the storage diameter 136; and a sealing ring 140 encircling the central core 130 and having a first position at the storage sealing section 132, where the sealing ring 140 is compressed with storage sealing force between the central core 130 and the wall 15, and a second position at the dispensing sealing section 134, where either the sealing ring 140 is compressed against the wall 15 with a dispensing sealing force less than the storage sealing force or the sealing ring 140 is spaced from the wall 15.

Figure 25:
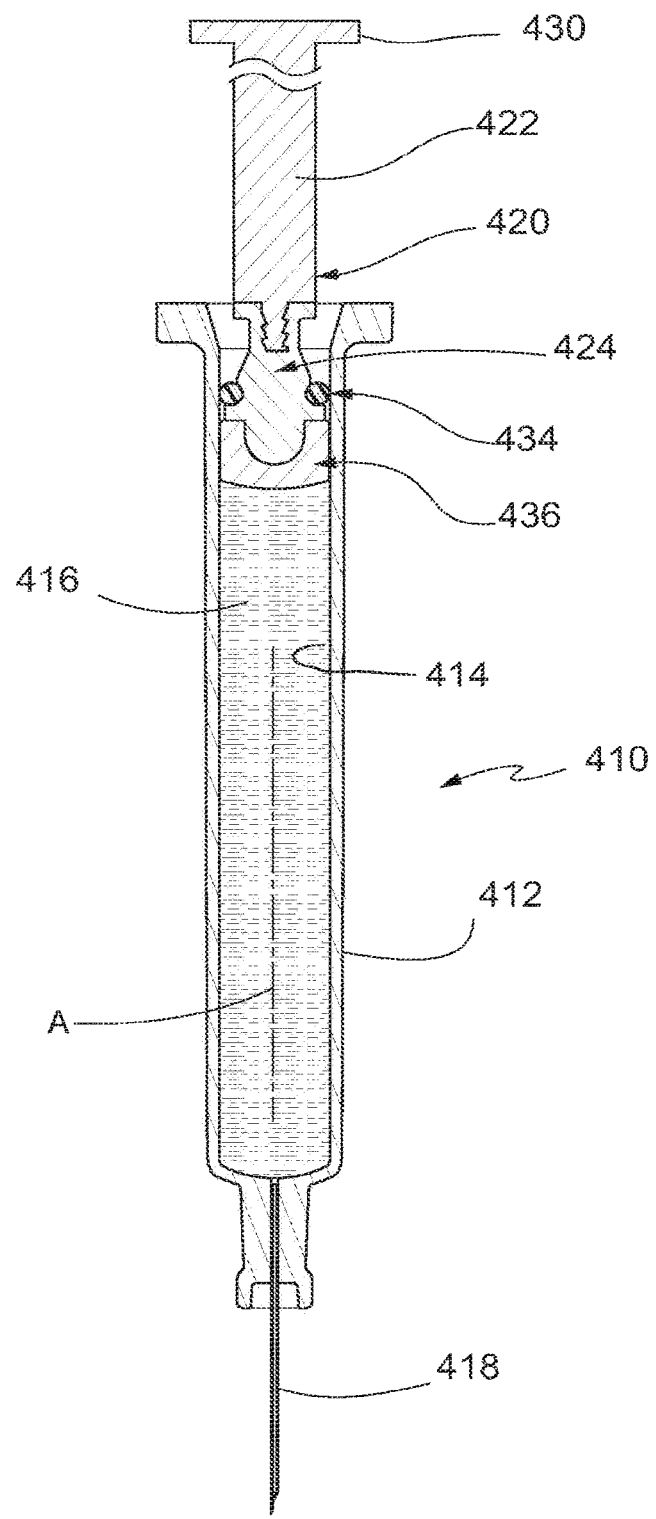
FIG. 25 is an axial sectional view of one exemplary syringe.
Figure 26:
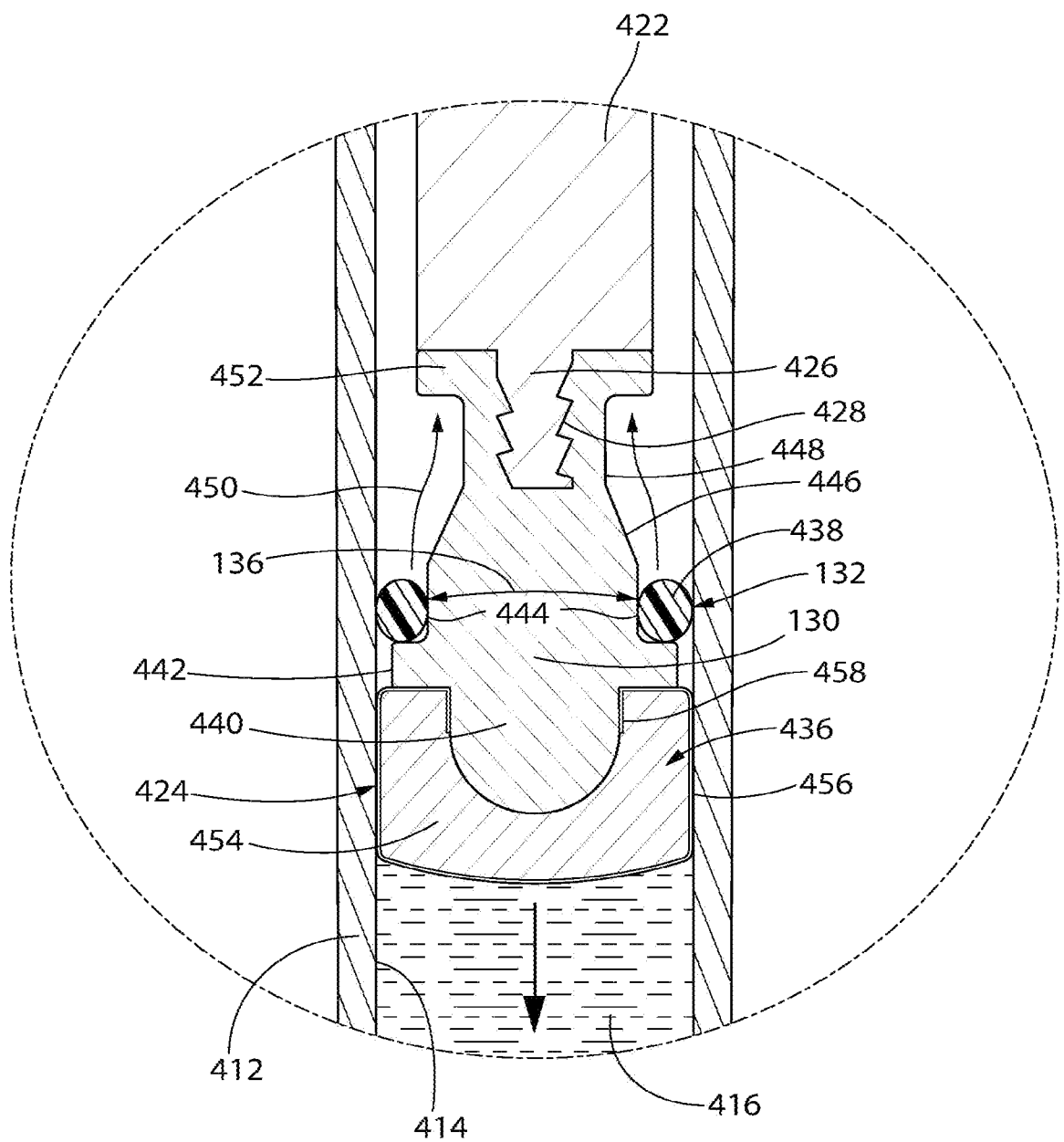
FIG. 26 is an enlarged axial sectional view of a portion of a convertible plunger forming a portion of the syringe shown in FIG. 25, with the plunger being shown in its engagement position in the syringe, wherein its storage sealing section forms a liquid-tight and gas-tight interface with the interior wall of the syringe and its liquid sealing section forms a liquid-tight interface with the interior wall of the syringe.
Figure 27:
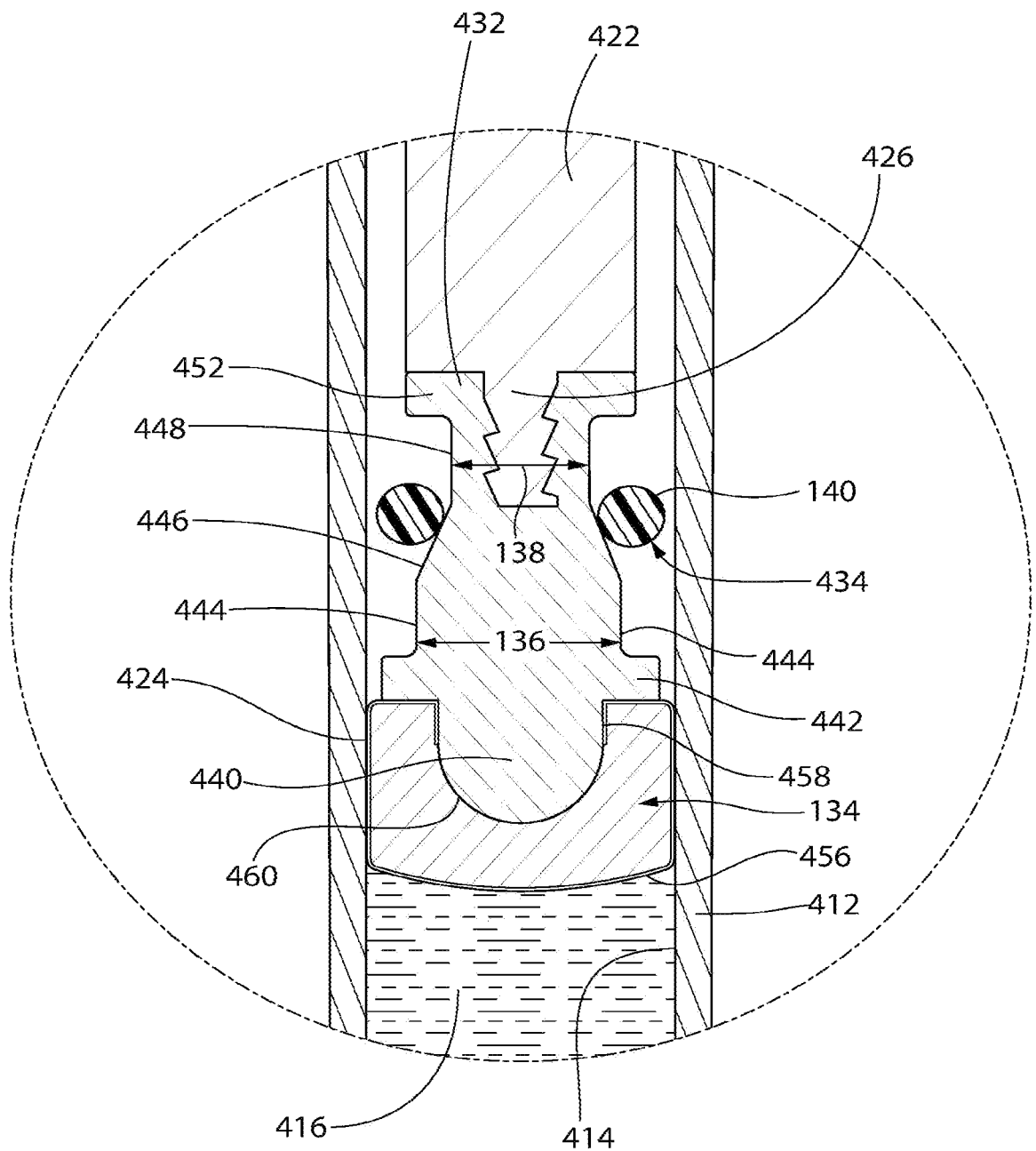
FIG. 27 is an enlarged sectional view, similar to FIG. 26, but showing the convertible plunger as it is moved from its engagement position to a release position wherein its storage sealing section no longer forms a liquid-tight and gas-tight interface with the interior wall of the syringe but its liquid sealing section still forms a liquid-tight interface with the interior wall of the syringe.

In FIGS. 25-27, one exemplary embodiment of a syringe 410 including a plunger assembly 420 constructed in accordance with one aspect of this invention is shown. The syringe 410 is of generally conventional construction and includes a hollow barrel 412 having a central longitudinal axis A. The barrel has an inner surface 414 and is configured to hold an injectable liquid 416 therein. A needle 418 is located at the distal end of the barrel and is in fluid communication therewith. The plunger assembly 420 is disposed so that a distal portion of it is located in the proximally located portion of the barrel, whereupon the syringe is ready for use. To that end, when the plunger assembly is actuated, e.g., pushed in the distal direction, it forces the injectable liquid within the barrel out through the needle 418.

The plunger assembly 420 basically comprises a plunger rod 422 and a convertible plunger 424. The convertible plunger 424 constitutes a subassembly of components which are configured to provide sufficient compressive force against the inner surface of the sidewall of a prefilled syringe or cartridge barrel to effectively seal and preserve the shelf-life of the contents of the barrel during storage. When a convertible plunger, such as that of the subject invention, provides container closure integrity (CCI) adequate to effectively seal and preserve the shelf-life of the contents of the barrel during storage, the convertible plunger (or at least a portion of its exterior surface) may alternatively be characterized as being in an expanded state or storage mode. The expanded state or storage mode may be a product of, for example, an expanded outer diameter or profile of at least a portion of the syringe barrel-contacting surface of the plunger and/or the normal force that the plunger exerts on the inner wall of the syringe barrel in which it is disposed. The convertible plunger (or at least a portion of its exterior surface) is reducible to what may alternatively be characterized as a constricted state or a dispensing mode, wherein the compressive force against the sidewall of the barrel is reduced, allowing a user to more easily advance the plunger in the barrel and thus dispense the contents of the syringe or cartridge. The constricted state or dispensing mode may be a product of, for example, a reduced outer diameter (relative to that of the expanded state) of at least a portion of the syringe barrel-contacting surface of the plunger and/or reduced normal force against the inner wall of the syringe barrel exerted by the plunger. Accordingly, in one aspect, the invention is a convertible plunger comprising a central core 130 having a longitudinal axis which is coaxial with the central axis A of the barrel 412, a storage sealing section 132 and a dispensing sealing section 134. The storage sealing section and the liquid sealing section each have a respective generally cylindrical exterior surface. As used herein, a "generally cylindrical" exterior surface may include minor interruptions or variations in geometry (e.g., due to ribs, valleys, etc.) to the otherwise cylindrical shape of the liquid sealing section. As will be described in detail later, the generally cylindrical exterior surface of the storage sealing section includes one or more annular ribs or outwardly projecting surfaces for engagement with the inner wall of the syringe barrel when the storage sealing section is in its expanded state. The expanded state is reducible to a constricted state by the relative movement of the storage sealing section along the longitudinal axis A with respect to the liquid sealing or vice versa. As used herein, "expanded state" and "constricted state" may refer to comparative dimensional measurements (e.g., expanded state being wider than constricted state) and/or comparative resistance to inward compression of the plunger (the "expanded state" being more resistant to inward compression and the "constricted state" being less resistant to inward compression) and/or comparative outward radial pressure exerted by at least a portion of the plunger's exterior surface (the plunger's exterior surface in the "expanded state" exerting more outward radial pressure and in the "constricted state" exerting less outward radial pressure).

The convertible plunger 424 is mounted on the distal end of the plunger rod 422. The plunger rod is an elongated member having a central longitudinal axis extending coaxially with the central axis A of the barrel of the syringe. The distal end of the plunger rod is in the form of a threaded projection 426 (FIG. 42A) extending outward from the distal end of the rod and centered on the axis A. The threaded projection 426 is configured to be threadedly received within a mating threaded bore or hole 428 in proximal end of the convertible plunger 424 to mount the convertible plunger on the distal end of the plunger rod 422. The proximal end of the plunger rod 422 is in the form of an enlarged flanged head 430 (FIG. 41), which is configured to be pressed by a user to eject the liquid 418 from the syringe.

The convertible plunger 420 is configured for operating in two modes. One mode is a sealing mode, like shown in FIGS. 41 and 42A, in which the storage sealing section 132 of the plunger is in its "engagement" position wherein it is compressed between a first portion of the central core of the plunger and the internal wall of the syringe's barrel to form a gas-tight and liquid-tight interface therebetween. The other mode is a gliding mode in which the storage sealing section is shifted to a different portion on the central core, e.g., a "release" position, when the plunger assembly is slid in the barrel so that the storage sealing section is no longer in engagement with the internal wall of the barrel. However, in the gliding mode the liquid sealing section of the plunger will be in sliding engagement with the internal wall of the barrel to form a liquid-tight interface therebetween. Moreover, owing to the inherent lubricity of liquid sealing section, no liquid or other flowable lubricants are necessary to be used in the syringe to facilitate sliding of the plunger in the barrel. This feature constitutes a considerable advantage over the prior art, since the use of a flowable lubricant to facilitate sliding of the plunger may have the effect of contaminating the injectable liquid if the lubricant disassociates from the syringe or plunger into that liquid.

Turning now to FIGS. 26-27, it can be seen that the dispensing sealing section 134 is mounted on the distal end of the plunger's central core 130, while the storage sealing section 132 is located proximally of the liquid sealing section. The storage sealing section 132 is in the form of at least one ring mounted on a portion of the central core and configured so that when the plunger assembly is in the engagement position like shown in FIGS. 41 and 42A, the at least one ring of the storage sealing section 132 forms the heretofore mentioned liquid-tight and gas-tight interface with the interior wall 414 of the syringe's barrel 412. Thus, when the plunger assembly is in that position the storage sealing section provides CCI for the syringe. In the exemplary embodiment shown in FIG. 41 the storage sealing section carries a seal ring 140 of circular cross-section. Other single rings of various cross-sectional shapes may be provided to form the storage sealing section. In fact, multiple rings of various cross-sectional shapes may be provided to form the storage sealing section. For example, optionally, the O-ring has more than one rib or lobe; e.g, 42 ribbed or 43 ribbed O-rings are contemplated. Some of those alternative embodiments for the storage sealing section will be discussed later.

The central core 130 of the convertible plunger 424 is an elongated member having a cylindrically shaped mounting projection 440 at the distal end thereof. The projection 440 can be of any suitable shape. In the exemplary embodiment shown it is semi-spherical. The projection 440 serves as the means for mounting the dispensing sealing section 134 on the distal end of the central core 130. A flange 442 projects radially outward from the central core immediately proximally of the projection 442. An annular recess 444 is provided in the central core immediately proximally of the flange 442. The recess 444 is configured to receive and hold the at least one ring 140 in a "holding" position when the plunger assembly 424 is in the storage mode, i.e., the state shown in FIG. 25. To that end, the recess 444 is preferably of a mating shape to the cross-sectional shape of the ring 140.

The ring 140 is formed of a resilient material or one or more resilient materials, including, but not limited to, a thermoset rubber (e.g., butyl rubber), a thermoplastic elastomer (TPE), liquid silicone rubber and fluoro-liquid silicone rubber. The diameter of the central core 130 at the location of the recess 444 is greater than the normal internal diameter of the ring 140. Thus, when the ring 140 is disposed within the recess 444 it is stretched from its normal outer diameter (i.e., its "constricted" state) to its "expanded" state. In that expanded state the outermost portion of the periphery of the ring will be in intimate engagement with the inner surface 414 of the barrel, thereby forming the heretofore mentioned gas-tight and liquid-tight interface therebetween. As should be appreciated by those skilled in the art, when the ring 140 is in such engagement with the inner surface of the barrel "sticktion," can result. Thus, the convertible plunger of this invention is constructed to enable the ring 428 to move with respect to the central core 130 to enable the plunger assembly to be moved to the release position wherein it operates in the heretofore mentioned gliding mode. When in that mode, the ring 140 will be in a constricted state, wherein the outside diameter of the ring is less than the inner diameter of the interior surface 414 of the barrel's wall 412 so that the ring does engage that interior surface and hence will not interfere with the sliding movement of the plunger assembly into the barrel.

In order to enable the O-ring 140 to move from its engagement position (wherein it will be retained within the annular recess 444) to the release position (wherein it moves out of the annular recess 444), the central core 130 includes a conical tapering section 446 located immediately adjacent the annular recess 444. The proximal end of the conically tapering section 446 terminates in a cylindrical section 448, whose external diameter is less than the internal diameter of the annular recess 444. Thus, when the plunger assembly 420 is pressed to cause it to move in the distal direction shown by the arrow in FIG. 26 within the barrel 412, the frictional engagement between the O-ring and the inner wall of the barrel will tend to hold the O-ring at that longitudinal position in the barrel, while the central core 130 moves distally. Thus, there will be relative movement between the O-ring 140 and the central core in the axial direction. That relative axial movement causes the O-ring 140 to exit the recess 444 from its holding position so the O-ring slides in the proximal direction with respect to the central core in the direction of the arrows 450 in FIG. 26, whereupon the radially outer-most surface of the O-ring will no longer be in engagement with inner surface 414 of the barrel. As such, the plunger assembly 420 can be slid smoothly down the barrel with minimal force. Continued pressing of the plunger assembly will ultimately bring the O-ring into engagement with the undersurface of a projecting flange 452 forming the distal end of the central core 130.

As mentioned above, when the plunger assembly is in the glide mode, the dispensing sealing section 134 will be in sliding engagement with the inner surface 414 of the barrel to result in a good liquid-tight interface therebetween. To that end, the dispensing sealing section 134 basically comprises an elastomeric body or head 454 having an exterior surface portion having a lubricity that is greater than the lubricity of the interior wall 414. The first surface portion may be in the form of a film 456 which extends about the entire exterior surface of the head 454. The film may have an optional thickness of under approximately 4100 micrometer (μm), optionally from 425-50 μm. A variety of different materials may be employed for the film, such as, for example, an inert fluoropolymer, including, fluorinated ethylene propylene (FEP), ethylene tetrafluoroethylene (ETFE), polytetrafluoroethylene (PTFE), ethylene perfluoroethylenepropylene (EFEP), ethylene chlorotrifluoroethylene (ECTFE), Polychlorotrifluoroethene (PCTFE), perfluoroalkoxy (PFA), among other coatings. Optionally, CPT fluoropolymer may be used. CPT is a modified perfluoroalkoxy (PFA) commercially available from Daikin America, Inc. and generally comprises the addition of PCTFE side chains to a PFA main chain during polymerization, thereby increasing gas and/or liquid barrier properties of standard PFA. Optionally, the exterior surface of the head 454 may be in the form of a rigid cap (not shown) formed of a perfluoropolyether oil, such as DEMNUM which is commercially available from Daikin America, Inc., which may be mixed with resin and extruded into a film, mold or cap. Additionally, according to certain embodiments, the material used for the film coating may not be an expanded fluoropolymer. Further, according to certain embodiments, additives may be added to the material for the film or cap, such as additives that may improve the adhesion of the film or cap to the underlying portion of the plunger making up the liquid sealing section and/or decrease the friction between that section and the sidewall of the barrel. Additionally, according to certain embodiments, an adhesion promoting coating or process may be employed, such as, for example, a corona treatment. For some applications, it may be desirable to coextrude different materials to form the film. For example, coextruded film combinations may include a cyclic olefin copolymer (COC) with Aclar, Polyethylene (PE) with Aclar and FEP with PE, among other combinations.

Optionally, after the film material has been inserted into the mold, the plunger material is injected into the mold. Thus, in the final product, the liquid sealing section of the plunger may comprise a plunger core, a polymer head disposed on the tip of the plunger core and a film covering the head. Alternatively, a high durometer, lubricious TPE material without any film disposed thereon may be used as the liquid sealing section.

In the case where a film 456 is used to provide the lubricious outer surface of the liquid sealing section, the film may be secured to the head 454 in various ways. For example, as shown in FIG. 27 a sheet of film 456 may be wrapped about the head 454, so that the portions 458 of the sheet of film contiguous with its edges are located within a recess 460 in the head 454, like shown in FIGS. 26-27. The recess 460 is of a mating shape to the shape of the projection 440. Thus, when the projection 440 is inserted into the recess to mount the head 454 on the distal end of the central core 130, the edge portions 458 of the film 456 will be trapped therein. The securement of the head 454 to the central core 130 can be achieved by means of a press fit, compression ribs, or any other suitable means for fixedly securing the head to the central core with the edge portions of the film trapped therebetween.

FIGS. 23 and 24 illustrate an alternative embodiment of the plunger assembly 310, and in particular, an alternative closure 36 configured as an elastomeric sleeve 120, optionally made from a thermoplastic elastomer, having a sidewall 15 and a front face 35 facing the front dispensing opening 26, the sidewall 15 comprising a stretch zone 154 that is adapted to undergo axial elongation to convert the closure 36 from a storage mode to a dispensing mode, wherein the elongation reduces an outer profile of at least a portion of the sidewall 15, thus reducing the closure 36 to a constricted state in the dispensing mode.

The closure 36 includes an insert 362, a connector body 363, and a sleeve 364. As shown in FIG. 23, according to certain embodiments, the sleeve 364 includes a cavity 366 configured to receive placement of the proximal end 22 of the interior shaft 316. The insert 362 may also include a relatively rigid shaft 368 that assists in the displacement of the insert 362 and/or deformation of the closure 36, as discussed below.

According to certain embodiments, the connector body 363 may be molded from a relatively stiff and/or rigid material, such as, for example, polyethylene or polypropylene. Additionally, the connector body 363 may have a first section 365, a second section 367, and a third section 369. The first section 365 of the connector body 363 is configured for a connectable engagement with the exterior shaft 318. For example, the first section 365 may include an internal thread 340 that mates with an external thread 338 of the exterior shaft 318.

According to certain embodiments, the second section 367 of the connector body 363 may provide an internal structure in the closure 36 that minimizes and/or prevents a reduction in the size, such as the width of the sleeve 364 when the closure 36 is inserted into the barrel 356. According to such an embodiment, the sleeve 364 may be sized such that, when the closure 36 is positioned in the barrel 356, the sleeve 364 is compressed, with the support of the second section 367, between the sidewall 358 of the barrel 356 and the second section 367 of the connector body 363. Such compression of the sleeve 364 may result in the formation of a seal, such as, for example, a compression seal, between the closure 36 and the barrel 356 that may be used to maintain the sterility and/or integrity of an injection product stored in the barrel 356. In addition to the second section 367 of the connector body 363, according to certain embodiments, the insert 362 may also be configured to provide support to the sleeve 364 and/or connector body 363 when the closure 36 is inserted into a barrel 356.

Further, according to certain embodiments, one or more ribs 352 of a storage sealing section 351 may extend from the sleeve 364 and be compressed against the sidewall 358 of the barrel 356 to provide CCI during when the plunger is in a "storage mode," e.g., to seal the contents of a pre-filled syringe when in storage, prior to use. The plunger 312' may further include a liquid sealing section 353 comprising at least one rib 355 of the liquid sealing section 353. The purpose of the liquid sealing section 353 is to provide a liquid tight seal both when the plunger 312 is in a storage mode as explained above, and when the plunger is transitioned into a "dispensing mode," i.e., when the storage sealing section 351 reduces or ceases compressive force or radial pressure against the barrel wall 358 so as to facilitate advancement of the plunger to dispense of the contents of the syringe. Preferably, there is a valley 357 separating the storage sealing section 351 from the liquid sealing section 353.

Alternatively, according to optional embodiments, each rib 352, 355 may form a separate seal when compressed against the sidewall 358 of the barrel 356. For example, in the embodiment illustrated in FIGS. 23-24, the sleeve 364 includes two ribs 352, 355 that may be used to form a seal(s) between the sidewall 358 of the barrel 356 and the sleeve 364. Further, according to certain embodiments, the second section 367 and/or insert 126 may be configured to limit the compression of the rib 352 and/or sleeve 364 such that the rib 352 and/or sleeve 364 are not compressed more than 20% of the overall width or diameter of the rib 352 and/or sleeve 364 when the closure 36 is compressed to form a seal in the barrel 356. Optionally, the rib 352 and/or sleeve 364 are compressed less than 10% of the overall width or diameter of the rib 352 and/or sleeve 364 when the closure 36 is compressed to form a seal in the barrel 356, optionally less than 9%, optionally less than 8%, optionally less than 7%, optionally less than 6%, optionally less than 5%, optionally less than 4%, optionally less than 3%, optionally less than 2%, optionally from 3% to 7%, optionally, from 3% to 6%, optionally from 4% to 6%, optionally from 4.5% to 5.5%, optionally from 4.5% to 5.5%, optionally about 4.8%.

The third section 369 of the connector body 363 may provide a surface upon which the insert 362 may exert a force against to elongate the length, and thereby reduce the width when injection product is to be dispensed from the barrel 356.

More specifically, when the injection product is to be dispensed from the barrel 356, the interior shaft 316 may be displaced from the first position, as shown in FIG. 23, to a second position, as previously discussed. As the interior shaft 316 is displaced toward the second position, the proximal end 22 of the interior shaft 316 exerts a pushing force upon an insert 362, such as, for example, upon the shaft 368 of the insert 362. As the interior shaft 316 exerts a force upon the insert 362, the insert 362 is displaced within the sleeve 364 generally in the direction of the proximal end 361 of the barrel 356, and thus at least a portion of the outer surface 370 of the insert 362 pushes against the third section 369 of the connector body 363. As the insert 362 is displaced and presses upon the third section 369, the second section 367 of the connector body 363 is elongated, thereby changing the prior accordion shape of the second section 367 to a generally straighter or flatter configuration. Additionally, the sleeve 364 is also elongated by this displacement of the insert 362 in the sleeve 364, resulting in the width of the sleeve 364 and thus convertible closure 36 being reduced. The reduction in the width of the sleeve 364/convertible closure 36 results in a reduction in the compressive force that had been used to form the seal between the convertible closure 36 and the sidewall 358 of the barrel 356. In other words, slight axial stretching of the sleeve 364 (optionally achieved by displacing the insert 362 from a deactivated position to an activated position) in turn reduces the width of the sleeve 364 and convertible plunger 312', thus resulting in reduction in the compressive force that had been used to form the seal between the convertible plunger 312' and the sidewall 358 of the barrel 356.

Thus, with the width of the sleeve 364/convertible closure 36 reduced, the force necessary to displace the convertible closure 36 in the barrel 356 may also be reduced. Further, as previously discussed, as the interior shaft 316 may be locked in the second position by the locking tab 24, the sleeve 364 may maintain the elongated shape while the injection product is dispensed from the barrel 356.

Another stretching plunger embodiment is shown in FIGS. 28-32.

Figure 28:
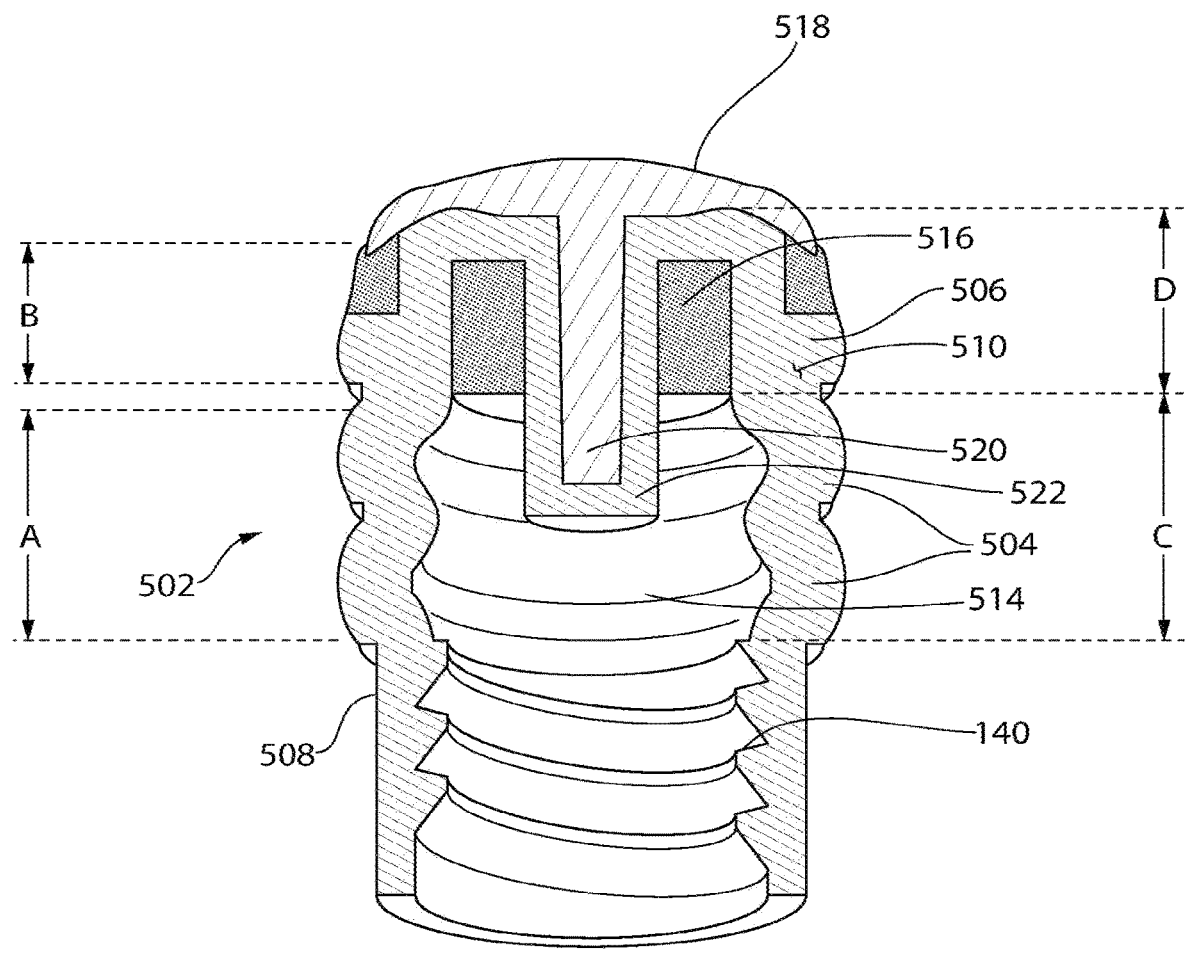
FIG. 28 is an axial sectional view of one exemplary plunger constructed in accordance with this invention.
Figure 29:
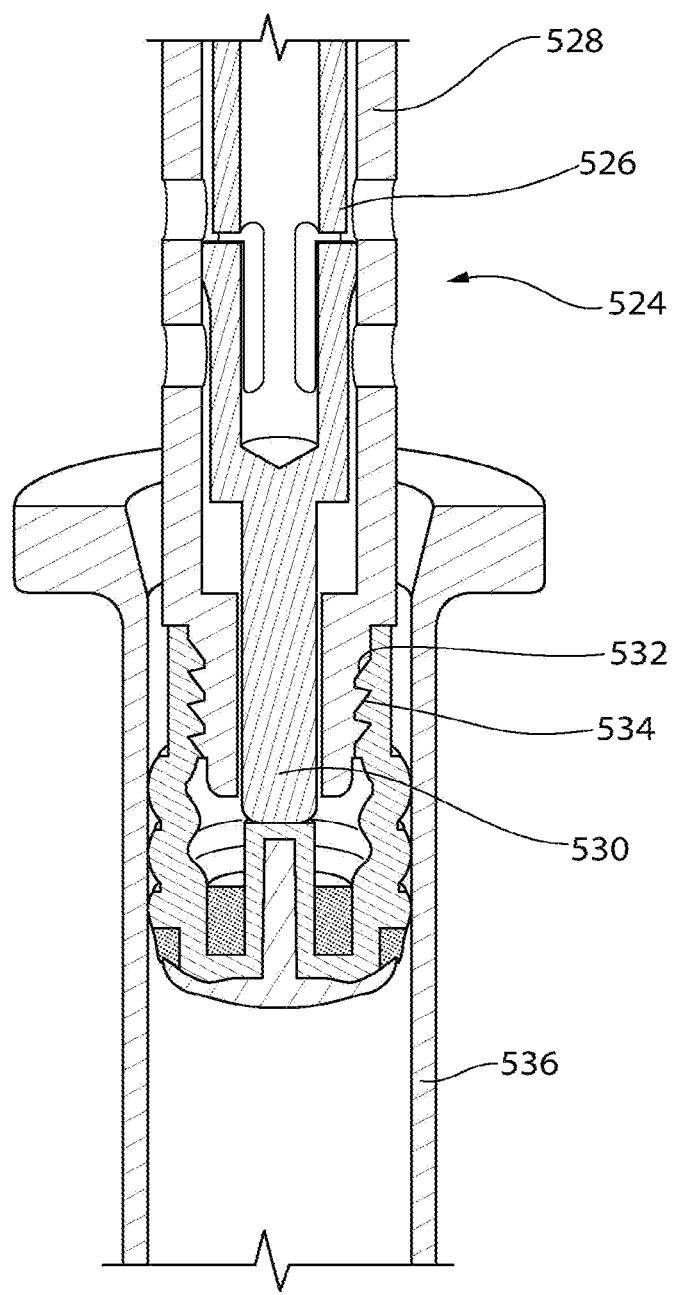
FIG. 29 is an enlarged axial sectional view of the plunger of FIG. 1 having a plunger rod attached thereto and disposed within a syringe barrel.

Referring now to FIGS. 28 and 29, there is shown an exemplary plunger 502 constructed in accordance with this invention. The plunger 502 comprises a sleeve 510 that is preferably made from a thermoplastic elastomer (TPE). Such TPE materials may include, but are not limited to, TPE materials from KRAIBURG TPE GmgH & Co. (e.g., THERMOLAST®, HIPEX® or COPEC®), SANTOPRENE, or from POLYONE GLS (e.g., ONFLEX, VERSAFLEX, DYNAFLEX, DYNALLOY, VERSALLOY, VERSOLLAN or KRATON®). The TPE subfamily of thermoplastic vulcanizate (TPV) may be particularly preferred for some applications.

The sleeve 510 may include an internal thread 512. The first end 28 of the exterior shaft 528 of the plunger rod 524 may include an external thread 532 that is configured to mate with an internal thread 512 of the sleeve 510. The sidewall 142 of the sleeve optionally comprises a storage sealing section A comprising two storage sealing ribs 504 (although additional or fewer sealing ribs are also contemplated) that provide CCI to a drug product contained in a medical barrel when the plunger 502 is in the storage position. The plunger further comprises a liquid sealing section B optionally comprising one rib 506 (although additional sealing ribs are also contemplated). The liquid sealing section B is configured to provide a liquid tight seal when the plunger 502 is in storage mode and when the plunger is transitioned into a "dispensing mode." The dispensing mode is initiated when the storage sealing section A reduces or ceases providing compressive force against the barrel wall 58, so as to facilitate easier advancement of the plunger to dispense the contents of the syringe. Optionally, the liquid sealing section B itself also provides CCI. However, it is contemplated that the storage sealing section A, when the plunger 502 is in storage mode, provides an additional "zone of sterility".

The plunger 502 further comprises a cap 518 covering the nose cone adjacent to the liquid sealing section B. Optionally, the cap 518 covers none of, some of or all of the liquid sealing section B. The cap 518 is preferably made from an injection moldable thermoplastic material that is rigid in finished form, e.g., polypropylene (PP), a cyclic olefin polymer (COP), cyclic olefin copolymer (COC), polycarbonate, polyacrylonitrile (PAN), polyethylene terephthalate (PET), polybutylene terephthalate (PBT), polyoxymethylene acetal (POM) or polyethylene terephthalate glycol-modified (PETG). Optionally, the cap 518 may be made from fluoropolymers such as, for example, high density polyethylene (HDPE), low density polyethylene (LDPE), or PTFE, among others. Optionally, the cap 518 is an injection moldable part that is assembled onto the sleeve 510. Optionally, the cap 518 and sleeve 510 are made through a two-shot molding process.

The cap 518 may include an elongated stem 520 extending into the sleeve 510. Optionally, the sleeve 510 includes a stem cover 522 which receives and retains (e.g., through interference fit, adhesive, two-shot molding, and/or other means) the stem 520, thereby securely retaining the cap 518 on the sleeve 510.

The sleeve 510 preferably includes an internal hollow portion 514 and an internal solid portion 516 that is optionally proximal to the internal hollow portion 514. The internal hollow portion 514 defines a stretch zone C, which is configured to facilitate stretching of the sleeve 510 in an axial direction when the plunger 502 is actuated, as further described below. The internal solid portion 516 defines a non-stretch zone D, which is configured to resist or prevent stretching in an axial direction of the sleeve 510 when the plunger 502 is actuated.

To actuate the plunger 502, a user may apply downward pressure onto the interior shaft 526 of the plunger rod 524. Such pressure transfers onto the stem cover 522, the stem 520 and the cap 518. Since the cap 518 is secured to or integral with the sleeve 510, the initial movement of the interior shaft 526 does not at first displace the plunger 502 down the barrel; rather such initial movement causes the cap 518 to pull on and thus slightly stretch the stretch zone C of the sleeve 510 in an axial direction, while at the same time not stretching the non-stretch zone D. In so doing, the width of the plunger 502 is reduced slightly in the stretch zone C (albeit not in the non-stretch zone D), thus reducing the plunger 502 from an expanded state to a constricted state, or from storage mode to dispensing mode. Once in dispensing mode, the plunger 502 is preferably configured to provide a desirable and substantially constant plunger force, e.g., under 15N, as discussed above.

Figure 30:
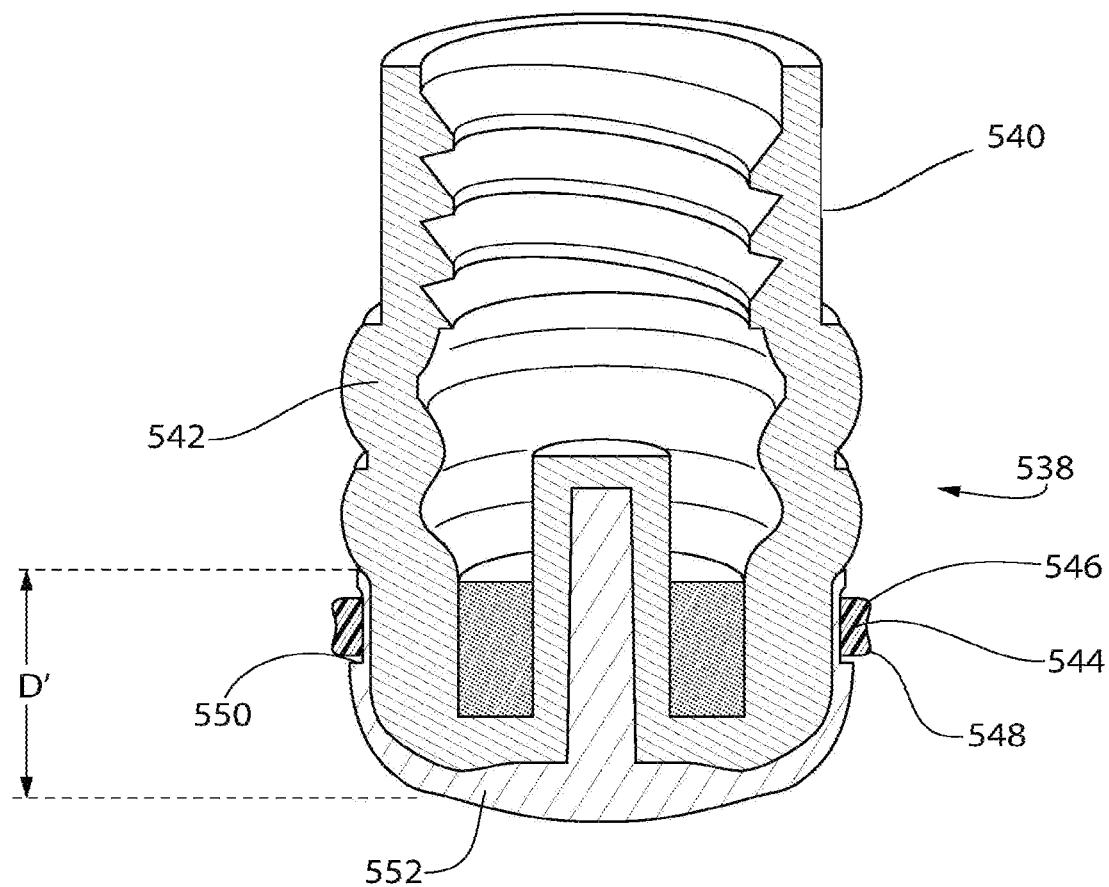
FIG. 30 is an axial sectional view of another exemplary embodiment of a plunger constructed in accordance with this invention.
Figure 31:
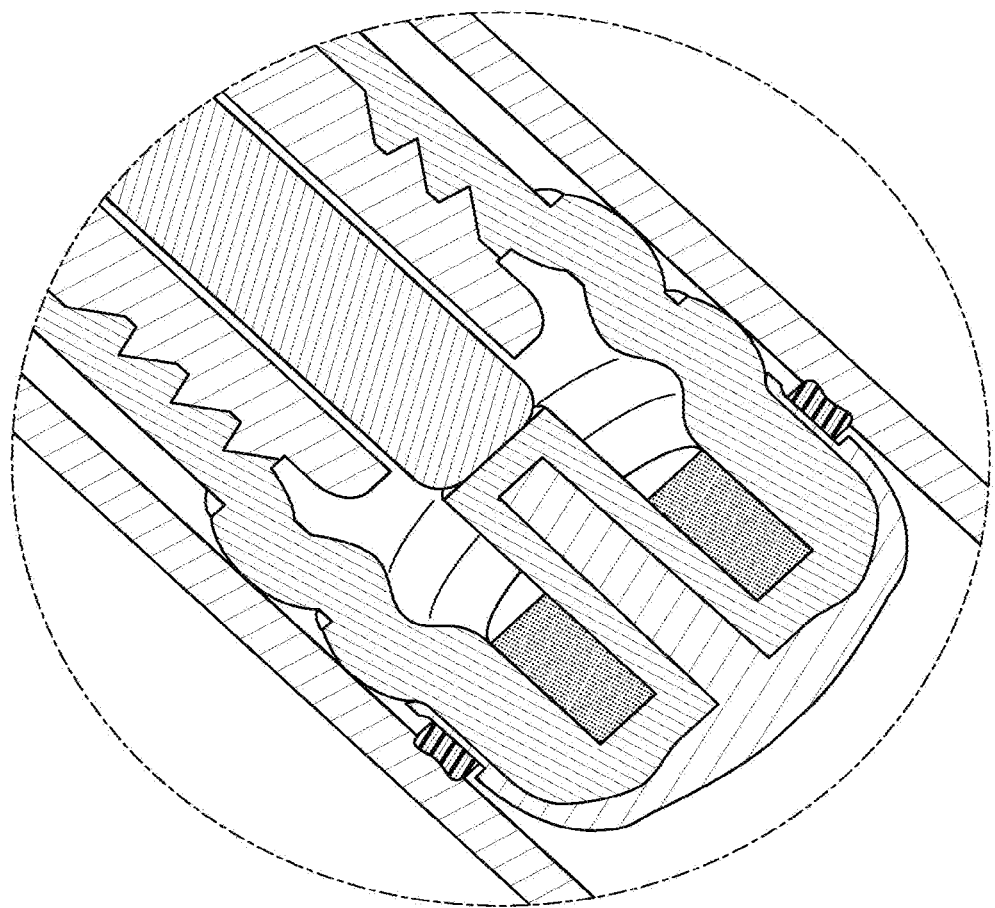
FIG. 31 is an enlarged axial sectional view of the plunger of FIG. 3 having a plunger rod attached thereto and disposed within a syringe barrel.

Referring now to FIGS. 30-31, there is shown another exemplary embodiment of a plunger 538 constructed in accordance with this invention. In many respects, the plunger 538 is similar in structure and operation to the plunger 502 described above. For the sake of brevity, the features common to both plungers 502, 538 will not be repeated here. However, differences will be highlighted.

The plunger 538 includes a cap 552 that covers the entire nose cone of the sleeve 542 and a portion of the sidewall 540 of the sleeve 542 in the area of the liquid sealing section B of the plunger 538 above. The cap 552 includes an annular gap 550 around its periphery. Disposed within the annular gap 550 and extending slightly radially therefrom is a liquid sealing member 544, optionally an O-ring. The liquid sealing member 544, as shown, includes two annular miniature ribs 546, 548. It is contemplated that these miniature ribs 546, 548 provide sufficient sealing, while at the same time providing minimal surface area to enable a low plunger force when the plunger 538 is advanced in the barrel in dispensing mode.

Since the liquid sealing member 544 is disposed about the plunger's non-stretch zone D', the liquid sealing member 544 is not converted or otherwise reduced in diameter or radial pressure, during dispensing mode. In other words, it is contemplated that the liquid sealing member maintains the same diameter and level of outward radial pressure, regardless of whether the plunger 538 is in storage mode or dispensing mode.

Preferably, the liquid sealing member 544 is made from a material that provides a good oxygen barrier, preferably a thermoset elastomer.

Figure 32:
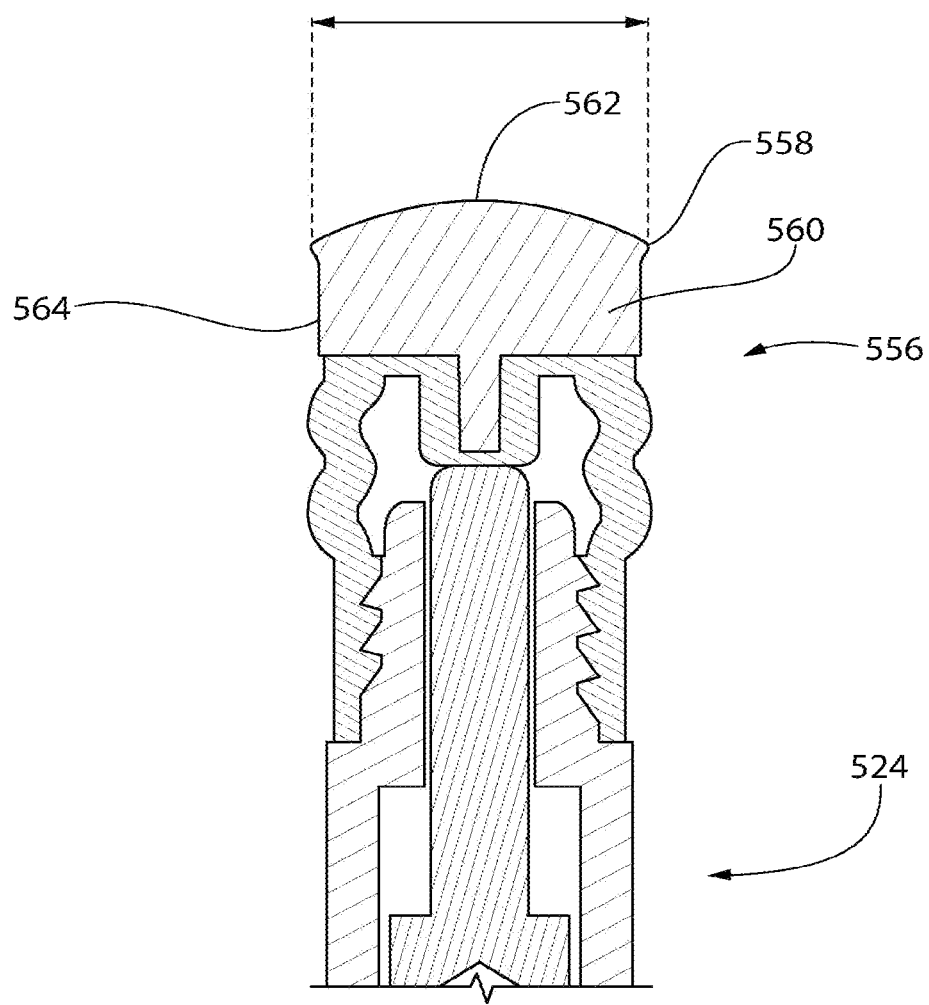
FIG. 32 is an enlarged axial sectional view of yet another exemplary embodiment of a plunger constructed in accordance with this disclosure, having a plunger rod attached thereto.
Figure 33:
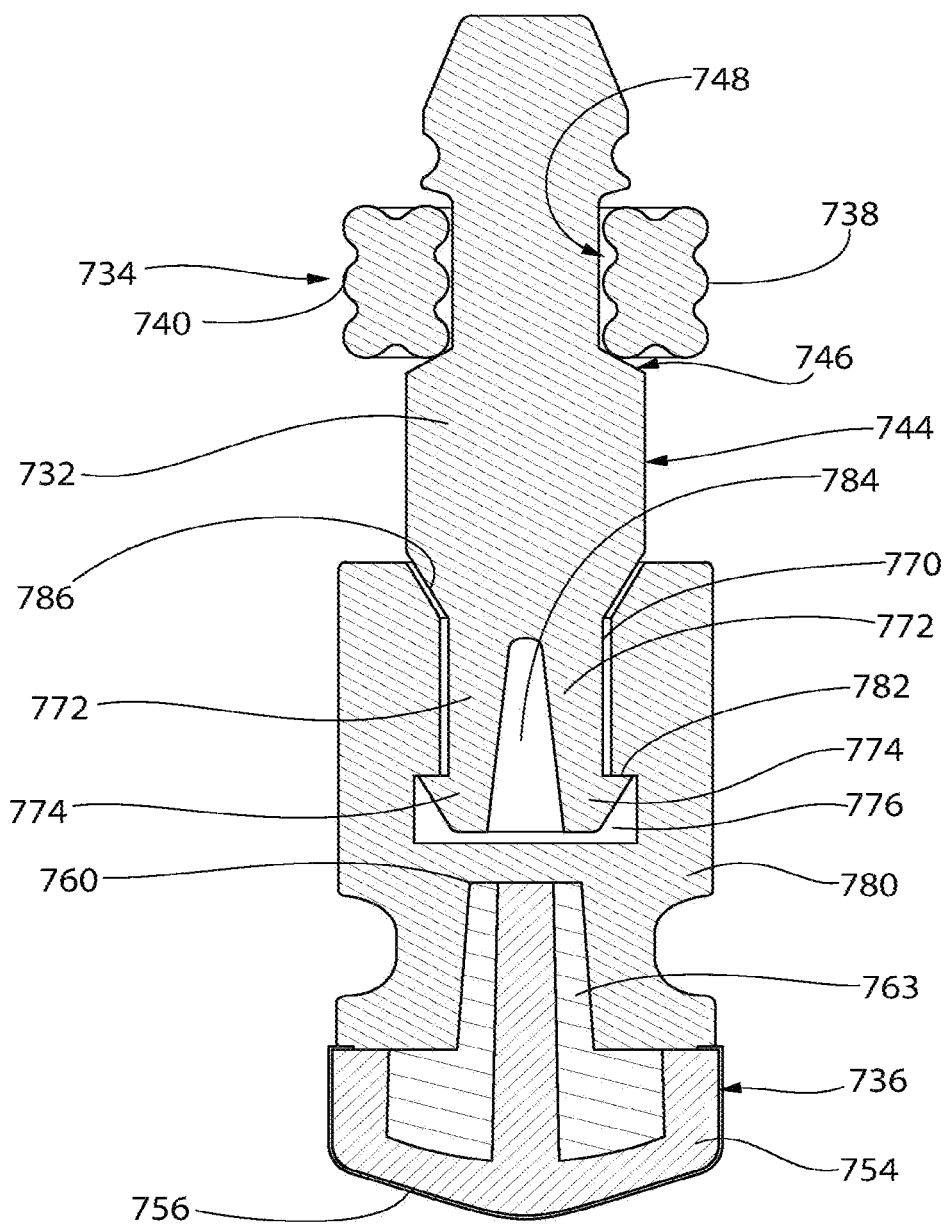
FIG. 33 is an axial sectional view of an alternative convertible plunger embodiment comprising a connector, which is at a distal end secured to the liquid sealing section and at a proximal end, secured to the central core.

Referring now to FIG. 32, there is shown another exemplary embodiment of a plunger 556 constructed in accordance with this invention, having a plunger 524 rod attached thereto. In many respects, the plunger 556 is similar in structure and operation to the plunger 502 described above. For the sake of brevity, the features common to both plungers 502, 556 will not be repeated here. However, differences will be highlighted.

The plunger 556 includes a cap 560 that is much thicker than other cap embodiments disclosed herein. The cap 560 functions as the liquid sealing section B' for the plunger 556. The cap 560 preferably includes an arced nose cone 562 and a substantially cylindrical sidewall 564. The sidewall 564 slightly flanges out radially as it approaches the nose cone 562 to define an annular cap rib 558. The cap rib 558 preferably provides a very slight interference fit with the inner diameter of the barrel. For example, it may be desired for some applications that the inner diameter of the barrel is 15-20 micrometers (μm) smaller than the diameter of the cap rib 558. Since the cap 560 is made from a rigid polymer (any of the materials described herein for other cap embodiments may be suitable), the head of the cap (as opposed to the stem) provides a zone of zero deformation, i.e., a non-stretch zone D". Thus, when the plunger 556 is actuated and converted from storage mode to dispensing mode, the cap 560 does not experience reduction in diameter or radial pressure during dispensing mode. It is contemplated that the annular cap rib 558 provides CCI (sterility), oxygen barrier and liquid tight sealing. This level of sealing is provided by the cap rib 558 alone during dispensing mode. However, during storage mode, the storage sealing ribs on the sleeve of the plunger 556 provide an additional zone of sterility, which is not disrupted until releasing the plunger 556 out of storage mode, in the manner described above regarding the plunger assembly 10 of FIGS. 28-29.

Optionally, instead of plungers that are convertible upon stretching, it is contemplated that some embodiments of the invention may include plungers that do not stretch. For example, one modification may be use of the polymer plunger cap 560 without it being secured to a TPE sleeve. In other words, the plunger cap 560 itself may serve as a plunger without undergoing any substantial deformation through use (i.e., not converting from a storage mode to dispensing mode).

An alternative embodiment of a convertible plunger 724 is shown in FIGS. 33-35C. The plunger 724 is, to some extent, structurally and functionally similar to the plunger assembly 324 of FIGS. 19-22, although there are important differences to the construction and assembly of the plunger 724. Like its counterpart in FIGS. 19-22, the convertible plunger 724 is configured for operating in a sealing mode (wherein the storage sealing section in an engagement position) and gliding mode (wherein the storage sealing section is shifted to a release position), substantially as described above. Also, the convertible plunger 724 is of the independent storage sealing section plunger type. For the sake of brevity, similar features as between the two embodiments (e.g., material and configuration of the storage ring, the manner in which the plunger is secured to a plunger rod, the basic function of the plunger, etc.) will not be discussed in great depth here. However, differences may be noted. The convertible plunger comprises a ring carrier in the form of a rigid central core 732, which would be coaxial with the central axis of a syringe barrel when assembled into a syringe (e.g., the syringe barrel 12 of FIG. 4).

The storage sealing section 734, in the form of a storage ring 738, optionally, as shown, including two, three, or more lobes 740, is mounted on a portion of the central core 732. The central core 732 is an elongated rigid member comprising, from the proximal end thereof, a flange 752 (which may be secured to a plunger rod, e.g., via threaded engagement or snap fit) which is adjacent to an annular dispensing platform 748. Distal to the dispensing platform 748 is an annular gradual transition region 746 which leads to the annular storage platform 744. The outer diameter of the central core 732 narrows distally to the storage platform 744 to form two resilient prongs 772 of an annular insertion platform 770, the function of which is described below.

Unlike the embodiment of FIGS. 19-22, the central core 732 is mounted to the proximal end of a connector body 780 (as opposed to the proximal end of a storage sealing section 336). The connector body 780 is a preferably rigid (e.g., polymeric) and generally cylindrical member, the proximal end of which receives and connects to the resilient prongs 772 of the central core 732. The liquid sealing section 736 is mounted to the distal end of the connector body 780 in essentially the same way as the liquid sealing section 336 mounts to the central core 332 of FIGS. 19-22. The description above with respect to the liquid sealing section 336 will suffice for description of the same vis-à-vis the plunger 724 of FIGS. 33-35C. It will only be briefly noted that the liquid sealing section 736 optionally comprises a head 754 having a film 756 wrapped thereon. Notably, the film 756 is wrapped entirely around the head 754 and continues along an underside of the head 754, wherein the film 756 is sandwiched between the head 754 and the connector body 780. The head 754 comprises a stem 763 that is assembled and secured into a central mating recess 760 of the connector body 780, e.g., by ultrasonic welding, an adhesive, a press-fit, a snap-fit or through threaded engagement.

Optionally in any embodiment, the film 756 can be a Fluro-Tec® film laminate. As another option, the film 756 can be a coating sold under the trademark I-Coating® by Terumo Corporation. Optionally in any embodiment, the film 75 can be "formed of a composition which does not contain solid fine particles and contains a silicone-based resin which is a product formed by addition reaction between silicone having a vinyl group and silicone having a hydrogen group bonded to a silicon atom." "In an exemplary embodiment, the composition forming the coating layer contains a platinum group metal based catalyst." US 2013/0030380 A1, p. 2.

The connector body 780 comprises an axial channel 784 leading to a wider opening 776 that optionally bores entirely through a center portion of the connector body 780, in a direction perpendicular to the central axis of the axial channel 784. This configuration simplifies injection molding of the connector body 780. The opening 776 comprises a ridge section 782 adjacent to where the axial channel 784 meets the opening 776. The prongs 772, at their distal ends, comprise radially outward projecting abutments 774. The abutments 774 are retained underneath the ridge section 782 to secure the central core 732 to the connector body 780.

To assemble the central core 732 to the connector body 780, the two components should be aligned and axially centered. The prongs 772 of the central core 732 are then inserted into the axial channel 784 of the connector body 780. The axial channel 784 is configured to facilitate the insertion of the prongs 772, e.g., with an annular chamfer 786 at the proximal end of the axial channel 784. When the prongs 772 contact the chamfer 786, the prongs 772 are urged to resiliently flex or compress radially inward so that the prongs 772 and abutments 774 fit entirely within the axial channel 784 as the prongs 772 are moved distally into the axial channel 784. Once the abutments 774 fully reach the wider opening 776, the prongs 772 are released from their compressed state and the abutments 774 are retained underneath the ridge section 782, preventing the central core 732 from being separated from the connector body 780. In short, the prongs 772 secure the central core 732 to the connector body 780 in a snap-fit configuration. This provides advantages during assembly of the plunger 724 into a syringe barrel, as explained now.

Figure 34A:
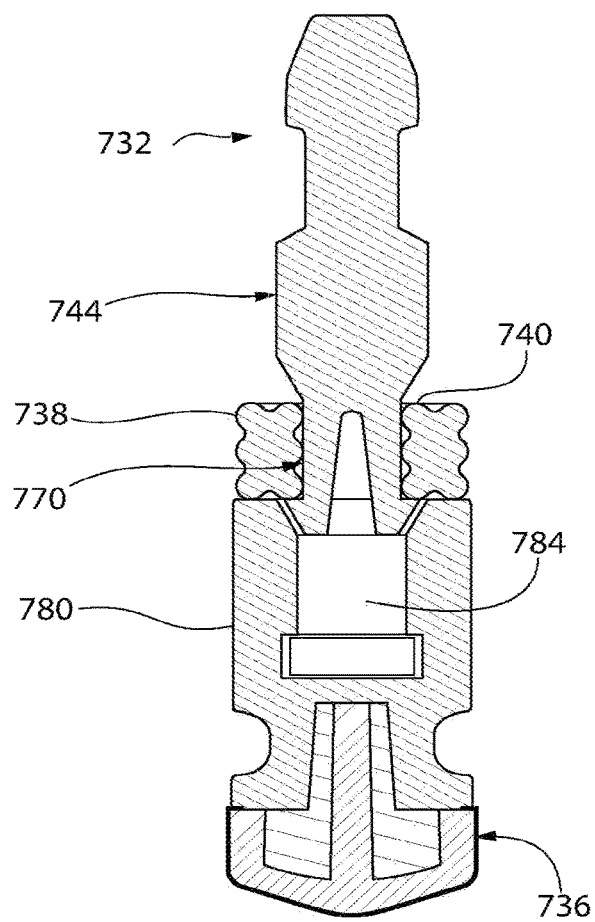
FIGS. 34A and 34B are schematic drawings illustrating the manner in which the convertible ring of FIG. 33 is assembled.
Figure 34B:
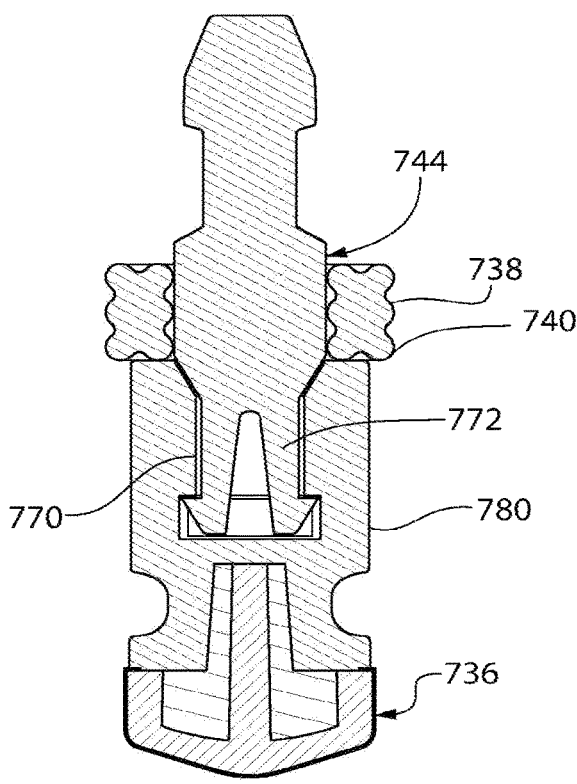

FIGS. 34A and 34B are schematic drawings illustrating the manner in which the storage ring 738 via the central core 732 are assembled onto the connector body 780 and liquid sealing section 736 subassembly, thus forming a completed convertible plunger 724. FIG. 34A shows the components just prior to fully assembling them to form the plunger 724. As shown, the distal end of the central core 732 is protruding slightly into the axial channel 784 of the connector body 780 and is thus not yet secured thereto. Notably, in this position, the storage ring 738 is disposed on the annular insertion platform 770 of the central core 732 or ring carrier. The annular insertion platform 770 has a narrower outer diameter than the annular storage platform 744. As such, the outer diameter of the storage ring 738 is correspondingly less than the ring's 738 outer diameter when disposed on the storage platform 744, as shown in FIG. 34B. The comparatively small outer diameter of the storage ring 738, when disposed about the insertion platform 770, is configured to facilitate insertion of the ring 738 into a syringe barrel in such a way that the ring 738 does not contact the barrel wall or has only minimal contact with it. When on the insertion platform 770, the sealing ring 738 is in a "load position" wherein the ring 738 slides easily into the proximal end of the syringe barrel. As the prongs 772 are urged downward into the axial channel 784 of the connector body 780 to ultimately secure the central core 732 thereto (as shown in FIG. 34B), the storage ring 738 transitions from load position on the insertion platform 770 to engagement position, wherein the ring is disposed about the storage platform 744.

Notably, with the aforementioned process, the ring 738 is not separately urged or pushed with a device to set the ring 738 into engagement mode. Rather, the ring 738 is inserted into the syringe barrel with little or no barrel sidewall resistance by placing the ring in load position on the central core 732 before mounting the central core 732 to the connector body 780. As seen in both FIGS. 34A and 34B, the ring 738 is flush against the proximal end of the connector body when the ring is in load position and in engagement position. In other words, the ring 738 remains in a fixed position during loading while central core 732 moves relative to the ring. With no space between the ring 738 and the connector body 728 both before and after the ring 738 compresses against the barrel sidewall, there is no "pressure zone" between the storage ring 738 and the liquid sealing section 736.

This design, therefore, addresses the problems identified above with loading the storage ring without distorting it or creating an unwanted pressure zone.

Figures 35A, 35B, 35C:
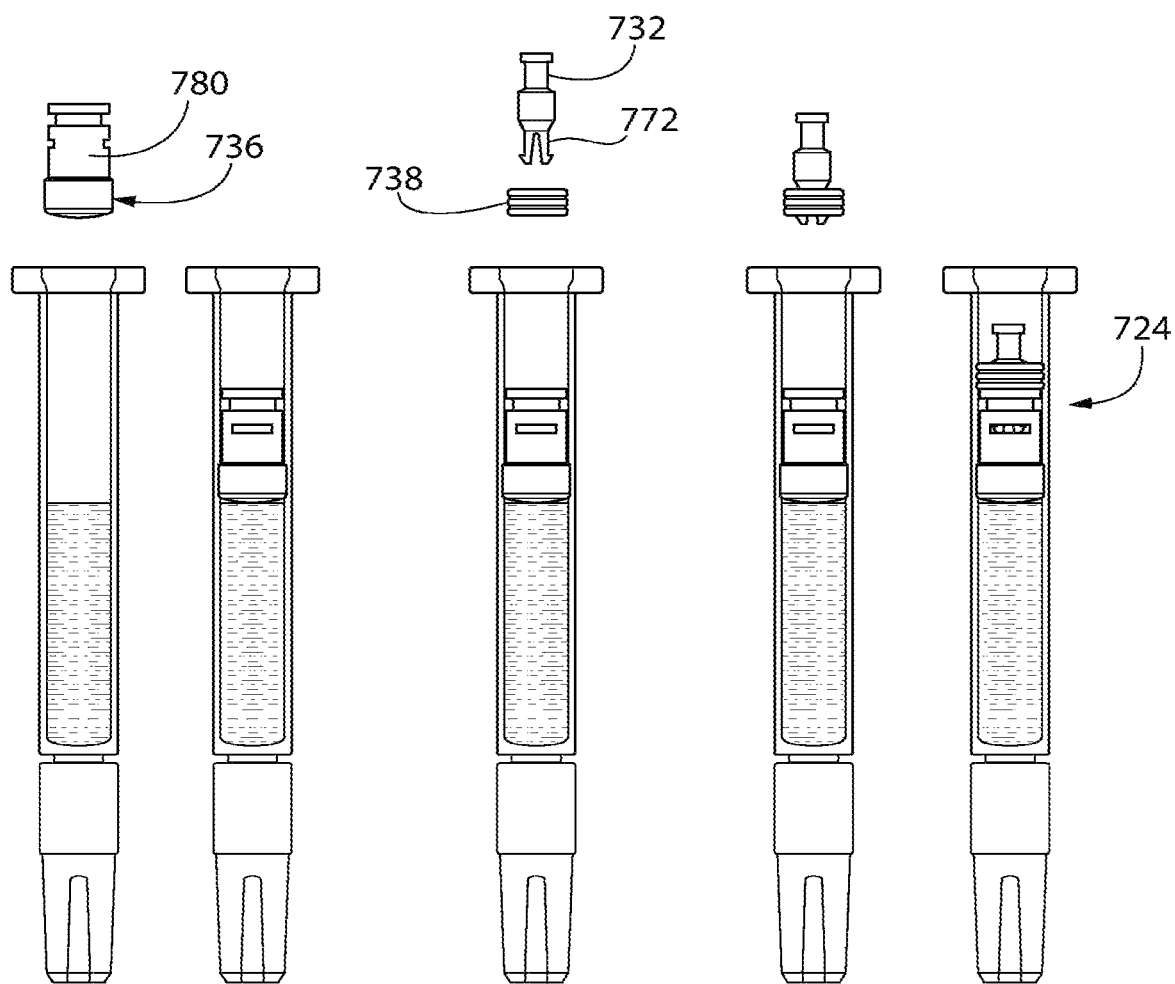
FIGS. 35A-35C are schematic drawings illustrating the manner in which the convertible plunger components of FIG. 33 are loaded into and assembled within a syringe barrel.

The schematic drawings of FIGS. 35A-35C more fully illustrate the manner in which the components of the convertible plunger 724 may be loaded into a prefilled syringe and assembled.

As shown in FIG. 35A, the liquid sealing section 736 and connector body 780 subassembly may be loaded into the plunger via traditional methods to load plungers. These include vent tube, vacuum loading and vacuum assist, all of which are described, below. Next, the storage ring 738 and central core 732 subassembly is created by disposing the ring 738 in load position 738 on the prongs 772 of the central core 732. As shown in FIG. 35C, the storage ring 738 and central core 732 subassembly is inserted, e.g., by push-rod or by a plunger rod assembled thereto, until the snap-fit is established with the connector body 780 to form the fully assembled convertible plunger, loaded in engagement mode. It is contemplated that liquid prefilled in the barrel provides resistance necessary to oppose the downward force applied when assembling the central core 732 to the connector body 780. The plunger 724 then may be used, just as described with other embodiments, to convert the plunger 724 from engagement position (shown in FIG. 35C) to release position (shown in FIG. 33).

Optionally, for any plunger embodiments comprising a cap, the cap is coated with a barrier coating or layer to provide a gas barrier between contents of a syringe and the ambient environment. Optionally, at least one organo-siloxane coating or layer may be applied on top of the barrier coating or layer to protect the barrier layer from being degraded by syringe contents having a pH broadly within the range of 5 to 9. Optionally, a tri-layer coating set may be applied to the cap. These coatings, layers and coating sets are preferably applied via chemical vapor deposition, more preferably plasma enhanced chemical vapor deposition, as described elsewhere in this specification.

Optionally in any embodiment, as the vessel 14, a syringe barrel having a front dispensing opening 26 and a back opening 32 can be provided.

Optionally in any embodiment, the vessel 14 is a syringe barrel and the closure 36 is a plunger disposed in the vessel 14 and having an area of contact with the vessel 14, the pre-filled pharmaceutical package 210 further comprising a coating or layer of a crosslinked silicone lubricity coating or layer 287, optionally a plasma crosslinked silicone lubricity coating or layer 287, disposed on one of the vessel 14 and the closure 36 at the area of contact between the vessel 14 and the closure 36.

Optionally in any embodiment, the pre-filled pharmaceutical package 210 comprises a tamper-evident needle shield 28.

Optionally in any embodiment, a pre-filled pharmaceutical package 210 comprises a luer lock 788 on the vessel 14.

Figure 38A:
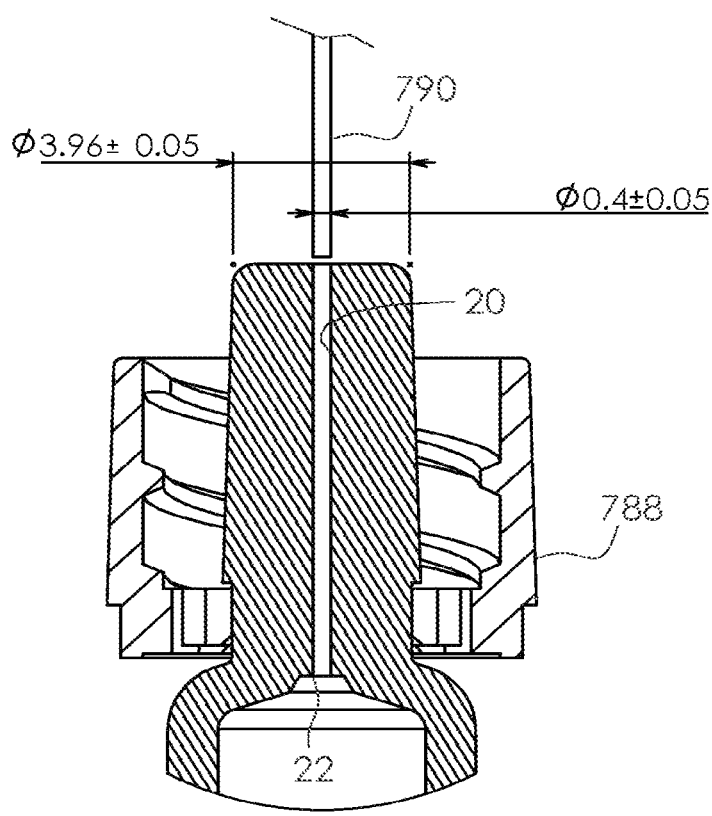
FIG. 38A shows, in an enlarged detail view of FIG. 38B, a luer lock syringe with a 0.4 mm inner diameter luer capillary with low dead volume, which optionally can be used in any embodiment of the present invention.

Optionally in any embodiment, with reference to FIG. 38A, a dispensing portion 20 can be provided through a luer lock 788, the dispensing portion 20 having a diameter of from 0.05 mm to less than 1.8 mm, alternatively from 0.1 mm to 1.5 mm, alternatively from 0.3 mm to 1.8 mm, alternatively from 0.3 mm to 1.5 mm, alternatively from 0.4 mm to 0.8 mm, alternatively from 0.5 mm to 0.7 mm, alternatively 0.4 mm, 0.5 mm, or 0.6 mm. This small dispensing opening 20 is contemplated to reduce the waste volume in the syringe which will contain residual drug after administration from a luer lock syringe, which is important for expensive drugs.

Figure 5:
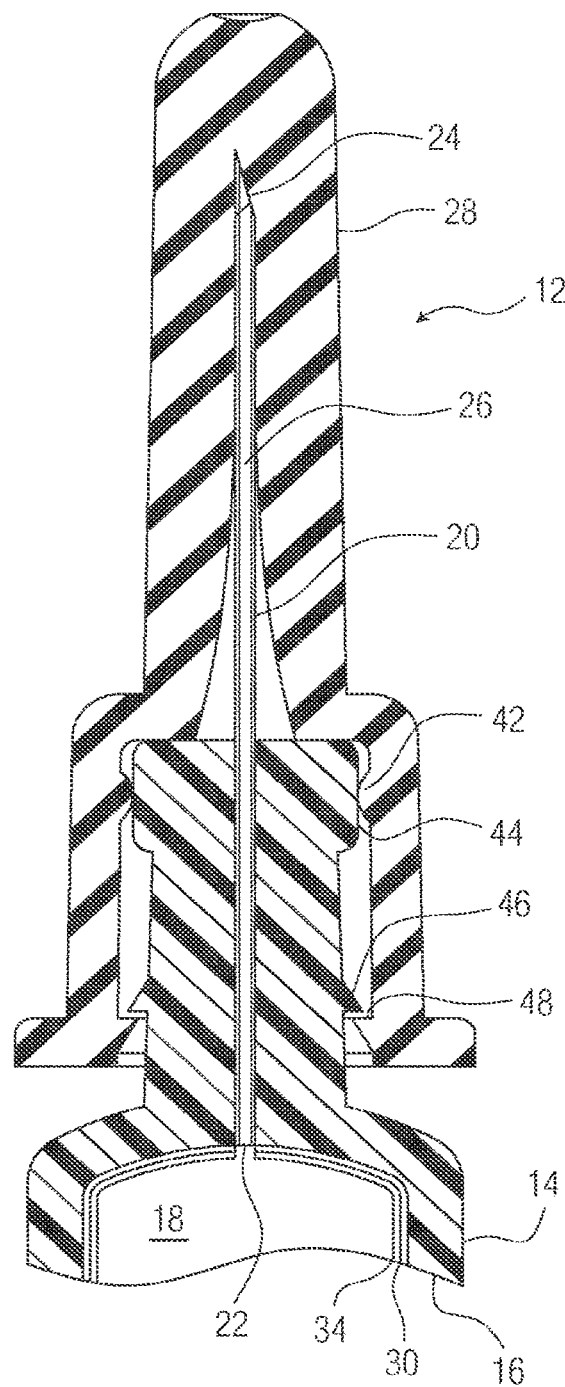
FIG. 5 is an enlarged fragmentary view of the capped assembly of FIG. 3.
Figure 38B:
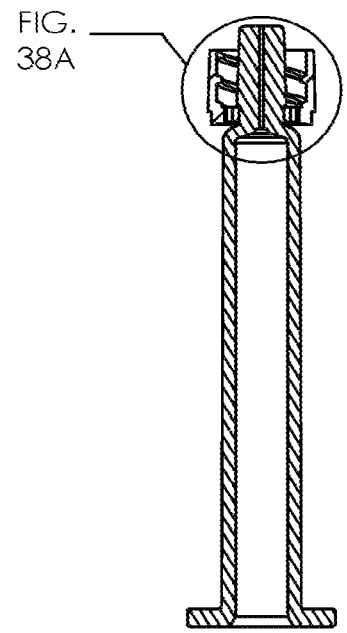

Referring to FIGS. 5, 38A, and 38B, a method is illustrated for forming a very small diameter dispensing portion 20 as disclosed above, sometimes referred to as having a reduced dead volume. U.S. Pat. No. 9,345,846 shows that a hypodermic syringe barrel can be made with a staked needle, as illustrated in present FIG. 5, by inserting the initially separate needle in the mold and forming the thermoplastic material around the needle. The present inventors have found that the dispensing portion 20 of a luer lock syringe barrel can be made similarly by inserting in the mold cavity a pin 790, which optionally can be either a hypodermic needle, thus hollow, or a solid pin. The pin 790 optionally can be a simple cylindrical pin, optionally can be provided without an anchoring portion, optionally can be provided without a sharpened end, and optionally can be treated with a mold release agent. The pin can have a diameter of from 0.05 mm to less than 1.8 mm, alternatively from 0.1 mm to 1.5 mm, alternatively from 0.3 mm to 1.8 mm, alternatively from 0.3 mm to 1.5 mm, alternatively from 0.4 mm to 0.8 mm, alternatively from 0.5 mm to 0.7 mm, alternatively 0.4 mm, 0.5 mm, or 0.6 mm. The thermoplastic material can be injection molded around the pin 790 to form the dispensing portion 20.

After the syringe barrel is formed, the pin 790 is drawn out of the front end 22 of the barrel, leaving a dispensing portion 20 of minimal diameter. In the reduced dead volume luer lock syringe, a specific needle gauge optionally can be used to achieve the desired dispensing portion or capillary inside diameter. In the case of the 0.5 ml luer lock syringe, a 27 gauge needle optionally can be used as the pin 790 to make a 0.4 mm capillary dispensing portion 20. The pin 790 optionally can be placed robotically into the mold and the syringe can be molded about the pin. The syringe optionally can be removed robotically from the mold with the pin 790 attached. In a separate station, outside the mold, the pin 790 can be mechanically removed from the syringe to open the dispensing portion 20. Optionally, the pin 790 does not have a needle point or a roughening pattern on the base, which conventionally can be used to affix the syringe permanently to the needle.

Figure 39A:
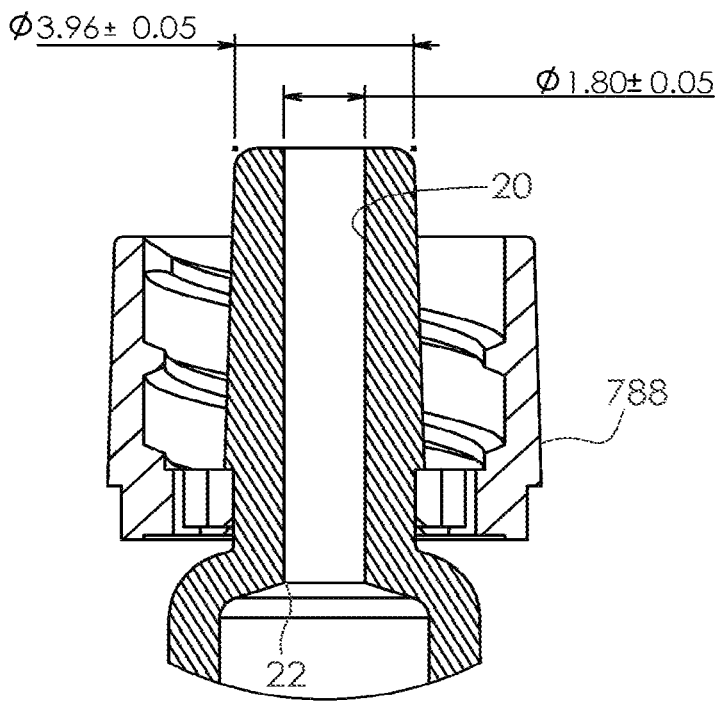
FIG. 39A shows, in an enlarged detail view of FIG. 39B, a luer lock syringe with a 1.8 mm inner diameter luer capillary with standard dead volume, which optionally can be used in any embodiment of the present invention.
Figure 39B:
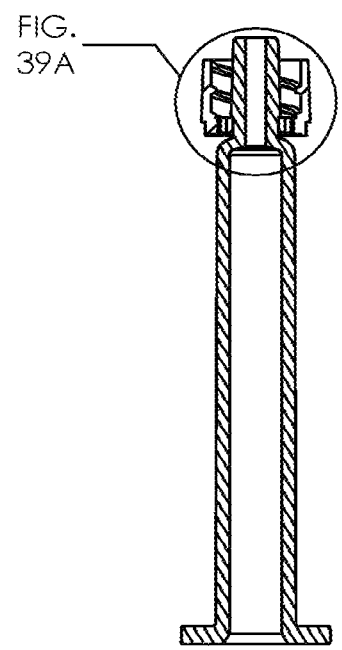

FIGS. 39A and 39 B illustrate, as another option, a luer lock syringe barrel with a more conventionally sized and molded dispensing portion 20, for example having an inner diameter of about 1.8 mm.

Using this approach, the luer dispensing portion 20 diameter can be made larger or smaller by selecting different sized needle gauges. With the conventional luer capillary, the inside diameter (ID) can be made with a traditional core pin that is an integral portion of the mold. The use according to this embodiment of a needle having a small gauge size, which is then removed, is advantageous to manufacture luer lock syringes with capillary IDs that are smaller than the ISO standard luer capillary size.

Optionally in any embodiment the coating set 285 can be provided on the interior surface 16 of the wall 15, the coating set 285 including the pH protective coating or layer 34.

Optionally in any embodiment, the coating set 285 can be provided on the exterior surface 216 of the wall 15.

Optionally in any embodiment, the coating set 285 excluding the pH protective coating or layer 34 can be provided.

Optionally in any embodiment, comprising an anti-scratch coating 33 over the coating set 285 can be provided.

Optionally in any embodiment, the coating set 285 on the interior surface 16 of the thermoplastic wall 15 and an anti-scratch coating 33 on the exterior surface 216 of the thermoplastic wall 15. can be provided.

Optionally in any embodiment, the anti-scratch coating 33 comprises a PECVD-applied coating having the following atomic ratios of Si, O, and C, measured by XPS:

Si=1,
O=0.7 to 1, and
C=1.1 to 1.5.

Optionally in any embodiment, the anti-scratch coating 33 comprises a film applied by wet chemistry to form a solid coating or layer. Such a film optionally may be 1 to 5 μm thick, as a non-limiting example. Composite anti-scratch coatings applied by wet chemistry, overlaid by a PECVD anti-scratch coating, are also contemplated.

A suitable example of a wet chemistry applied pH protective coating is coating the barrier coating or layer using a polyamidoamine epichlorohydrin resin. For example, the barrier coated part can be dip coated in a fluid polyamidoamine epichlorohydrin resin melt, solution or dispersion and cured by autoclaving or other heating at a temperature between 60 and 100° C. It is contemplated that a coating of polyamidoamine epichlorohydrin resin can be preferentially used in aqueous environments between pH 5-8, as such resins are known to provide high wet strength in paper in that pH range. Wet strength is the ability to maintain mechanical strength of paper subjected to complete water soaking for extended periods of time, so it is contemplated that a coating of polyamidoamine epichlorohydrin resinon an SiOx barrier layer will have similar resistance to dissolution in aqueous media. It is also contemplated that, because polyamidoamine epichlorohydrin resin imparts a lubricity improvement to paper, it will also provide lubricity in the form of a coating on a thermoplastic surface made of, for example, COC or COP.

Even another approach for protecting an SiOx layer is to apply as a pH protective coating or layer a liquid-applied coating of a polyfluoroalkyl ether, followed by atmospheric plasma curing the pH protective coating or layer. For example, it is contemplated that the process practiced under the trademark TriboGlide®, described in this specification, can be used to provide a pH protective coating or layer that is also a lubricity layer, as TriboGlide® is conventionally used to provide lubricity. A TriboGlide TriboLink™ Si crosslinked silicone coating can also be used as a pH protective coating or layer.

Optionally in any embodiment, the coating set 285 comprises an tie coating or layer 838 on the exterior surface 216 of the thermoplastic wall 15, a barrier coating or layer 30 on the tie coating or layer 838, and as the anti-scratch coating 33 a topcoat applied by wet chemistry on the barrier coating or layer 30.

Optionally in any embodiment, an insert-molded staked needle 156 and a needle shield 28 can be used.

Optionally in any embodiment, a pre-filled pharmaceutical package 210 can be used which is suitable for terminal sterilization by a sterilizing gas, optionally ethylene oxide EO gas, optionally at a pressure of 16.6 in. Hg (=42.2 cm. Hg, 56 kilopascal, 560 mbar) for 10 hours at 120° F. (49° C.), alternatively vaporized hydrogen peroxide (VHP).

Optionally in any embodiment, an ophthalmic drug can be provided in a pre-filled pharmaceutical package 210 of any one of the preceding claims for use in administering a liquid formulation 40 of an ophthalmic drug by intravitreal injection to a patient having an ocular disease, wherein the ocular disease optionally is selected from the group consisting of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Optionally in any embodiment, an ophthalmic drug in a pre-filled pharmaceutical package 210 can be provided for the use described above, wherein a volume of 30 to 100 μl of the liquid formulation 40 is administered to the patient.

Optionally in any embodiment, a pre-filled pharmaceutical package 210 can be provided that has been terminally sterilized.

Optionally in any embodiment, a pre-filled pharmaceutical package 210 can be provided which has been terminally sterilized with ethylene oxide.

Optionally in any embodiment, a kit 158 can be provided comprising one or more pre-filled pharmaceutical packages 210 as identified above, contained in a sealed outer package 170. The prefilled pharmaceutical package 210 is sterile and the thermoplastic wall 15 contains residual ethylene oxide. Optionally the sealed outer package 170 is permeable to ethylene oxide sterilant. Optionally, the lumen 18 is essentially free, preferably free, of ethylene oxide.

Optionally in any embodiment, The kit 158 of claim 49, further comprises a needle 156, optionally contained in the sealed outer package 170, optionally comprising a luer needle 156, alternatively a staked needle 156.

Optionally in any embodiment, the kit 158 of claim 50, further comprises a needle shield 28 installed on and enclosing at least a portion of the pharmaceutical package 210.

Optionally in any embodiment, the kit 158 can be provided, in which the needle shield 28 is sufficiently ethylene oxide permeable to permit ethylene oxide terminal sterilization of the entire pharmaceutical package 210 by ethylene oxide EO gas at a pressure of 16.6 in. (42.2 cm.) Hg for 10 hours at 120° F. (49° C.) when the needle shield 28 is installed over the needle 156, optionally when the pharmaceutical package 210 is enclosed in the sealed outer package 170.

Optionally in any embodiment, The kit 158 can be provided, further comprising a plunger rod 38, optionally contained in the sealed outer package 170.

Optionally in any embodiment, The kit 158 can be provided, further comprising instructions for use, optionally contained in the sealed outer package 170.

Still another aspect of the invention is a method for treating any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia, comprising administering an intravitreal injection of a liquid formulation 40 of an ophthalmic drug contained in the pre-filled pharmaceutical package 210 described above.

Even another aspect of the invention is use of a liquid formulation 40 of an ophthalmic drug in the manufacture of a pre-filled pharmaceutical package 210 described above for the treatment of any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Yet another aspect of the invention is a prefilled syringe as described above for use in a method of treating any one or more of age-related macular degeneration (AMD), visual impairment due to diabetic macular edema (DME), visual impairment due to macular edema secondary to retinal vein occlusion (branch RVO or central RVO), or visual impairment due to choroidal neovascularisation (CNV) secondary to pathologic myopia.

Protocols and Test Methods

Atomic Composition

The atomic compositions of the tie coating or layer, the barrier coating or layer 30, and the pH protective coating or layer 34 are characterized using X-Ray Photoelectron Spectroscopy (XPS), to measure silicon, oxygen, and carbon, and either Rutherford backscattering (RBS) or hydrogen forward scattering (HFS) spectrometry to measure hydrogen. A separate analytical method is used to determine the hydrogen content because XPS does not detect hydrogen. The following methods are used, unless otherwise expressly indicated.

XPS Protocol

XPS data is quantified using relative sensitivity factors and a model that assumes a homogeneous layer. The analysis volume is the product of the analysis area (spot size or aperture size) and the depth of information. Photoelectrons are generated within the X-ray penetration depth (typically many microns), but only the photoelectrons within the top three photoelectron escape depths are detected. Escape depths are on the order of 15-35 Å, which leads to an analysis depth of ~50-100 Å. Typically, 95% of the signal originates from within this depth.

The following analytical parameters are used:

| | |
|---|---|
| Instrument: | PHI Quantum 2000 |
| X-ray source: | Monochromated AlKa 1486.6 eV |
| Acceptance Angle | ±23° |
| Take-off angle | 45° |
| Analysis area | 600 μm |
| Charge Correction | C1s 284.8 eV |
| Ion Gun Conditions | Ar+, 1 keV, 2 × 2 mm raster |
| Sputter Rate | 15.6 Å/min (SiO2 Equivalent) |

Values given are normalized to 100 percent using the elements detected. Detection limits are approximately 0.05 to 1.0 atomic percent.

Rutherford Backscattering Spectrometry (RBS)

RBS spectra are acquired at a backscattering angle of 160° and an appropriate grazing angle (with the sample oriented perpendicular to the incident ion beam). The sample is rotated or tilted with a small angle to present a random geometry to the incident beam. This avoids channeling in both the film and the substrate. The use of two detector angles can significantly improve the measurement accuracy for composition when thin surface layers need to be analyzed.

When a thin (<100 nm) amorphous or polycrystalline film resides on a single crystal substrate, "ion channeling" may be utilized to reduce the backscattering signal from the substrate. This results in improved accuracy in the composition of layers containing elements that overlay with the substrate signal, typically light elements such as oxygen and carbon.

Analytical Parameters: RBS

| | |
|---|---|
| He++ Ion Beam Energy | 2.275 MeV |
| Normal Detector Angle | 160° |
| Grazing Detector Angle | ~100° |
| Analysis Mode | CC RR |

Spectra are fit by applying a theoretical layer model and iteratively adjusting elemental concentrations and thickness until good agreement is found between the theoretical and the experimental spectra.

Hydrogen Forward Scattering Spectrometry (HFS)

In an HFS experiment a detector is placed 30° from the forward trajectory of the incident He++ ion beam and the sample is rotated so that the incident beam strikes the surfaces 75° from normal. In this geometry it is possible to collect light atoms, namely hydrogen, forward-scattered from a sample after collisions with the probing He++ ion beam. A thin absorber foil is placed over the detector to filter out He++ ions that are also forward scattered from the sample.

Hydrogen concentrations are determined by comparing the number of hydrogen counts obtained from reference samples after normalizing by the stopping powers of the different materials. A hydrogen implanted silicon sample and a geological sample, muscovite, are used as references. The hydrogen concentration in the hydrogen implanted silicon sample is taken to be its stated implant dose of $1.6 \times 10^{17} \pm 0.2 \times 10^{17}$ atoms/cm$^2$. The muscovite (MUSC) sample is known to have ~6.5±0.5 atomic percent hydrogen.

Samples are checked for hydrogen loss in the analyzed region. This is done by acquiring spectra for different acquisition times (initially a short exposure followed by a longer exposure to the He++ beam). Charge accumulations for 5 and 40 µC are used. A lower proportional signal in the 40 µC spectrum indicates hydrogen loss. In those cases the shorter exposure is chosen for analysis at the expense of higher noise in the spectrum. To account for surface hydrogen due to residual moisture or hydrocarbon adsorption a silicon control sample is analyzed together with the actual samples and the hydrogen signal from the control sample is subtracted from each of the spectra obtained from the actual samples. During the HFS acquisition backscattering spectra are acquired using the 160° angle detector (with the sample in forward scattering orientation). The RBS spectra are used to normalize the total charge delivered to the sample.

Analytical Parameters: HFS

| | |
|---|---|
| He++ Ion Beam Energy | 2.275 MeV |
| Normal Detector Angle | 160° |
| Grazing Detector Angle | ~30° |
| Ion Beam to Sample Normal | 75° |

Protocol for Total Silicon Measurement

This protocol is used to determine the total amount of silicon coatings present on the entire vessel wall. A supply of 0.1 N potassium hydroxide (KOH) aqueous solution is prepared, taking care to avoid contact between the solution or ingredients and glass. The water used is purified water, 18 MΩ quality. A Perkin Elmer Optima Model 7300DV ICP-OES instrument is used for the measurement except as otherwise indicated.

Each device (vial, syringe, tube, or the like) to be tested and its cap and crimp (in the case of a vial) or other closure are weighed empty to 0.001 g, then filled completely with the KOH solution (with no headspace), capped, crimped, and reweighed to 0.001 g. In a digestion step, each vial is placed in an autoclave oven (liquid cycle) at 121° C. for 1 hour. The digestion step is carried out to quantitatively remove the silicon coatings from the vessel wall into the KOH solution. After this digestion step, the vials are removed from the autoclave oven and allowed to cool to room temperature. The contents of the vials are transferred into ICP tubes. The total Si concentration is run on each solution by ICP/OES following the operating procedure for the ICP/OES.

The total Si concentration is reported as parts per billion of Si in the KOH solution. This concentration represents the total amount of silicon coatings that were on the vessel wall before the digestion step was used to remove it.

The total Si concentration can also be determined for fewer than all the silicon layers on the vessel, as when an $SiO_x$ barrier coating or layer 30 is applied, an $SiO_xC_y$ second layer (for example, a lubricity layer or a pH protective coating or layer 34) is then applied, and it is desired to know the total silicon concentration of just the $SiO_xC_y$ layer. This determination is made by preparing two sets of vessels, one set to which only the $SiO_x$ layer is applied and the other set to which the same $SiO_x$ layer is applied, followed by the $SiO_xC_y$ layer or other layers of interest. The total Si concentration for each set of vessels is determined in the same manner as described above. The difference between the two Si concentrations is the total Si concentration of the $SiO_xC_y$ second layer.

Protocol for Measuring Dissolved Silicon in a Vessel

In some of the working examples, the amount of silicon dissolved from the wall of the vessel by a test solution is determined, in parts per billion (ppb), for example to evaluate the dissolution rate of the test solution. This determination of dissolved silicon is made by storing the test solution in a vessel provided with an $SiO_x$ and/or $SiO_xC_y$ coating or layer under test conditions, then removing a sample of the solution from the vessel and testing the Si concentration of the sample. The test is done in the same manner as the Protocol for Total Silicon Measurement, except that the digestion step of that protocol is replaced by storage of the test solution in the vessel as described in this protocol. The total Si concentration is reported as parts per billion of Si in the test solution Protocol for Determining Average Dissolution Rate As shown in the working examples, the silicon dissolution rate is measured by determining the total silicon leached from the vessel into its contents, and does not distinguish between the silicon derived from the pH protective coating or layer 34, the lubricity layer 281, the barrier coating or layer 30, or other materials present.

The average dissolution rates reported in the working examples are determined as follows. A series of test vessels having a known total silicon measurement are filled with the desired test solution analogous to the manner of filling the vials with the KOH solution in the Protocol for Total Silicon Measurement. (The test solution can be a physiologically inactive test solution as employed in the present working examples or a physiologically active formulation 40 intended to be stored in the vessels to form a pharmaceutical package 210). The test solution is stored in respective vessels for several different amounts of time, and then analyzed for the Si concentration in parts per billion in the test solution for each storage time. The respective storage times and Si concentrations are then plotted. The plots are studied to find a series of substantially linear points having the steepest slope.

The plot of dissolution amount (ppb Si) versus days decreases in slope with time, even though it does not appear that the Si layer has been fully digested by the test solution.

For the PC194 test data in Table 10 below, linear plots of dissolution versus time data are prepared by using a least squares linear regression program to find a linear plot corresponding to the first five data points of each of the experimental plots. The slope of each linear plot is then determined and reported as representing the average dissolution rate applicable to the test, measured in parts per billion of Si dissolved in the test solution per unit of time.

Measurement of Coating Thickness

The thickness of a PECVD coating or layer such as the pH protective coating or layer 34, the barrier coating or layer 30, the lubricity coating or layer, and/or a composite of any two or more of these layers can be measured, for example, by transmission electron microscopy (TEM).

The TEM can be carried out, for example, as follows. Samples can be prepared for Focused Ion Beam (FIB) cross-sectioning in two ways. Either the samples can be first coated with a thin layer of carbon (50-100 nm thick) and then coated with a sputtered coating or layer of platinum (50-100 nm thick) using a K575X Emitech tie coating or layer system, or the samples can be coated directly with the protective sputtered Pt layer. The coated samples can be placed in an FEI FIB200 FIB system. An additional coating or layer of platinum can be FIB-deposited by injection of an organometallic gas while rastering the 30 kV gallium ion beam over the area of interest. The area of interest for each sample can be chosen to be a location half way down the length of the syringe barrel. Thin cross sections measuring approximately 15 μm ("micrometers") long, 2 μm wide and 15 μm deep can be extracted from the die surface using an in-situ FIB lift-out technique. The cross sections can be attached to a 200 mesh copper TEM grid using FIB-deposited platinum. One or two windows in each section, measuring about 8 μm wide, can be thinned to electron transparency using the gallium ion beam of the FEI FIB.

Cross-sectional image analysis of the prepared samples can be performed utilizing either a Transmission Electron Microscope (TEM), or a Scanning Transmission Electron Microscope (STEM), or both. All imaging data can be recorded digitally. For STEM imaging, the grid with the thinned foils can be transferred to a Hitachi HD2300 dedicated STEM. Scanning transmitted electron images can be acquired at appropriate magnifications in atomic number contrast mode (ZC) and transmitted electron mode (TE). The following instrument settings can be used.

| Instrument | Scanning Transmission Electron Microscope |
|---|---|
| Manufacturer/Model | Hitachi HD2300 |
| Accelerating Voltage | 200 kV |
| Objective Aperture | 2 |
| Condenser Lens 1 Setting | 1.672 |
| Condenser Lens 2 Setting | 1.747 |
| Approximate Objective Lens Setting | 5.86 |
| ZC Mode Projector Lens | 1.149 |
| TE Mode Projector Lens | 0.7 |
| Image Acquisition | |
| Pixel Resolution | 1280 × 960 |
| Acquisition Time | 20 sec. (×4) |

For TEM analysis the sample grids can be transferred to a Hitachi HF2000 transmission electron microscope. Transmitted electron images can be acquired at appropriate magnifications. The relevant instrument settings used during image acquisition can be those given below.

| Instrument | Transmission Electron Microscope |
|---|---|
| Manufacturer/Model | Hitachi HF2000 |
| Accelerating Voltage | 200 kV |
| Condenser Lens 1 | 0.78 |
| Condenser Lens 2 | 0 |
| Objective Lens | 6.34 |
| Condenser Lens Aperture | 1 |
| Objective Lens Aperture for imaging | 3 |
| Selective Area Aperture for SAD | N/A |

SEM Procedure

SEM Sample Preparation: Each syringe sample is cut in half along its length (to expose the inner or interior surface). The top of the syringe (luer end) can be cut off to make the sample smaller.

The sample is mounted onto the sample holder with conductive graphite adhesive, then put into a Denton Desk IV SEM Sample Preparation System, and a thin (approximately 50 Å) gold coating is sputtered onto the inner or interior surface of the syringe. The gold coating is used to eliminate charging of the surface during measurement.

The sample is removed from the sputter system and mounted onto the sample stage of a Jeol JSM 6390 SEM (Scanning Electron Microscope). The sample is pumped down to at least $1 \times 10^{-6}$ Torr in the sample compartment. Once the sample reaches the required vacuum level, the slit valve is opened and the sample is moved into the analysis station.

The sample is imaged at a coarse resolution first, and then higher magnification images are accumulated. The SEM images can be, for example, 5 μm edge-to-edge (horizontal and vertical).

AFM (Atomic Force Microscopy) Procedure.

AFM images are collected using a NanoScope III Dimension 3000 machine (Digital Instruments, Santa Barbara, Calif., USA). The instrument is calibrated against a NIST traceable standard. Etched silicon scanning probe microscopy (SPM) tips are used. Image processing procedures involving auto-flattening, plane fitting or convolution are employed. One 10 μm×10 μm area is imaged. Roughness analyses are performed and are expressed in: (1) Root-Mean-Square Roughness, RMS; 2 Mean Roughness, $R_a$; and (3) Maximum Height (Peak-to-Valley), $R_{max}$, all measured in nanometers (nm). For the roughness analyses, each sample is imaged over the 10 μm×10 μm area, followed by three cross sections selected by the analyst to cut through features in the 10 μm×10 μm images. The vertical depth of the features is measured using the cross section tool. For each cross section, a Root-Mean-Square Roughness (RMS) in nanometers is reported.

The Digital Instruments Nanoscope III AFM/STM acquires and stores 3-dimensional representations of surfaces in a digital format. These surfaces can be analyzed in a variety of ways.

The Nanoscope III software can perform a roughness analysis of any AFM or STM image. The product of this analysis is a single page reproducing the selected image in top view. The image can include an "Image Statistics" box, which lists the calculated characteristics of the whole image minus any areas excluded by a stopband (a box with an X through it). Similar additional statistics can be calculated for a selected portion of the image and these can be listed in the "Box Statistics" in the lower right portion of the page. What follows is a description and explanation of these statistics.

Image Statistics:

Z Range ($R_p$): The difference between the highest and lowest points in the image. The value is not corrected for tilt in the plane of the image; therefore, plane fitting or flattening the data will change the value.

Mean: The average of all of the Z values in the imaged area. This value is not corrected for the tilt in the plane of the image; therefore, plane fitting or flattening the data will change this value.

RMS($R_q$): This is the standard deviation of the Z values (or RMS roughness) in the image. It is calculated according to the formula:

$$Rq=\{\Sigma(Z_1-Z_{avg})2/N\}$$

where $Z_{avg}$ is the average Z value within the image; $Z_1$ is the current value of Z; and N is the number of points in the image. This value is not corrected for tilt in the plane of the image; therefore, plane fitting or flattening the data will change this value.

Mean roughness ($R_a$): This is the mean value of the surface relative to the Center Plane and is calculated using the formula:

$$R_a=[1/(L_xL_y)]\int_oL_y\int_oL_x\{f(x,y)\}dxdy$$

where f(x,y) is the surface relative to the Center plane, and $L_x$ and $L_y$ are the dimensions of the surface.

Max height ($R_{max}$): This is the difference in height between the highest and lowest points of the surface relative to the Mean Plane.

Surface area: (Optical calculation): This is the area of the 3-dimensional surface of the imaged area. It is calculated by taking the sum of the areas of the triangles formed by 3 adjacent data points throughout the image.

Surface area diff: (Optional calculation) This is the amount that the Surface area is in excess of the imaged area. It is expressed as a percentage and is calculated according to the formula:

$$\text{Surface area diff}=100[(\text{Surface area}/S_1^{-1}]$$

where $S_1$ is the length (and width) of the scanned area minus any areas excluded by stopbands.

Center Plane: A flat plane that is parallel to the Mean Plane. The volumes enclosed by the image surface above and below the center plane are equal.

Mean Plane: The image data has a minimum variance about this flat plane. It results from a first order least squares fit on the Z data.

Spectral Reflectance Protocol for Thickness Mapping

A Filmetrics Thin-Film Analyzer Model 205-0436 F40 spectral reflectance instrument was used. The syringe is placed in a holder with the back end facing up and index marks on the back end dividing the circumference into 8 equal 45-degree segments. The instrument camera is focused on the coating or layer and a thickness measurement is acquired at 0 degrees on the circumference and 6 mm from the back end of the mapped area of the syringe barrel, vial, sample collection tube, or other vessel. Then the syringe is shifted 45 degrees, remaining at 6 mm axially, and another measurement is acquired. The process is repeated at 45 degree intervals around the syringe at 6 mm. The syringe is then advanced axially to 11 mm from the back end of the mapped area, and eight measurements are taken around the circumference. The syringe is successively advanced by 5 mm increments axially and 45 degree increments circumferentially to complete the map. The data is mapped using Filmetrics software. The mapped data can be analyzed statistically to determine the mean thickness and standard deviation values for the coated vessel.

Protocol for Lubricity Testing

The following materials are used in this test: [0146] Commercial (BD Hypak® PRTC) glass prefillable syringes with luer-Lok® tip) (ca 1 mL) [0147] COC syringe barrels made according to the Protocol for Forming COC Syringe barrel; [0148] Commercial plastic syringe plungers with elastomeric tips taken from Becton Dickinson Product No. 306507 (obtained as saline prefilled syringes); [0149] Normal saline solution (taken from the Becton-Dickinson Product No. 306507 prefilled syringes); [0150] Dillon Test Stand with an Advanced Force Gauge (Model AFG-50N) [0151] Syringe holder and drain jig (fabricated to fit the Dillon Test Stand)

The following procedure is used in this test.

The jig is installed on the Dillon Test Stand. The platform probe movement is adjusted to 6 in/min (2.5 mm/sec) and upper and lower stop locations were set. The stop locations were verified using an empty syringe and barrel. The commercial saline-filled syringes were labeled, the plungers were removed, and the saline solution is drained via the open ends of the syringe barrels for re-use. Extra plungers were obtained in the same manner for use with the COC and glass barrels.

Syringe plungers were inserted into the COC syringe barrels so that the second horizontal molding point of each plunger is even with the syringe barrel lip (about 10 mm from the tip end). Using another syringe and needle assembly, the test syringes were filled via the capillary end with 2-3 milliliters of saline solution, with the capillary end uppermost. The sides of the syringe were tapped to remove any large air bubbles at the plunger/fluid interface and along the walls, and any air bubbles were carefully pushed out of the syringe while maintaining the plunger in its vertical orientation.

The samples were created by coating COC syringe barrels according to the Protocol for Coating COC Syringe Barrel Interior with OMCTS Lubricity layer. An alternative embodiment of the technology herein, would apply the lubricity layer or coating over another thin film coating, such as $SiO_x$, for example applied according to the Protocol for Coating COC Syringe barrel Interior with $SiO_x$.

Instead of the Dillon Test Stand and drain jig, a Genesis Packaging Plunger Force Tester (Model SFT-01 Syringe Force Tester, manufactured by Genesis Machinery, Lionville, Pa.) can also be used following the manufacturer's instructions for measuring Fi and Fm. The parameters that are used on the Genesis tester are: Start: 10 mm; Speed: 100 mm/min; Range: 20; Units: Newtons.

Examples A-C—Glass Vs. Coated COP Pharmaceutical Packages

Three types of pharmaceutical packages in the form of pre-filled syringes with closures, identified in Table 1, were made and filled with 167 μL of a Ranibizumab formulation.

TABLE 1

| Type | Syringe size | Syringe barrel | Coating | Stopper |
|---|---|---|---|---|
| A | 1.0 ml | Cyclo-olefin polymer (COP) | Trilayer | FluroTec ®* |
| B | 1.0 ml | Borosilicate glass | Baked on silicone | FluroTec ® |

TABLE 1-continued

| Type | Syringe size | Syringe barrel | Coating | Stopper |
|---|---|---|---|---|
| C | 1.0 ml | Cyclo-olefin polymer (COP) | Trilayer + Lubricity | FluroTec ® |

*Trademark of West Pharmaceutical Services, Inc. for commercial syringe plungers with FluroTec ® film laminate surfaces, adapted for use in pre-filled syringes.

The A and C type pharmaceutical packages used in testing (COP syringes with staked needles) were made as follows. Syringe barrels suitable for intravitreal injection, having a nominal maximum fill volume of 1 mL, illustrated by FIGS. 3-5, were injection molded from COP resin. The staked hypodermic needles were molded-in inserts, secured in place without using any glue. Needle shields 28 were installed on the syringe barrels and kept in place throughout the manufacturing process. The shields functioned both to protect the needle and, by burying the needle in the material of the shield, to seal off the needle. Sterilizing gas, in particular ethylene oxide, is able to penetrate the needle shield during sterilization to effectively sterilize the exterior of the needle and the air captured within the shield.

PECVD coaters, illustrated by FIGS. 6-8 and the accompanying text above, were used to apply adhesive, barrier, and pH protective coatings or layers to the inside of each Type A and Type C syringe barrel. The coating conditions in Tables 2-4 were used for the type A barrels, and the coating conditions in Tables 2-6 were used for the type B barrels.

TABLE 2

Adhesive Coating or Layer

| Variable | Units | Value |
|---|---|---|
| Net Power | WATTS | 20 |
| Ar | SCCM | 20 |
| TMDSO | SCCM | 2 |
| $O_2$ | SCCM | 1 |
| Plasma Duration | Time (sec.) | 2.5 |
| Plasma Start Delay | Time (sec.) | 15 |
| Vaporizer Temp. | CELSIUS | 90/80 |
| Reflected Power | WATTS | 0 |
| Chuck Pressure | TORR | 0.8 |
| Inlet Pressure | TORR | 17 |

TABLE 3

Barrier Coating or Layer

| Variable | Units | Value |
|---|---|---|
| Net Power | WATTS | 40 |
| HMDSO | SCCM | 0.75 |
| $O_2$ | SCCM | 75 |
| Plasma Duration | Time (sec.) | 10 |
| Plasma Start Delay | Time (sec.) | 10 |
| Vaporizer Temp. Controller | CELSIUS | 110/80 |
| Reflected Power | WATTS | 0 |
| Chuck Pressure | TORR | 1.5 |
| Inlet Pressure | TORR | 37.0 |

TABLE 4 pH Protective Coating or Layer

| Variable | Units | Value |
|---|---|---|
| Net Power | WATTS | 20 |
| Ar | SCCM | 20 |
| TMDSO | SCCM | 2 |
| $O_2$ | SCCM | 1 |
| Plasma Duration | Time (sec.) | 10 |
| Plasma Start Delay | Time (sec.) | 15 |
| Vaporizer Temp. Controller | CELSIUS | 90/80 |
| Chuck Pressure | TORR | 0.8 |
| Inlet Pressure | TORR | 17.0 |

TABLE 5

Lubricity Coating or Layer-Step 1

| Variable | Units | Value |
|---|---|---|
| Net Power | WATTS | 50 |
| Ar | SCCM | 7.5 |
| OMCTS | SCCM | 4 |
| $O_2$ | SCCM | 3.1 |
| Plasma Duration | Time (sec.) | 1 |
| Plasma Start Delay | Time (sec.) | 15 |
| Vaporizer Temp. Controller | CELSIUS | 120/100 |
| Main Vacuum Pressure | TORR | N/A |
| Chuck Pressure | TORR | N/A |
| Inlet Pressure | TORR | N/A |

TABLE 6

Lubricity Coating or Layer-Step 2

| Variable | Units | Value |
|---|---|---|
| Net Power | WATTS | 2 |
| Ar | SCCM | 7.5 |
| OMCTS | SCCM | 4 |
| $O_2$ | SCCM | 3.1 |
| Plasma Duration | Time (sec.) | 15 |
| Plasma Start Delay | Time (sec.) | 3 |
| Vaporizer Temp. Controller | CELSIUS | 120/100 |
| Main Vacuum Pressure | TORR | 0.045 |
| Chuck Pressure | TORR | 0.168 |
| Inlet Pressure | TORR | 3.45 |

Figure 11:
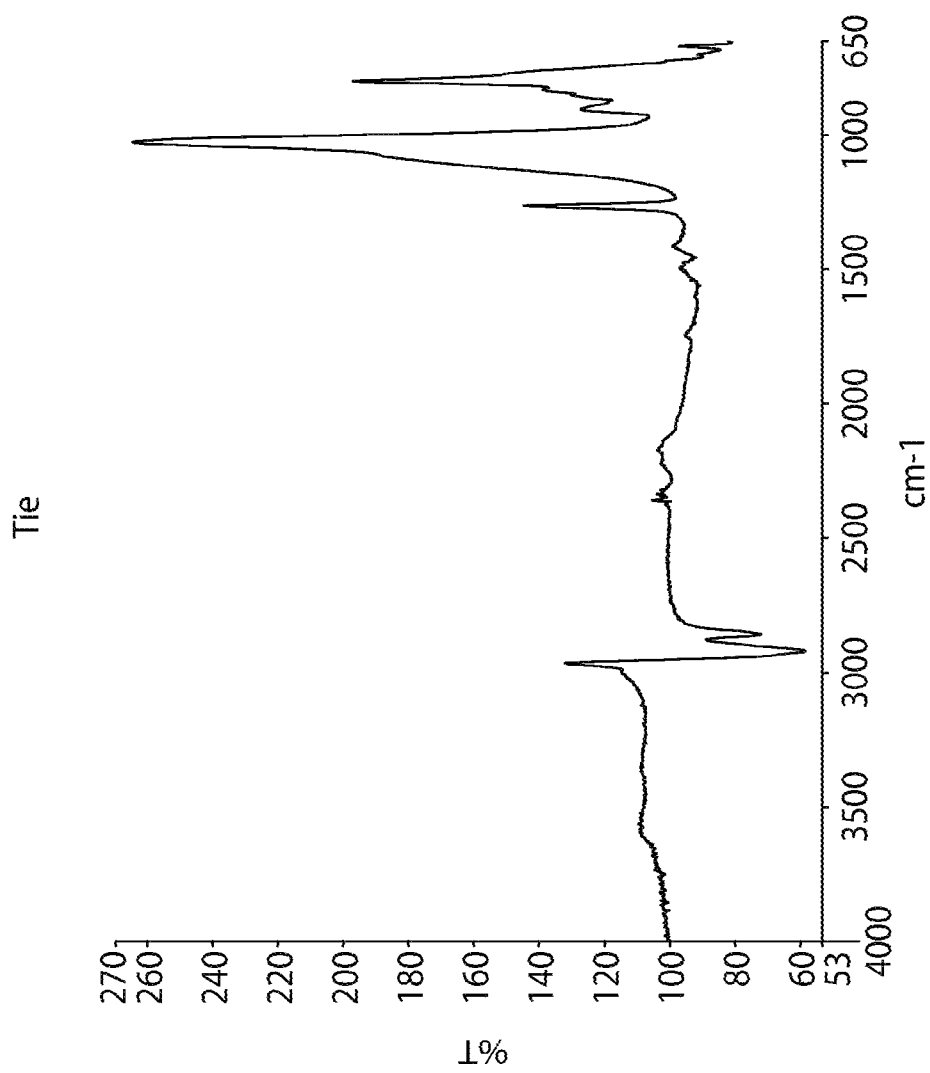
FIG. 11 is a Fourier-transform infrared spectrum representative of the tie coating or layer applied in Examples A and C, characterizing the coating chemistry.
Figure 12:
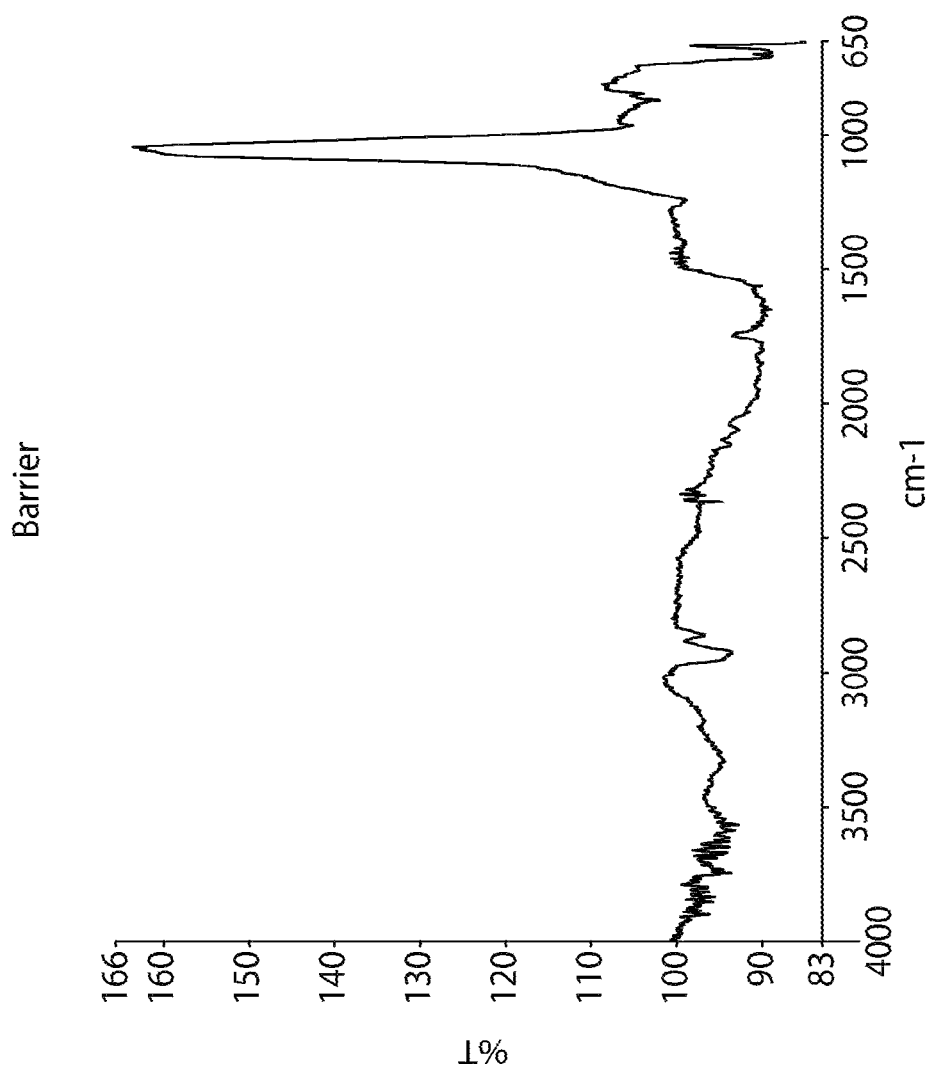
FIG. 12 is a Fourier-transform infrared spectrum representative of the barrier coating or layer applied in Examples A and C, characterizing the coating chemistry.
Figure 13:
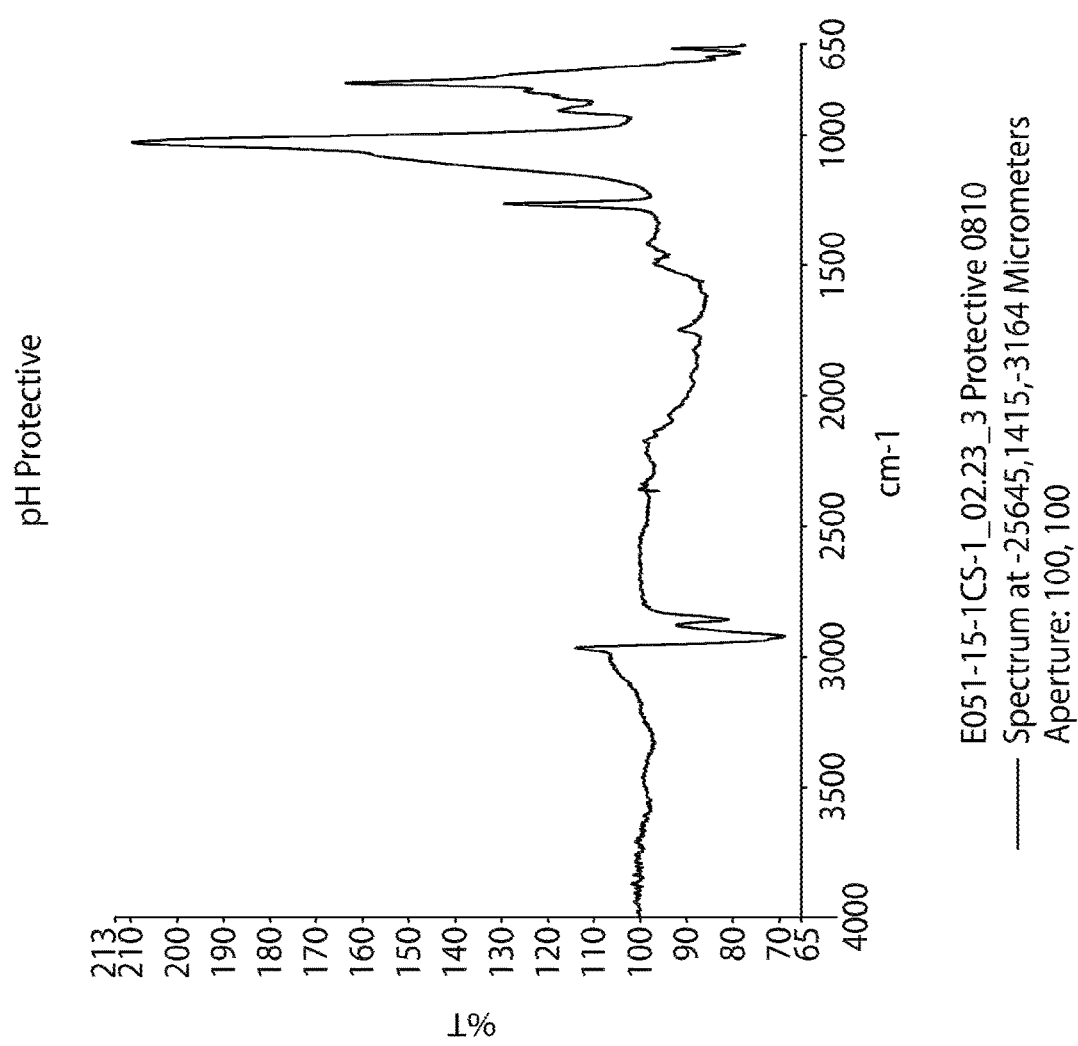
FIG. 13 is a Fourier-transform infrared spectrum representative of the pH protective coating or layer applied in Examples A and C, characterizing the coating chemistry.

The respective adhesive, barrier, and pH protective coatings or layers of representative syringes had the following properties. The adhesive coating or layer and the pH protective coating or layer of a representative syringe each had the empirical composition $SiO_{1.3}C_{0.8}H_{3.6}$, measured by XPS and Rutherford Backscattering. The barrier coating or layer of the representative syringe had the empirical composition $SiO_{2.0}$, measured by XPS. FIGS. 11-13 show representative FTIR plots of the respective adhesive coating or layer (FIG. 11), the barrier coating or layer (FIG. 12), and the pH protective coating or layer (FIG. 13).

Figure 14:
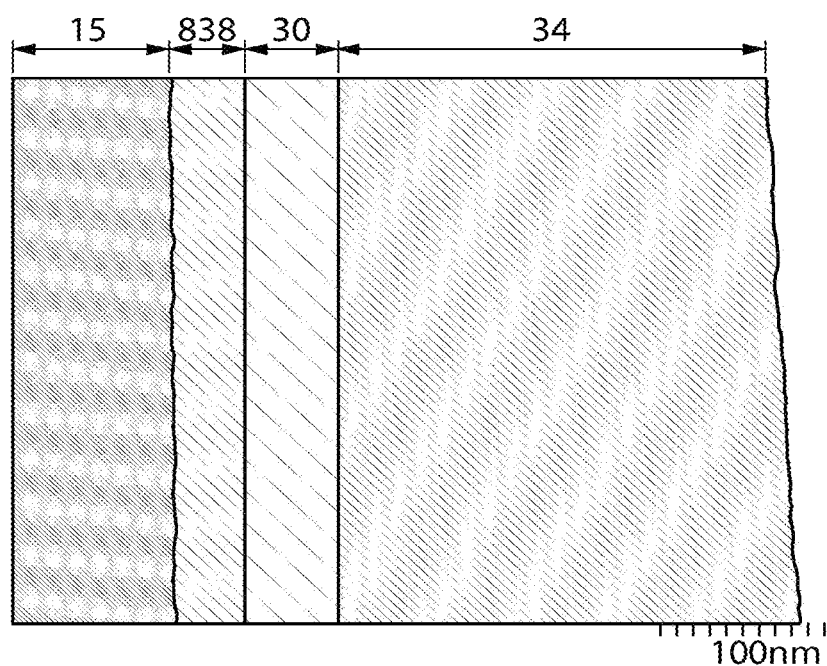
FIG. 14 is a TEM image of a cross-section of the coating applied in Example A, showing the relative thickness of, and sharp transitions between, the tie coating or layer, the barrier coating or layer, and the pH protective coating or layer.
Figure 15:
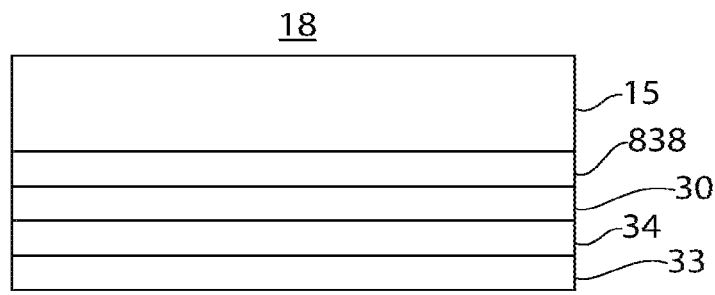
FIG. 15 is an alternative enlarged detail view of the indicated portion of FIG. 1, showing an exterior coating set (Coating Stack 1) comprising an adhesion coating or layer, a barrier coating or layer, a protective coating or layer, and an antiscratch coating or layer.
Figure 16:
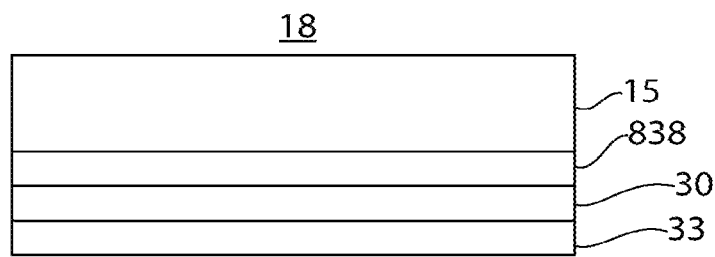
FIG. 16 is an alternative enlarged detail view of the indicated portion of FIG. 1, showing an exterior coating set (Coating Stack 2) comprising an adhesion coating or layer, a barrier coating or layer, a protective coating or layer, and an antiscratch coating or layer.
Figure 17:
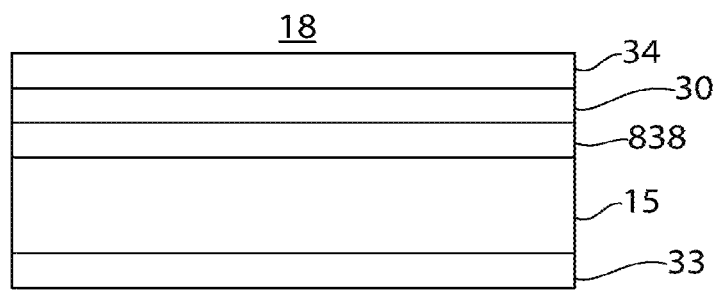
FIG. 17 is an alternative enlarged detail view of the indicated portion of FIG. 1, showing an exterior coating set comprising an antiscratch coating or layer and an interior coating set comprising an adhesion coating or layer, a barrier coating or layer, and a protective coating or layer.
Figure 18:
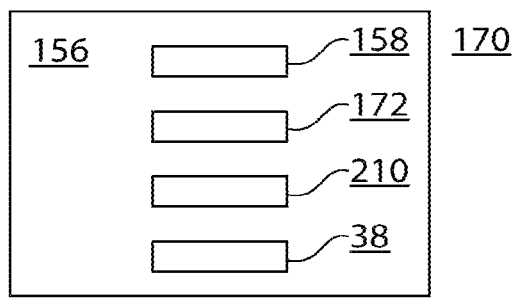
FIG. 18 is a schematic view of a kit.

A TEM measurement was made at one point half way down the length of a representative coated Type A syringe barrel, producing the image shown in FIG. 14. This measurement showed the adhesion coating or layer was 38 nm thick, the barrier coating or layer was 55 nm thick, and the pH protective coating or layer was 273 nm thick at that point. The coating thickness varied depending on the point of measurement, as is typical. The overall coating set of the syringe barrel was measured using Filmetrics Thin-Film Analyzer Model 205-0436 F40 spectral reflectance analysis, and found to be 572±89 nm thick, which is very consistent for a 1 mL syringe barrel.

For the Type C syringe barrels, the first three layers were formed and had the properties described for the Type A syringe barrel, then an additional PECVD lubricity coating or layer was applied in the same equipment, using the specific coating conditions of Table 6. The resulting PECVD lubricity coating has a thickness profile from less than 10 nm near the front (also known as the dispensing end) of the syringe barrel, where lubricity is not required, to about 12 nm about half way down the axial length of the barrel where lubricity is required only to reduce the plunger sliding force, to about 80 nm near the back of the syringe where lubricity is required to reduce both the breakout force and the plunger sliding force The Type B syringe barrels were commercial borosilicate glass syringe barrels, having a nominal maximum fill volume of 1 mL similar or identical to a pre-filled Ranibizumab syringe approved by the European Medicines Agency (EMA). The syringe barrel consists of borosilicate glass which was spray-coated with silicon oil-in-water emulsion and subsequently heat-fixed (so-called "baked silicone") (poster presentation by Clunas et al. at the 5th World Congress on Controversies in Ophthalmology, Mar. 20-23, 2014; poster presentation of Michaud et al. at the ARVO Annual Meeting 2014).

The three types of syringe barrels were filled as follows. 165 µl of a solution of the anti-VEGF antibody Ranibizumab containing 10 mg/ml of the antibody and histidine buffer, trehalose dihydrate, polysorbate 20, pH 5.5 was filled into the syringes as listed above in Table 1, then incubated at different temperatures for different periods.

The samples can be tested by RP-HPLC for the presence of hydrophilic and hydrophobic species, by cation exchange chromatography for the presence of acidic and basic variants of the antibody and by size exclusion chromatography for the presence of aggregates, each measured at various storage times from two weeks up to three months.

It is anticipated that Syringe Types A and C of the present invention will perform equal to or better than Syringe Type B in these tests.

It is further anticipated that the Syringe Types A and C of the present invention, as made and after storage, will have a breakout force of less than or equal to 10N for initiating travel of the plunger in the lumen, and a plunger sliding force of less than or equal to 10N for advancing the plunger in the lumen.

It is further anticipated that the Syringe Types A and C of the present invention, as made and after storage, will meet the particle count standard for particulate matter in ophthalmic solutions of USP789 as in force on Nov. 1, 2015, or Ph. Eur 5.7.1 as in force on Nov. 1, 2015, or both, at the time of filling the pre-filled syringe, alternatively after three months of storage of the pre-filled syringe at 4-8° C., alternatively after three months of storage of the pre-filled syringe at 25° C. and 60% relative humidity, alternatively after three months of storage of the pre-filled syringe at 40° C. and 75% relative humidity.

Examples D-E—Lubricity Testing

Following the Protocol for Lubricity Testing, except as modified here, three lots of 1 mL staked needle syringes were made from thermoplastic cyclic olefin polymer (COP) resin, provided with an interior trilayer coating and lubricity coating substantially as described above in Example C (i.e. type C), filled with a test solution or control, fitted with closures—Novapure® plungers having FluroTec® barrier film on their leading surfaces (trademarks of West Pharmaceutical Services, Inc., Weston, Pa. US)—and tested immediately (T=0 days) or after storage for 3 days, 7 days, or 4 weeks at a specified temperature of 4° C., 25° C., or 40° C. The syringes were tested for break loose force ("Break Force") and sliding force ("Glide Force") performance.

For Example D, 1.0 mL of the test solution (Solution A) was used, consisting of 100 mg/mL of α, α-trehalose dihydrate, 1.98 mg/mL L-histidine; and 0.1 mg/mL Polysorbate 20 in water for injection. This is the inactive portion of the previously-defined Ranibizumab 6 mg/ml and 10 mg/ml formulations. For Example E, 1.0 mL of the control (Solution B) was used, consisting of Milli-q® particle-free water (trademark of Merck KGAA, Darmstadt, Del.). The syringes were subjected to e-beam sterilization before storage.

The test protocol was carried out using a plunger advance rate of 300 mm/min.

Figure 36:
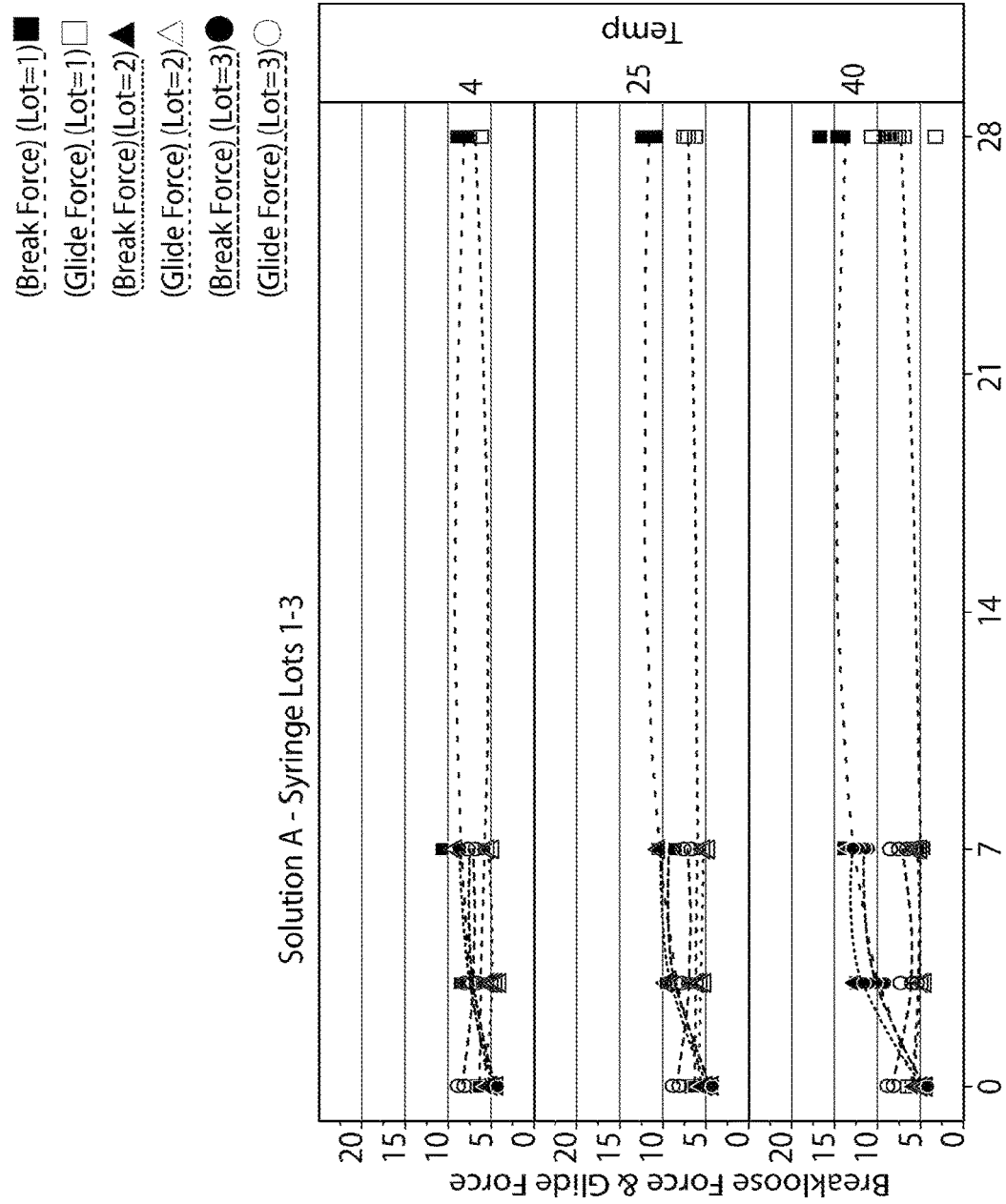
FIG. 36 shows three plots of break force and glide force vs. storage time before testing, for Example D.
Figure 37:
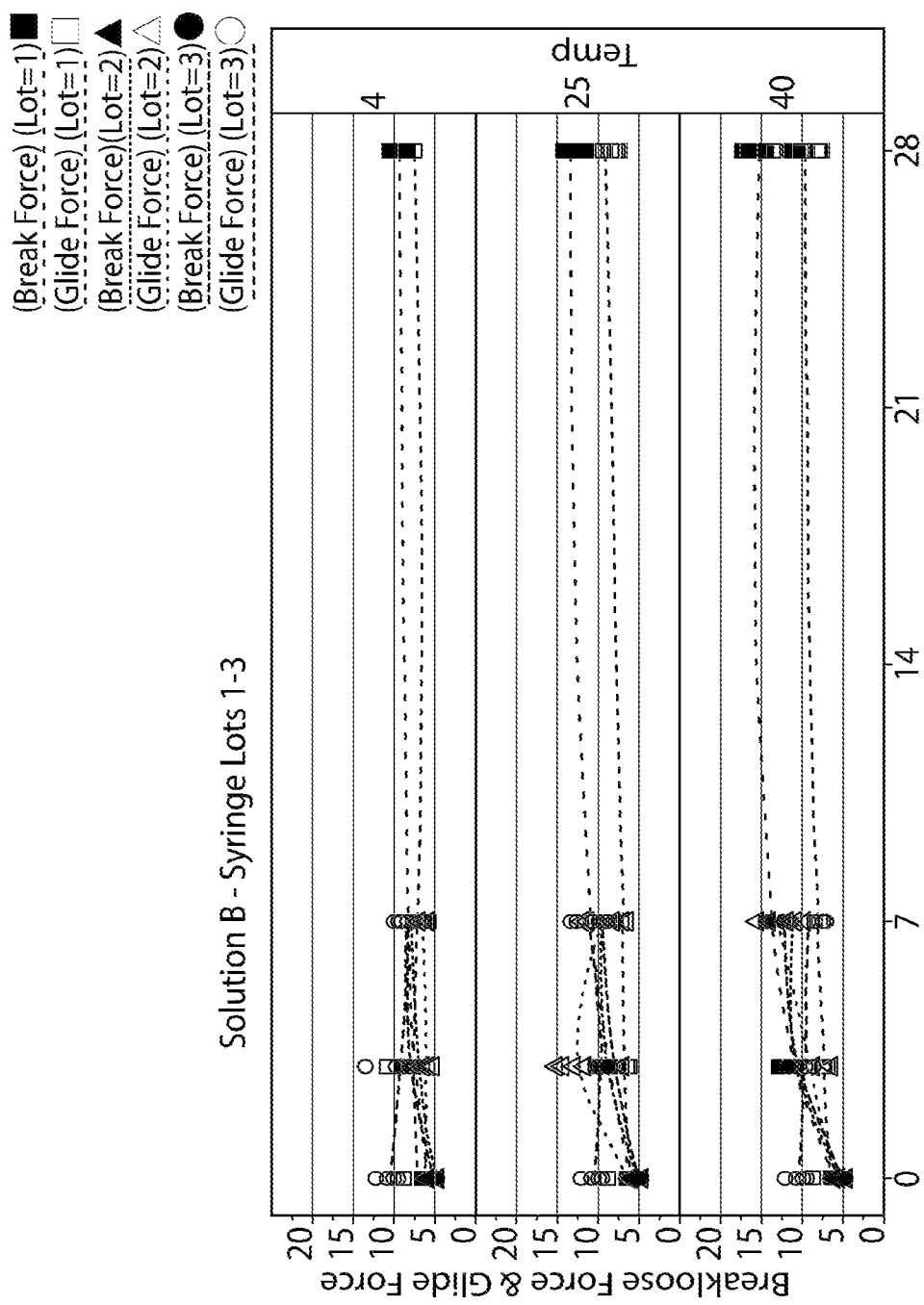
FIG. 37 shows three plots of break force and glide force vs. storage time before testing, for Example E.

The results are shown in FIGS. 36 and 37. For the test solution as shown in FIG. 36, at T=0 and after 3, 7, or 28 days of storage, the "glide force" remained fairly constant at all test periods, and ranged from about 5N (Newtons) to no more than 10N after storage at 4° C., 25° C., or 40° C. The "break force" also remained fairly constant at all test periods, and ranged from 5N to less than 15N at all data points. This data shows that the inactive ingredients constituting the great bulk of the Ranibizumab 6 mg/ml and 10 mg/ml formulations did not increase the break force or glide force required to operate the syringe, showing the likely suitability of this pharmaceutical package for containment and delivery of Ranibizumab 6 mg/ml and 10 mg/ml formulations at commercially desirable plunger forces.

What is claimed is:

1. An ophthalmic drug in a pre-filled pharmaceutical package comprising:
   a syringe barrel having a front dispensing opening and a back opening, the syringe barrel comprising a thermoplastic wall having an interior surface enclosing at least a portion of a lumen, an exterior surface, and a coating set on at least one of the interior surface and the exterior surface of the wall, the coating set comprising:
      a tie coating or layer on the interior surface or the exterior surface comprising $SiO_xC_yH_z$ in which x is from about 0.5 to about 2.4 as measured by X-ray photoelectron spectroscopy (XPS), y is from about 0.6 to about 3 as measured by XPS, and z is from about 2 to about 9 as measured by at least one of Rutherford backscattering spectrometry (RBS) or hydrogen forward scattering (HFS), the tie coating or layer having a facing surface facing toward the wall, the tie coating or layer also having an opposed surface facing away from the wall;
      a barrier coating or layer of $SiO_x$, in which x is from about 1.5 to about 2.9 as measured by XPS, the barrier coating or layer having a facing surface facing toward the opposed surface of the tie coating or layer and an opposed surface facing away from the tie coating or layer;
      a pH protective coating or layer of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS, the pH protective coating or layer having a facing surface facing toward the opposed surface of the barrier layer and an opposed surface facing away from the barrier layer;

in the lumen, a liquid formulation of an ophthalmic drug suitable for intravitreal injection; and a closure seated in the lumen having a front face facing the liquid formulation, the closure being an axially stretchable plunger in the syringe barrel and axially slidable toward the front dispensing opening, the plunger comprising: an elastomeric sleeve having a sidewall and a front face facing the front dispensing opening, the sidewall comprising a stretch zone that is adapted to undergo axial elongation to convert the plunger from a storage mode to a dispensing mode, wherein the elongation reduces an outer profile of at least a portion of the sidewall, thus reducing the plunger to a constricted state;

wherein the plunger further comprises a liquid sealing section when the plunger is in the constricted state, and wherein the liquid sealing section comprises a non-stretch zone of the sidewall of the elastomeric sleeve; and wherein the syringe barrel and closure are free of silicone oil and baked-on silicone.

2. The ophthalmic drug in a pre-filled pharmaceutical package according to claim 1, further comprising a lubricity coating or layer positioned between the pH protective coating or layer and the lumen.

3. The ophthalmic drug in a pre-filled pharmaceutical package according to claim 2, wherein the lubricity coating or layer has the atomic proportions $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS.

4. The ophthalmic drug in a pre-filled pharmaceutical package according to claim 2, wherein the lubricity coating or layer is prepared by PECVD from an organosilicon precursor.

5. The ophthalmic drug in a pre-filled pharmaceutical package according to claim 4, wherein the lubricity coating or layer is prepared by PECVD from octamethylcyclotetrasiloxane (OMCTS) as the organosilicon precursor.

6. The ophthalmic drug in a pre-filled pharmaceutical package according to claim 1, in which the front face of the closure seated in the lumen is covered with a fluoropolymer coating or layer, wherein the front face is facing the liquid formulation.

7. The ophthalmic drug in a pre-filled pharmaceutical package according to claim 1, having a nominal maximum fill volume of 0.2 mL to 10 mL.

8. The ophthalmic drug in a pre-filled pharmaceutical package according to claim 1, in which the front face of the plunger has a fluoropolymer surface.

9. The ophthalmic drug in a pre-filled pharmaceutical package according to claim 1, wherein the ophthalmic drug suitable for intravitreal injection comprises a VEGF antagonist.

10. The ophthalmic drug in a pre-filled pharmaceutical package according to claim 9, wherein the VEGF antagonist comprises an anti-VEGF antibody or an antigen-binding fragment of such antibody.

11. The ophthalmic drug in a pre-filled pharmaceutical package according to claim 1, wherein the concentration of the liquid formulation of an ophthalmic drug suitable for intravitreal injection is 1 to 100 mg of a drug active agent per mL of the liquid formulation (mg/mL).

12. The ophthalmic drug in a pre-filled pharmaceutical package according to claim 1, in which the liquid formulation of an ophthalmic drug suitable for intravitreal injection comprises 6 mg/mL or 10 mg/mL of the ophthalmic drug.

13. The ophthalmic drug in a pre-filled pharmaceutical package according to claim 1, in which the ophthalmic drug suitable for intravitreal injection further comprises:

a buffer in an amount effective to provide a pH of the liquid formulation in the range from about 5 to about 7;

a non-ionic surfactant in the range of 0.005 to 0.02% (mg/mL) of complete formulation; and water for injection.

14. The ophthalmic drug in a pre-filled pharmaceutical package according to claim 1, in which the ophthalmic drug suitable for intravitreal injection comprises 6 mg/mL or 10 mg/mL of the drug active agent; 100 mg/mL of α, α-trehalose dihydrate, 1.98 mg/mL L-histidine; and 0.1 mg/mL Polysorbate 20 in water for injection.

15. The ophthalmic drug in a pre-filled pharmaceutical package according to claim 1, wherein the pre-filled pharmaceutical package has a shelf life of at least six months at a storage temperature of 4° C.

16. The ophthalmic drug in a pre-filled pharmaceutical package according to claim 1, in which the ophthalmic drug suitable for intravitreal injection meets the particle count standard for particulate matter in ophthalmic solutions of USP789 as in force on Nov. 1, 2015, or Ph. Eur 5.7.1 as in force on Nov. 1, 2015, or both, after three months of storage of the pre-filled syringe at 25° C. and 60% relative humidity, after three months of storage of the pre-filled syringe at 40° C. and 75% relative humidity, or both.

17. The ophthalmic drug in a pre-filled pharmaceutical package according to claim 1, in which the thermoplastic wall comprises a polyolefin; a polyester; a polycarbonate; or any combination or copolymer of any two or more of these.

18. The ophthalmic drug in a pre-filled pharmaceutical package according to claim 1, in which:

the tie coating or layer comprising $SiO_xC_yH_z$ is between 5 and 200 nm (nanometers) thick as determined by transmission electron microscopy;

the barrier coating or layer of $SiO_x$ is from 2 to 1000 nm thick as determined by transmission electron microscopy; and the pH protective coating or layer of $SiO_xC_yH_z$ is between 10 and 1000 nm thick as determined by transmission electron microscopy.

19. The ophthalmic drug in a pre-filled pharmaceutical package according to claim 1, in which, for the pH protective coating or layer of $SiO_xC_yH_z$, x is from about 1 to about 2 as measured by XPS, y is from about 0.6 to about 1.5 as measured by XPS, and z is from about 2 to about 5 as measured by RBS or HFS.

20. The ophthalmic drug in a pre-filled pharmaceutical package according to claim 1, in which for the pH protective coating or layer of $SiO_xC_yH_z$, x is about 1.1 as measured by XPS, y is about 1 as measured by XPS, and z is from about 2 to about 5 as measured by RBS or HFS.

21. The ophthalmic drug in a pre-filled pharmaceutical package according to claim 1, in which the pH protective coating or layer of $SiO_xC_yH_z$ has a density between 1.25 and 1.65 g/cm$^3$ as determined by X-ray reflectivity (XRR).

22. The ophthalmic drug in a pre-filled pharmaceutical package according to claim 1, in which the pH protective coating or layer of $SiO_xC_yH_z$ has a root mean square surface roughness value as measured by atomic force microscopy of from about 5 to about 9.

23. The ophthalmic drug in a pre-filled pharmaceutical package according to claim 1, in which the pH protective coating or layer of $SiO_xC_yH_z$ has a contact angle with distilled water of from 90° to 110° as measured by Goniometer Angle measurement of a water droplet on the pH protective surface, per ASTM D7334-08 "Standard Practice for Surface Wettability of Coatings, Substrates and Pigments by Advancing Contact Angle Measurement.

24. The ophthalmic drug in a pre-filled pharmaceutical package according to claim 1, in which the pH protective coating or layer of $SiO_xC_yH_z$ has an FTIR absorbance spectrum having a ratio from greater than 0.75 to 1.7 between the maximum amplitude of the Si—O—Si symmetrical stretch peak normally located between about 1000 and 1040 $cm^{-1}$, and the maximum amplitude of the Si—O—Si asymmetric stretch peak normally located between about 1060 and about 1100 $cm^{-1}$.

25. The ophthalmic drug in a pre-filled pharmaceutical package according to claim 1, in which the pH protective coating or layer of $SiO_xC_yH_z$ has a silicon dissolution rate by a 50 mM potassium phosphate buffer diluted in water for injection, adjusted to pH 8 with concentrated nitric acid, and containing 0.2 wt. % polysorbate-80 surfactant (measured in the absence of the liquid formulation of a VEGF antagonist, at 40° C.), less than 170 ppb/day.

26. The ophthalmic drug in a pre-filled pharmaceutical package according to claim 1, further comprising a tamper-evident needle shield.

27. The ophthalmic drug in a pre-filled pharmaceutical package according to claim 1, further comprising a luer lock on the syringe barrel.

28. The ophthalmic drug in a pre-filled pharmaceutical package according to claim 27, comprising a dispensing opening through the luer lock, the dispensing opening having a diameter of from 0.05 mm to less than 1.8 mm.

29. The ophthalmic drug in a pre-filled pharmaceutical package according to claim 1, further comprising an insert-molded staked needle and a needle shield.

30. The ophthalmic drug in a pre-filled pharmaceutical package according to claim 1, wherein the pre-filled pharmaceutical package is suitable for terminal sterilization by a sterilizing gas.

31. The ophthalmic drug in a pre-filled pharmaceutical package according to claim 1, wherein the non-stretch zone is provided by an insert having increased rigidity relative to the elastomeric sleeve.

32. An ophthalmic drug in a pre-filled pharmaceutical package comprising:
a syringe barrel having a front dispensing opening and a back opening, the syringe barrel comprising a thermoplastic wall having an interior surface enclosing at least a portion of a lumen, an exterior surface, and a coating set on the interior surface of the wall, the coating set comprising:
a pH protective coating or layer of $SiO_xC_yH_z$, in which x is from about 0.5 to about 2.4 as measured by XPS, y is from about 0.6 to about 3 as measured by XPS, and z is from about 2 to about 9 as measured by at least one of RBS or HFS;
in the lumen, a liquid formulation of a VEGF antagonist comprising an anti-VEGF antibody or an antigen-binding fragment of such antibody, such liquid formulation being suitable for intravitreal injection; and
a closure seated in the lumen having a front face facing the liquid formulation, the closure being an axially stretchable plunger in the syringe barrel and axially slidable toward the front dispensing opening, the plunger comprising: an elastomeric sleeve having a sidewall and a front face facing the front dispensing opening, the sidewall comprising a stretch zone that is adapted to undergo axial elongation to convert the plunger from a storage mode to a dispensing mode, wherein the elongation reduces an outer profile of at least a portion of the sidewall, thus reducing the plunger to a constricted state;
wherein the plunger further comprises a liquid sealing section when the plunger is in the constricted state, and wherein the liquid sealing section comprises a non-stretch zone of the sidewall of the elastomeric sleeve; and
wherein the syringe barrel and closure are free of silicone oil and baked-on silicone.

\* \* \* \* \*